United States Patent
Gotoh et al.

(10) Patent No.: US 10,100,251 B2
(45) Date of Patent: Oct. 16, 2018

(54) COMPOUNDS HAVING A DIFLUOROCYCLOHEXANE RING, LIQUID CRYSTAL COMPOSITIONS AND LIQUID CRYSTAL DISPLAY DEVICES

(71) Applicants: JNC CORPORATION, Tokyo (JP); JNC PETROCHEMICAL CORPORATION, Tokyo (JP)

(72) Inventors: Yasuyuki Gotoh, Tokyo (JP); Takahiro Kubo, Ichihara (JP)

(73) Assignees: JNC CORPORATION, Tokyo (JP); JNC PETROCHEMICAL CORPORATION, Tokyo (JP)

(*) Notice: Subject to any disclaimer, the term of this patent is extended or adjusted under 35 U.S.C. 154(b) by 0 days.

(21) Appl. No.: 15/439,680

(22) Filed: Feb. 22, 2017

(65) Prior Publication Data
US 2017/0240809 A1    Aug. 24, 2017

(30) Foreign Application Priority Data
Feb. 24, 2016 (JP) ................. 2016-032848

(51) Int. Cl.
*G02F 1/1333*    (2006.01)
*C09K 19/34*    (2006.01)
(Continued)

(52) U.S. Cl.
CPC .......... *C09K 19/3402* (2013.01); *C07C 13/28* (2013.01); *C07C 22/04* (2013.01); *C07C 23/18* (2013.01); *C07C 25/18* (2013.01); *C07C 43/192* (2013.01); *C07C 43/225* (2013.01); *C07C 69/75* (2013.01); *C07C 69/753* (2013.01); *C07C 69/76* (2013.01); *C07C 69/78* (2013.01); *C07C 69/92* (2013.01); *C09K 19/3001* (2013.01); *C09K 19/3003* (2013.01); *C09K 19/3066* (2013.01); *C09K 19/3068* (2013.01); *C09K 19/32* (2013.01); *C07C 2101/14* (2013.01); *C07C 2601/12* (2017.05); *C07C 2601/14* (2017.05); *C09K 2019/0466* (2013.01); *C09K 2019/122* (2013.01); *C09K 2019/123* (2013.01); *C09K 2019/301* (2013.01); *C09K 2019/3004* (2013.01); *C09K 2019/308* (2013.01); *C09K 2019/3009* (2013.01); *C09K 2019/3016* (2013.01); *C09K 2019/3019* (2013.01); *C09K 2019/3022* (2013.01); *C09K 2019/3077* (2013.01); *C09K 2019/3083* (2013.01); *C09K 2019/3422* (2013.01); *C09K 2019/3425* (2013.01)

(58) Field of Classification Search
CPC ............ C09K 19/3402; C09K 19/3001; C09K 19/3003; C09K 19/3066; C09K 19/3068; C09K 19/32; C09K 2019/3004; C09K 2019/3009; C09K 2019/301; C09K 2019/3016; C09K 2019/3077; C09K 2019/308; C09K 2019/3083; C09K 2019/3422; C09K 2019/3425; C09K 2019/0466; C09K 2019/122; C09K 2019/123; C09K 2019/3019; C09K 2019/3022; C07C 69/753; C07C 69/78; C07C 69/75; C07C 69/76; C07C 69/92; C07C 43/192; C07C 43/225; C07C 13/28; C07C 22/04; C07C 23/18; C07C 25/18; C07C 2101/14; C07C 2601/12; C07C 2601/14
USPC .................................... 252/299.61
See application file for complete search history.

(56) References Cited

U.S. PATENT DOCUMENTS

| 4,422,951 A | 12/1983 | Sugimori et al. |
| 6,475,595 B1 * | 11/2002 | Bremer .......... C07C 23/18 252/299.61 |
| 2017/0210991 A1 * | 7/2017 | Gotoh ............. C09K 19/3402 |

FOREIGN PATENT DOCUMENTS

| JP | S57165328 A | 10/1982 |
| JP | 5320081 A | 12/1993 |
| JP | 8048978 A | 2/1996 |

* cited by examiner

*Primary Examiner* — Geraldina Visconti
(74) *Attorney, Agent, or Firm* — Hogan Lovells US LLP

(57) ABSTRACT

The invention provides a liquid crystal compound satisfying at least one of physical properties such as a high stability to heat or light, a high clearing point (or a high maximum temperature), a low minimum temperature of a liquid crystal phase, a small viscosity, a suitable optical anisotropy, a small dielectric anisotropy, a suitable elastic constant and a good compatibility with other liquid crystal compounds, a liquid crystal composition including this compound, and a liquid crystal display device containing this composition. The invention provides a compound represented by formula (1):

(1)

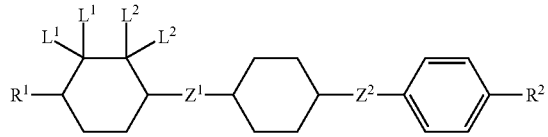

where $R^1$ and $R^2$ is alkyl having 1 to 20 carbons or the like; one of $L^1$ and $L^2$ is both hydrogens, and the other is both fluorines; $Z^1$ and $Z^2$ are independently a single bond, —COO—, —OCO—, —OCH$_2$—, —CH$_2$O—, —CF$_2$O—, —OCF$_2$—, —CH$_2$CH$_2$—, —CH=CH—, —C≡C— or the like.

13 Claims, No Drawings

(51) Int. Cl.
*C07C 23/18* (2006.01)
*C07C 25/18* (2006.01)
*C07C 43/192* (2006.01)
*C07C 43/225* (2006.01)
*C07C 69/753* (2006.01)
*C07C 69/78* (2006.01)
*C09K 19/30* (2006.01)
*C07C 69/75* (2006.01)
*C07C 69/76* (2006.01)
*C07C 69/92* (2006.01)
*C07C 13/28* (2006.01)
*C07C 22/04* (2006.01)
*C09K 19/32* (2006.01)
*C09K 19/04* (2006.01)
*C09K 19/12* (2006.01)

COMPOUNDS HAVING A DIFLUOROCYCLOHEXANE RING, LIQUID CRYSTAL COMPOSITIONS AND LIQUID CRYSTAL DISPLAY DEVICES

TECHNICAL FIELD

The invention relates to a compound having a difluorocyclohexane ring, a liquid crystal composition including the compound, a liquid crystal display device containing the composition, and so forth.

TECHNICAL BACKGROUND

In a liquid crystal display device, a classification based on an operating mode for liquid crystal molecules includes modes such as PC (phase change), TN (twisted nematic), STN (super twisted nematic), ECB (electrically controlled birefringence), OCB (optically compensated bend), IPS (in-plane switching), VA (vertical alignment), FFS (fringe field switching) and FPA (field-induced photo-reactive alignment). A classification based on a driving mode in the device includes PM (passive matrix) and AM (active matrix). The PM is classified into static, multiplex and so forth, and the AM is classified into TFT (thin film transistor), MIM (metal-insulator-metal) and so forth. The TFT is further classified into amorphous silicon and polycrystal silicon. The latter is classified into a high temperature type and a low temperature type depending on the production process. A classification based on a light source includes a reflection type utilizing natural light, a transmission type utilizing a backlight and a semi-transmission type utilizing both natural light and a backlight.

The liquid crystal display device includes a liquid crystal composition having a nematic phase. This composition has suitable characteristics. An AM device having good characteristics can be obtained by improving the characteristics of this composition. Table 1 below summarizes the relationship between two characteristics. The characteristics of the composition will be further explained on the basis of a commercially available AM device. The temperature range of a nematic phase relates to the temperature range in which the device can be used. A desirable maximum temperature of the nematic phase is approximately 70° C. or higher and a desirable minimum temperature of the nematic phase is approximately −10° C. or lower. The viscosity of the composition relates to the response time of the device. A short response time is desirable for displaying moving images on the device. Response time that is one millisecond shorter than that of the other devices is desirable. Thus a small viscosity of the composition is desirable. A small viscosity at a low temperature is more desirable.

TABLE 1

Characteristics of compositions and AM devices

| No. | Characteristics of compositions | Characteristics of AM devices |
| --- | --- | --- |
| 1 | a wide temperature range of a nematic phase | a wide temperature range in which the device can be used |
| 2 | a small viscosity | a short response time |
| 3 | a suitable optical anisotropy | a large contrast ratio |
| 4 | a large positive or large negative dielectric anisotropy | a low threshold voltage and low power consumption, a large contrast ratio |
| 5 | a large specific resistance | a large voltage holding ratio and a large contrast ratio |
| 6 | a high stability to ultraviolet light or heat | a long service life |
| 7 | a large elastic constant | a large contrast ratio and a short response time |

The liquid crystal composition is prepared by mixing a liquid crystal compound having a large dielectric anisotropy and a liquid crystal compound having a small dielectric anisotropy. The dielectric anisotropy of the composition is increased by the former, and thus the threshold voltage of the device decreases. The maximum temperature of a nematic phase of the composition is increased or the minimum temperature of a nematic phase is decreased by the latter, and thus the temperature range in which the device can be used increases. The viscosity of the composition is decreased by the latter, and thus the response time of the device decreases.

A variety of liquid crystal compounds having a large positive or large negative dielectric anisotropy have been prepared until now. In contrast, a conventional compound is often used for a liquid crystal compound having a small dielectric anisotropy. Thus, we try to synthesize a new compound. This is because good physical properties that cannot be observed in the conventional compound are expected.

JP S57-165328 A (1982) discloses compound (A) in Example 25.

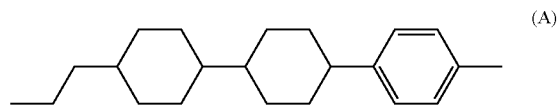

(A)

JP H08-048978 A (1996) discloses compound (B) in Example 7.

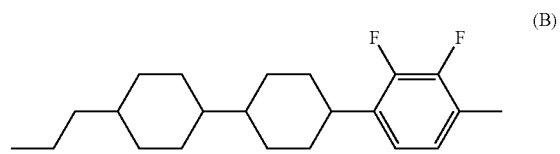

(B)

JP H05-320081 A (1993) discloses compound (C) in Example 1.

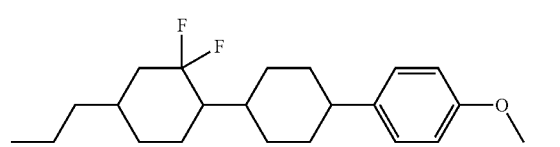

(C)

Compound (D) is disclosed in Proceedings of SPIE—The International Society for Optical Engineering (1998), 3319 (Liquid Crystals: Chemistry and Structure), 31-34.

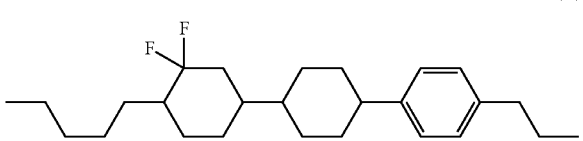

(D)

PRIOR ART

Patent Document

Patent document No. 1: JP S57-165328 A (1982).
Patent document No. 2: JP H08-048978 A (1996).
Patent document No. 3: JP H05-320081 A (1993).

Non-Patent Document

Non-patent document No. 1: Proceedings of SPIE—The International Society for Optical Engineering (1998), 3319 (Liquid Crystals: Chemistry and Structure), 31-34.

SUMMARY OF THE INVENTION

Subject to be Solved by the Invention

The first subject is to provide a liquid crystal compound satisfying at least one of physical properties such as a high stability to heat or light, a high clearing point (or a high maximum temperature of a nematic phase), a low minimum temperature of a liquid crystal phase, a small viscosity, a suitable optical anisotropy, a small dielectric anisotropy, a suitable elastic constant and a good compatibility with other liquid crystal compounds. It is to provide a compound having physical properties such as a good compatibility in comparison with a similar compound. The second subject is to provide a liquid crystal composition including this compound and satisfying at least one of physical properties such as a high stability to heat or light, a high maximum temperature of a nematic phase, a low minimum temperature of a nematic phase, a small viscosity, a suitable optical anisotropy, a large positive or large negative dielectric anisotropy, a large specific resistance and a suitable elastic constant. The subject is to provide a liquid crystal composition having a suitable balance regarding at least two of the physical properties. The third subject is to provide a liquid crystal display device containing this composition and having a wide temperature range in which the device can be used, a short response time, a large voltage holding ratio, a low threshold voltage, a large contrast ratio, a small flicker rate and a long service life.

Means for Solving the Subject

The invention concerns a compound represented by formula (1), a liquid crystal composition including this compound, and a liquid crystal display device containing this composition.

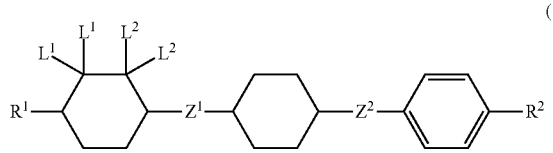

(1)

In formula (1),
$R^1$ and $R^2$ is hydrogen, fluorine, chlorine or alkyl having 1 to 20 carbons, and in the alkyl at least one —$CH_2$— may be replaced by —O—, at least one —$CH_2CH_2$— may be replaced by —CH=CH—, and in these groups at least one hydrogen may be replaced by fluorine;
one of $L^1$ and $L^2$ is both hydrogens, and the other is both fluorines; and
$Z^1$ and $Z^2$ are independently a single bond, —COO—, —OCO—, —$OCH_2$—, —$CH_2O$—, —$CF_2O$—, —$OCF_2$—, —$CH_2CH_2$—, —CH=CH—, —C≡C—, —$CF_2CF_2$—, —CF=CF—, —$CH_2CH_2CH_2CH_2$—, —CH=$CHCH_2CH_2$— or —$CH_2CH$=$CHCH_2$—.

Effect of the Invention

The first advantage is to provide a liquid crystal compound satisfying at least one of physical properties such as a high stability to heat or light, a high clearing point (or a high maximum temperature of a nematic phase), a low minimum temperature of a liquid crystal phase, a small viscosity, a suitable optical anisotropy, a small dielectric anisotropy, a suitable elastic constant and a good compatibility with other liquid crystal compounds. It is to provide a compound having physical properties such as a good compatibility in comparison with a similar compound (see Comparative examples 1 and 2). The second advantage is to provide a liquid crystal composition including this compound and satisfying at least one of physical properties such as a high stability to heat or light, a high maximum temperature of a nematic phase, a low minimum temperature of a nematic phase, a small viscosity, a suitable optical anisotropy, a large positive or large negative dielectric anisotropy, a large specific resistance and a suitable elastic constant. The advantage is to provide a liquid crystal composition having a suitable balance regarding at least two of the physical properties. The third advantage is to provide a liquid crystal display device containing this composition and having a wide temperature range in which the device can be used, a short response time, a large voltage holding ratio, a low threshold voltage, a large contrast ratio, a small flicker rate and a long service life.

EMBODIMENT TO CARRY OUT THE INVENTION

Usage of the terms in this specification is as follows. The terms, "liquid crystal compound", "liquid crystal composition" and "liquid crystal display device" are sometimes abbreviated to "compound", "composition" and "device", respectively. "Liquid crystal compound" is a generic term for a compound having a liquid crystal phase such as a nematic phase or a smectic phase, and for a compound having no liquid crystal phases but being mixed to a composition for the purpose of adjusting the physical properties of the composition, such as the maximum temperature, the minimum temperature, the viscosity and the dielectric anisotropy. This compound has a six-membered ring such as 1,4-cyclohexylene or 1,4-phenylene, and its molecular structure is rod-like. "Liquid crystal display device" is a generic term for a liquid crystal display panel and a liquid crystal display module. "Polymerizable compound" is a compound that is added to a composition in order to form a polymer in it.

A liquid crystal composition is prepared by mixing a plurality of liquid crystal compounds. An additive is added to the composition for further adjusting the physical properties. An additive such as a polymerizable compound, a polymerization initiator, a polymerization inhibitor, an optically active compound, an antioxidant, an ultraviolet light absorber, a light stabilizer, a thermal stabilizer, a coloring matter and an antifoaming agent is added as required. The liquid crystal compounds or the additive is mixed according to this procedure. Even if an additive is added, the ratio of a liquid crystal compound (content) is expressed as a percentage by weight (% by weight) based on the weight of the liquid crystal composition excluding the additive. The ratio of the additive (added amount) is expressed as a percentage by weight (% by weight) based on the weight of the liquid crystal composition excluding the additive. Weight parts per million (ppm) is sometimes used. The ratio of the polymerization initiator or the polymerization inhibitor is exceptionally expressed on the basis of the weight of the polymerizable compound.

"Clearing point" is the transition temperature between a liquid crystal phase and an isotropic phase of a liquid crystal compound. "Minimum temperature of a liquid crystal phase" is the transition temperature between solids and a liquid crystal phase (a smectic phase, a nematic phase or the like) of a liquid crystal compound. "Maximum temperature of a nematic phase" is the transition temperature between a nematic phase and an isotropic phase in a mixture of a liquid crystal compound and mother liquid crystals or in a liquid crystal composition, and is sometimes abbreviated to "maximum temperature". "Minimum temperature of a nematic phase" is sometimes abbreviated to "minimum temperature". The expression "the dielectric anisotropy increases" means that its value increases positively when the composition has positive dielectric anisotropy, and that its value increases negatively when the composition has negative dielectric anisotropy. That "a voltage holding ratio is large" means that a device has a large voltage holding ratio at a temperature close to the maximum temperature as well as at room temperature in the initial stages, and that the device has a large voltage holding ratio at a temperature close to the maximum temperature as well as at room temperature, after it has been used for a long time. In compositions or devices, characteristics before or after a long-term test (including an accelerated aging test) are sometimes studied.

A compound represented by formula (1) is sometimes abbreviated to compound (1). At least one compound selected from the group of compounds represented by formula (1) is sometimes abbreviated to compound (1). "Compound (1)" means one compound, a mixture of two compounds or a mixture of three or more compounds, represented by formula (1). These rules apply to a compound represented by other formulas. In formulas (1) to (15), the symbol such as $A^1$, $B^1$ and $C^1$ surrounded by a hexagon corresponds to a six-membered ring such as ring $A^1$, ring $B^1$ and ring $C^1$, respectively. A hexagon represents a six-membered ring such as cyclohexane or benzene. The hexagon sometimes represents a condensed ring such as naphthalene or a bridged ring such as adamantane.

The symbol for the terminal group, $R^{11}$, was used for a plurality of compounds in the chemical formulas of component compounds. In these compounds, two groups represented by two arbitrary $R^{11}$ may be the same or different. In one case, for example, $R^{11}$ of compound (2) is ethyl and $R^{11}$ of compound (3) is ethyl. In another case, $R^{11}$ of compound (2) is ethyl and $R^{11}$ of compound (3) is propyl. The same rule applies to other symbols such as $R^{12}$, $R^{13}$ and $Z^{11}$. In compound (5), two rings $C^1$ are present when i is 2. In this compound, two groups represented by two rings $C^1$ may be the same or different. The same rule applies to two arbitrary rings $C^1$, when i is greater than 2. The same rule also applies to other symbols.

The expression "at least one 'A'" means that the number of 'A' is arbitrary. The expression "at least one 'A' may be replaced by B'" means that the position of 'A' is arbitrary when the number of 'A' is one, and the positions can also be selected without restriction when the number of 'A' is two or more. This rule also applies to the expression "at least one 'A' has been replaced by 'B'". The expression "at least one 'A' may be replaced by 'B', 'C' or 'D'" includes cases where arbitrary 'A' has been replaced by 'B', and arbitrary 'A' has been replaced by 'C', and arbitrary 'A' has been replaced by 'D', and also cases where a plurality of 'A' has been replaced by at least two of 'B', 'C' and/or 'D'. For example, "alkyl in which at least one —$CH_2$— may be replaced by —O— or —CH=CH—" includes alkyl, alkoxy, alkoxyalkyl, alkenyl, alkoxyalkenyl and alkenyloxyalkyl. Incidentally, it is undesirable that two successive —$CH_2$— should be replaced by —O— to give —O—O—. It is also undesirable that —$CH_2$— of a methyl moiety (—$CH_2$—H) in alkyl and so forth should be replaced by —O— to give —O—H.

The following expression is sometimes used: "$R^{11}$ and $R^{12}$ are independently alkyl having 1 to 10 carbons or alkenyl having 2 to 10 carbons, and in the alkyl and alkenyl at least one —$CH_2$— may be replaced by —O—, and in these groups at least one hydrogen may be replaced by fluorine". In the expression, "in these groups" may be interpreted literally. In this expression, "these groups" means alkyl, alkenyl, alkoxy, alkenyloxy and so forth. That is to say, "these groups" indicates all of the groups described ahead of the term "in these groups". This commonsensical interpretation is applied to the expression "in these monovalent groups" or "in these divalent groups". For example, "these monovalent groups" indicates all of the groups described ahead of the term "in these monovalent groups".

The alkyl of a liquid crystal compound is straight-chain or branched-chain, and does not include cycloalkyl. Straight-chain alkyl is generally preferable to branched-chain alkyl. These apply to a terminal group such as alkoxy and alkenyl. With regard to the configuration of 1,4-cyclohexylene, trans is preferable to cis for increasing the maximum temperature. 2-Fluoro-1,4-phenylene means the two divalent groups described below. Fluorine may be facing left (L) or facing right (R) in a chemical formula. The same rule also applies to an asymmetric divalent group formed from a ring by removing two hydrogens, such as tetrahydropyran-2,5-diyl.

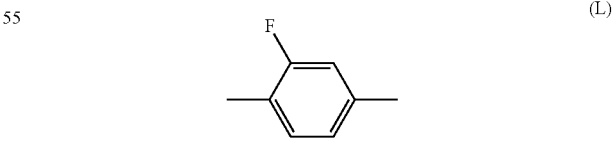

(L)

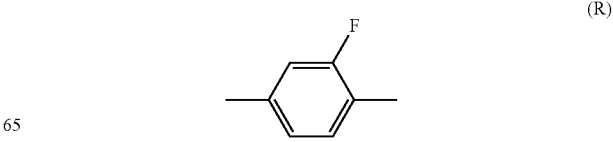

(R)

The invention includes the following items.
Item 1. A compound represented by formula (1):

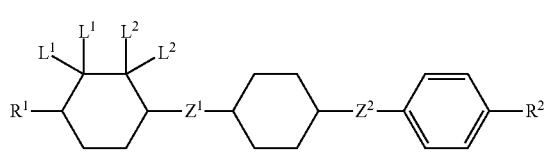
(1)

in formula (1), $R^1$ and $R^2$ is hydrogen, fluorine, chlorine or alkyl having 1 to 20 carbons, and in the alkyl at least one —$CH_2$— may be replaced by —O—, at least one —$CH_2CH_2$— may be replaced by —CH=CH—, and in these groups at least one hydrogen may be replaced by fluorine;

one of $L^1$ and $L^2$ is both hydrogens and the other is both fluorines; and $Z^1$ and $Z^2$ are independently a single bond, —COO—, —OCO—, —$OCH_2$—, —$CH_2O$—, —$CF_2O$—, —$OCF_2$—, —$CH_2CH_2$—, —CH=CH—, —C≡C—, —$CF_2CF_2$—, —CF=CF—, —$CH_2CH_2CH_2CH_2$—, —CH=$CHCH_2CH_2$— or —$CH_2CH$=$CHCH_2$—;

where at least one of $Z^1$ and $Z^2$ is —COO—, —OCO—, —$OCH_2$—, —$CH_2O$—, —$CF_2O$—, —$OCF_2$—, —$CH_2CH_2$—, —CH=CH—, —C≡C—, —$CF_2CF_2$—, —CF=CF—, —$CH_2CH_2CH_2CH_2$—, —CH=$CHCH_2CH_2$— or —$CH_2CH$=$CHCH_2$—, when both $R^1$ and $R^2$ is alkyl having 1 to 20 carbons and $L^1$ is fluorine;

where at least one of $Z^1$ and $Z^2$ is —COO—, —OCO—, —$OCH_2$—, —$CH_2O$—, —$CF_2O$—, —$OCF_2$—, —$CH_2CH_2$—, —CH=CH—, —C≡C—, —$CF_2CF_2$—, —CF=CF—, —$CH_2CH_2CH_2CH_2$—, —CH=$CHCH_2CH_2$— or —$CH_2CH$=$CHCH_2$—, when $R^1$ is alkyl having 1 to 20 carbons, $R^2$ is alkoxy having 1 to 19 carbons, and $L^2$ is fluorine.

Item 2. The compound according to item 1, wherein the compound is represented by formula (1-1), formula (1-2) or formula (1-3):

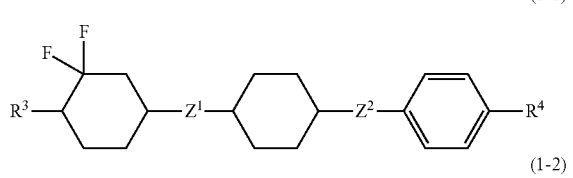
(1-1)

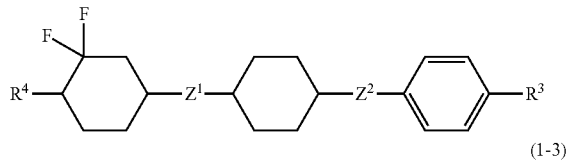
(1-2)

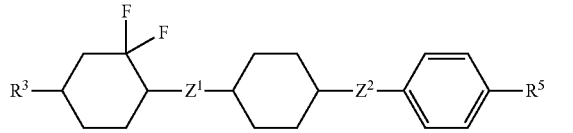
(1-3)

in formula (1-1), formula (1-2) and formula (1-3), $R^3$ is alkyl having 1 to 10 carbons, alkoxy having 1 to 9 carbons, alkoxyalkyl having 2 to 9 carbons, alkenyl having 2 to 10 carbons or alkenyloxy having 2 to 9 carbons, $R^4$ is alkoxy having 1 to 9 carbons, alkoxyalkyl having 2 to 9 carbons, alkenyl having 2 to 10 carbons or alkenyloxy having 2 to 9 carbons, $R^5$ is alkyl having 1 to 10 carbons or alkenyl having 2 to 10 carbons; and $Z^1$ and $Z^2$ are a single bond, —COO—, —$OCH_2$—, —$CF_2O$—, —$CH_2CH_2$—, —CH=CH—, —C≡C—, —$CF_2CF_2$—, —CF=CF—, —$CH_2CH_2CH_2CH_2$—, —CH=$CHCH_2CH_2$— or —$CH_2CH$=$CHCH_2$—.

Item 3. The compound according to item 1 or 2, wherein the compound is represented by formula (1-1-1), formula (1-2-1) or formula (1-3-1):

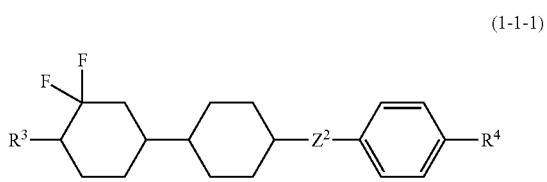
(1-1-1)

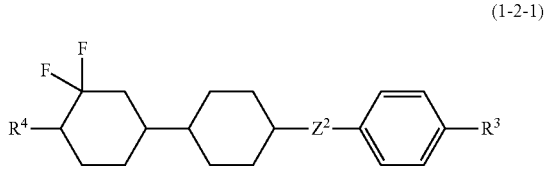
(1-2-1)

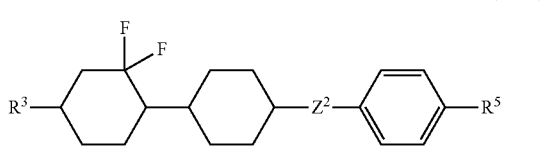
(1-3-1)

in formula (1-1-1), formula (1-2-1) and formula (1-3-1), $R^3$ is alkyl having 1 to 10 carbons, alkoxy having 1 to 9 carbons, alkoxyalkyl having 2 to 9 carbons, alkenyl having 2 to 10 carbons or alkenyloxy having 2 to 9 carbons; $R^4$ is alkoxy having 1 to 9 carbons, alkoxyalkyl having 2 to 9 carbons, alkenyl having 2 to 10 carbons or alkenyloxy having 2 to 9 carbons; $R^5$ is alkyl having 1 to 10 carbons or alkenyl having 2 to 10 carbons; and $Z^2$ is a single bond, —COO—, —$OCH_2$—, —$CF_2O$—, —$CH_2CH_2$—, —$CF_2CF_2$—, —$CH_2CH_2CH_2CH_2$—, —CH=$CHCH_2CH_2$— or —$CH_2CH$=$CHCH_2$—.

Item 4. The compound according to item 3, wherein in formula (1-1-1), formula (1-2-1) and formula (1-3-1), $Z^2$ is a single bond, —COO—, —$OCH_2$—, —$CF_2O$— or —$CH_2CH_2$—.

Item 5. The compound according to item 3, wherein in formula (1-1-1), formula (1-2-1) and formula (1-3-1), $Z^2$ is a single bond, —COO— or —$CH_2CH_2$—.

Item 6. The compound according to item 1, wherein the compound is represented by formula (1-1-1-1), formula (1-2-1-1) or formula (1-3-1-1):

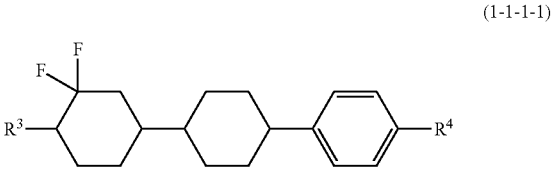
(1-1-1-1)

-continued (1-2-1-1)

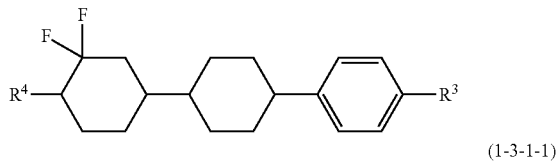

(1-3-1-1)

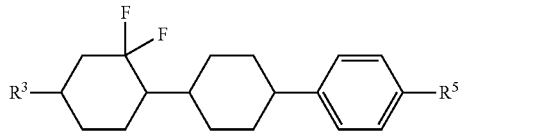

in formula (1-1-1-1), formula (1-2-1-1) and formula (1-3-1-1),
$R^3$ is alkyl having 1 to 5 carbons, alkoxy having 1 to 4 carbons or alkenyl having 2 to 5 carbons; $R^4$ is alkoxy having 1 to 4 carbons or alkenyl having 2 to 5 carbons; and $R^5$ is alkyl having 1 to 5 carbons or alkenyl having 2 to 5 carbons.

Item 7. The compound according to item 6, wherein in formula (1-1-1-1), formula (1-2-1-1) and formula (1-3-1-1), $R^1$ is alkyl having 1 to 5 carbons; $R^2$ is alkenyl having 2 to 5 carbons; and $R^3$ is alkyl having 1 to 5 carbons.

Item 8. A liquid crystal composition including a compound according to any one of items 1 to 7.

Item 9. The liquid crystal composition according to item 8, further including at least one compound selected from the group of compounds represented by formulas (2) to (4):

(2)

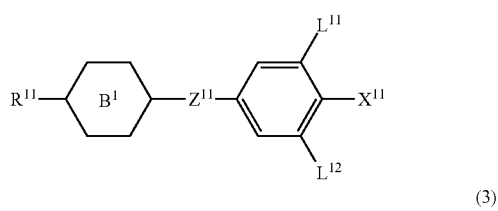

(3)

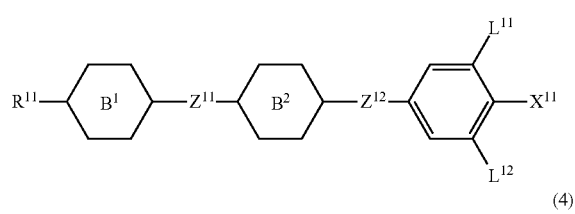

(4)

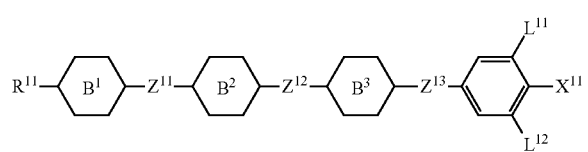

in formulas (2) to (4),
$R^{11}$ is alkyl having 1 to 10 carbons or alkenyl having 2 to 10 carbons, and in the alkyl and alkenyl at least one —$CH_2$— may be replaced by —O—, and in these groups at least one hydrogen may be replaced by fluorine;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $B^1$, ring $B^2$ and ring $B^3$ are independently 1,4-cyclohexylene, 1,4-phenylene, 1,4-phenylene in which at least one hydrogen has been replaced by fluorine, tetrahydropyran-2,5-diyl, 1,3-dioxane-2,5-diyl or pyrimidine-2,5-diyl;

$Z^{11}$, $Z^{12}$ and $Z^{13}$ are independently —COO—, —OCO—, —$CH_2O$—, —$OCH_2$—, —$CF_2O$—, —$OCF_2$—, —$CH_2CH_2$—, —CH=CH—, —C≡C— or —$(CH_2)_4$—; and $L^{11}$ and $L^{12}$ are independently hydrogen or fluorine.

Item 10. The liquid crystal composition according to item 8 or 9, further including at least one compound selected from the group of compounds represented by formula (5):

(5)

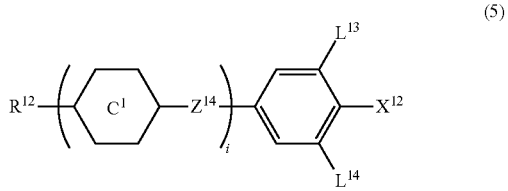

in formula (5),
$R^{12}$ is alkyl having 1 to 10 carbons or alkenyl having 2 to 10 carbons, and in the alkyl and alkenyl at least one —$CH_2$— may be replaced by —O—, and in these groups at least one hydrogen may be replaced by fluorine;

$X^{12}$ is —C≡N or —C≡C—C≡N;

ring $C^1$ is 1,4-cyclohexylene, 1,4-phenylene, 1,4-phenylene in which at least one hydrogen has been replaced by fluorine, tetrahydropyran-2,5-diyl, 1,3-dioxane-2,5-diyl or pyrimidine-2,5-diyl;

$Z^{14}$ is a single bond, —COO—, —OCO—, —$CH_2O$—, —$OCH_2$—$CF_2O$—, —$OCF_2$—, —$CH_2CH_2$— or $L^{13}$ and $L^{14}$ are independently hydrogen or fluorine; and i is 1, 2, 3 or 4.

Item 11. The liquid crystal composition according to any one of items 8 to 10, further including at least one compound selected from the group of compounds represented by formulas (6) to (12):

(6)

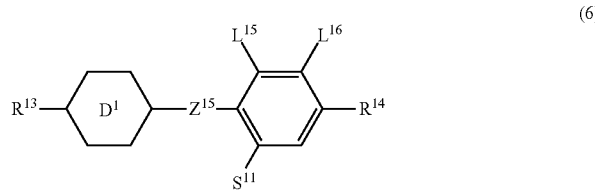

(7)

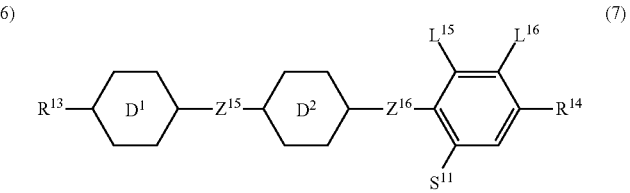

(8)
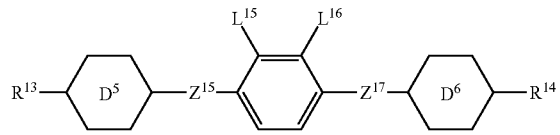

(9)
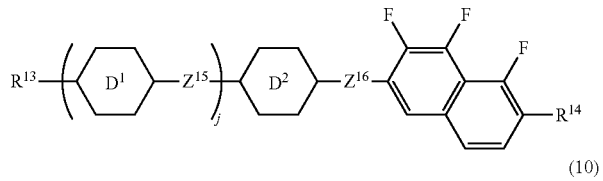

(10)
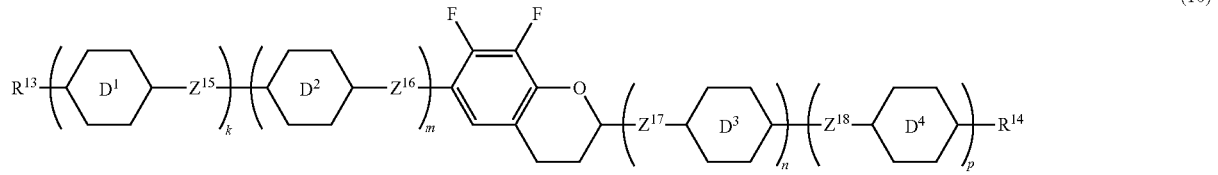

(11)
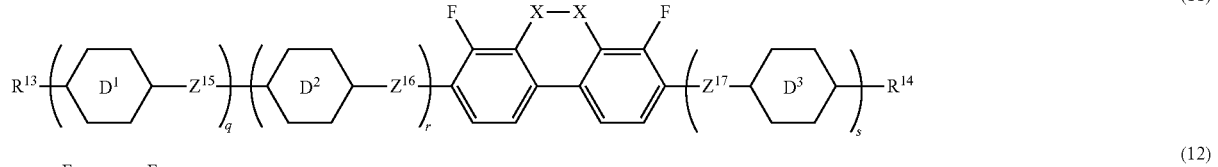

(12)
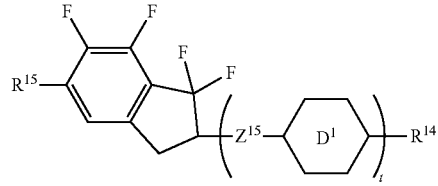

in formulas (6) to (12), $R^{13}$, $R^{14}$ and $R^{15}$ are independently alkyl having 1 to 10 carbons or alkenyl having 2 to 10 carbons, and in the alkyl and alkenyl at least one —$CH_2$— may be replaced by —O—, and in these groups at least one hydrogen may be replaced by fluorine, and $R^{15}$ may be hydrogen or fluorine;

ring $D^1$, ring $D^2$, ring $D^3$ and ring $D^4$ are independently 1,4-cyclohexylene, 1,4-cyclohexenylene, 1,4-phenylene, 1,4-phenylene in which at least one hydrogen has been replaced by fluorine, tetrahydropyran-2,5-diyl or decahydronaphthalene-2,6-diyl;

ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;

$Z^{15}$, $Z^{16}$, $Z^{17}$ and $Z^{18}$ are independently a single bond, —COO—, —OCO—, —$CH_2O$—, —$OCH_2$—, —$CF_2O$—, —$OCF_2$—, —$CH_2CH_2$—, —$CF_2OCH_2CH_2$— or —$OCF_2CH_2CH_2$—;

$L^{15}$ and $L^{16}$ are independently fluorine or chlorine;

$S^{11}$ is hydrogen or methyl;

X is —CHF— or —$CF_2$—; and j, k, m, n, p, q, r and s are independently 0 or 1, the sum of k, m, n and p is 1 or 2, the sum of q, r and s is 0, 1, 2 or 3, and t is 1, 2 or 3.

Item 12. The liquid crystal composition according to any one of items 8 to 11, further including at least one compound selected from the group of compounds represented by formulas (13) to (15):

(13)
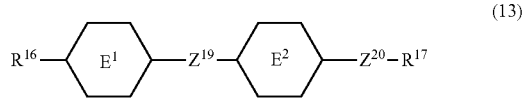

(14)
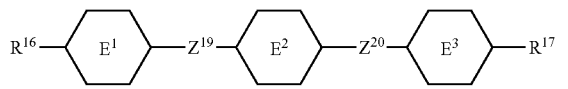

(15)
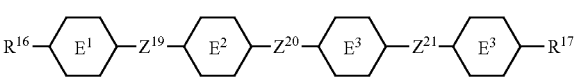

in formulas (13) to (15), $R^{16}$ and $R^{17}$ are independently alkyl having 1 to 10 carbons or alkenyl having 2 to 10 carbons, and in the alkyl and alkenyl at least one —$CH_2$— may be replaced by —O—, and in these groups at least one hydrogen may be replaced by fluorine;

ring $E^1$, ring $E^2$, ring $E^3$ and ring $E^4$ are independently 1,4-cyclohexylene, 1,4-phenylene, 2-fluoro-1,4-phenylene, 2,5-difluoro-1,4-phenylene or pyrimidine-2,5-diyl; and $Z^{19}$, $Z^{20}$ and $Z^{21}$ are independently a single bond, —COO—, —$CH_2CH_2$—, —CH=CH— or —C≡C—, where in formulas (14) and (15), when one of $R^{16}$ and $R^{17}$ is alkenyl having 2 to 10 carbons in which at least one hydrogen may be replaced by fluorine, the other is alkyl having 1 to 10 carbons in which at least one hydrogen may be replaced by fluorine.

Item 13. A liquid crystal display device containing the liquid crystal composition according to any one of items 8 to 12.

The invention further includes the following items. (a) The composition described above, further including one, two or at least three additives selected from the group of a polymerizable compound, a polymerization initiator, a polymerization inhibitor, an optically active compound, an antioxidant, an ultraviolet light absorber, a light stabilizer, a thermal stabilizer, a coloring matter and an antifoaming agent. (b) The liquid crystal composition described above, wherein the maximum temperature of a nematic phase is 70° C. or higher, the optical anisotropy (measured at 25° C.) at a wavelength of 589 nanometers is 0.07 or more, and the dielectric anisotropy (measured at 25° C.) at a frequency of 1 kHz is 2 or more. (c) The liquid crystal composition described above, wherein the maximum temperature of a nematic phase is 70° C. or higher, the optical anisotropy (measured at 25° C.) at a wavelength of 589 nanometers is 0.08 or more, and the dielectric anisotropy (measured at 25° C.) at a frequency of 1 kHz is −2 or less.

(d) The liquid crystal display device described above, wherein the operating mode of the liquid crystal display device is a TN mode, an ECB mode, an OCB mode, an IPS mode, a VA mode, an FFS mode or an FPA mode, and the driving mode of the liquid crystal display device is an active matrix (AM) mode.

(e) A liquid crystal display device having a polymer sustained alignment mode, produced by using the liquid crystal composition described above including a polymerizable compound.

The aspects of compound (1), the method for synthesizing compound (1), the liquid crystal composition and the liquid crystal display device will be explained successively.

1. Aspects of Compound (1)

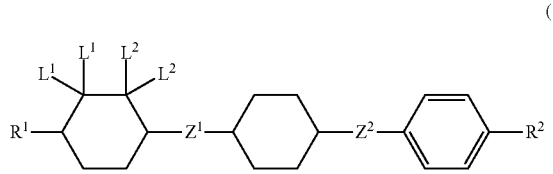

(1)

In formula (1), one of two $L^1$ and two $L^2$ is both hydrogens and the other is both fluorines. That is to say, compound (1) is characterized by having a divalent group represented by formula (A-1) or formula (A-2).

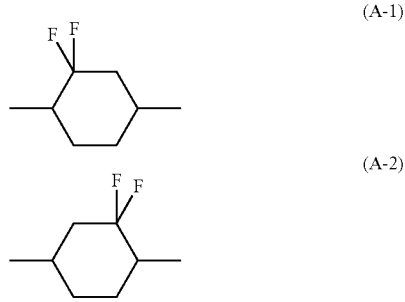

Compound (1) has a small dielectric anisotropy. This compound is stable physically and chemically under conditions in which a device is normally used. This compound has a good compatibility and a large elastic constant ratio ($K_{33}/K_{11}$) in comparison with a similar compound (see Comparative example 1). This compound is good in compatibility at low temperatures with other liquid crystal compounds. A composition including this compound is stable under conditions in which the device is normally used. When the composition is kept in storage at a low temperature, this compound has a small tendency to deposit its crystals (or a smectic phase). The response time of the device is decreased, since this compound has a large elastic constant. Compound (1) has a large elastic constant ratio ($K_{33}/K_{11}$) and a small rotational viscosity (γ1) in comparison with a similar compound (See Comparative example 2). This compound contributes a short response time of the device, since it decreases the viscosity of the composition.

Desirable examples of compound (1) will be explained. Desirable examples of terminal groups R, ring A and bonding group Z in compound (1) are applied to the sub-formulas of compound (1). In compound (1), the physical properties can be arbitrarily adjusted by a suitable combination of these groups. Compound (1) may also contain isotopes such as $^2H$ (deuterium) and $^{13}C$ in a larger amount than the amount of the natural abundance, since there are no major differences in physical properties of the compound. Incidentally, the definition of compound (1) is the same as that described in item 1.

In formula (1), $R^1$ and $R^2$ are hydrogen, fluorine, chlorine or alkyl having 1 to 20 carbons, and in the alkyl at least one —CH$_2$— may be replaced by —O—, at least one —CH$_2$CH$_2$— may be replaced by —CH═CH—, and in these groups at least one hydrogen may be replaced by fluorine.

Examples of $R^1$ or $R^2$ are hydrogen, fluorine, chlorine, alkyl, alkoxy, alkoxyalkyl, alkoxyalkoxy, alkenyl, alkenyloxy, alkenyloxyalkyl or alkoxyalkenyl. In these groups, at least one hydrogen may be replaced by fluorine. In these groups, a straight chain is preferable to a branched chain. The branched chain is also desirable when $R^1$ or $R^2$ is optically active. Desirable $R^1$ or $R^2$ is fluorine, chlorine, alkyl, alkoxy, alkoxyalkyl, alkenyl or alkenyloxy. More desirable $R^1$ or $R^2$ is alkyl, alkoxy or alkenyl. Especially desirable $R^1$ or $R^2$ is alkyl or alkenyl.

A desirable configuration of —CH═CH— in the alkenyl depends on the position of the double bond. The trans-configuration is preferable in the alkenyl such as 1-propenyl, 1-butenyl, 1-pentenyl, 1-hexenyl, 3-pentenyl or 3-hexenyl. The cis-configuration is preferable in the alkenyl such as 2-butenyl, 2-pentenyl or 2-hexenyl.

Specific $R^1$ or $R^2$ is hydrogen, fluorine, chlorine, methyl, ethyl, propyl, butyl, pentyl, hexyl, heptyl, octyl, methoxy, ethoxy, propoxy, butoxy, pentyloxy, hexyloxy, heptyloxy, methoxymethyl, methoxyethyl, methoxypropyl, ethoxymethyl, ethoxyethyl, ethoxypropyl, propoxymethyl, butoxymethyl, pentoxymethyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy, 2-pentenyloxy, 1-propynyl or 1-pentenyl.

Specific $R^1$ or $R^2$ is also 2-fluoroethyl, 3-fluoropropyl, 2,2,2-trifluoroethyl, 2-fluorovinyl, 2,2-difluorovinyl, 2-fluoro-2-vinyl, 3-fluoro-1-propenyl, 3,3,3-trifluoro-1-propenyl, 4-fluoro-1-propenyl or 4,4-difluoro-3-butenyl.

Desirable $R^1$ or $R^2$ is methyl, ethyl, propyl, butyl, pentyl, methoxy, ethoxy, propoxy, butoxy, pentyloxy, methoxymethyl, ethoxymethyl, propoxymethyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy or 2-pentenyloxy. More desirable $R^1$ is methyl, ethyl, propyl, butyl, pentyl or methoxymethyl. More desirable $R^2$ is methyl, ethyl, propyl, butyl, pentyl, vinyl, propenyl, butenyl or pentenyl.

In formula (1), $Z^1$ and $Z^2$ are independently a single bond, —COO—, —OCO—, —OCH$_2$—, —CH$_2$O—, —CF$_2$O—, —OCF$_2$—, —CH$_2$CH$_2$—, —CH═CH—, —C≡C—, —CF$_2$CF$_2$—, —CF═CF—, —CH$_2$CH$_2$CH$_2$CH$_2$—, —CH═CHCH$_2$CH$_2$— or —CH$_2$CH═CHCH$_2$—.

Desirable $Z^1$ or $Z^2$ is a single bond, —COO—, —OCO—, —OCH$_2$—, —CH$_2$O—, —CF$_2$O—, —OCF$_2$—, —CH$_2$CH$_2$—, —CH=CH—, —C≡C—, —CF$_2$CF$_2$— or —CF=CF—. More desirable $Z^1$ or $Z^2$ is a single bond, —COO—, —OCO—, —OCH$_2$—, —CH$_2$O—, —CF$_2$O—, —OCF$_2$—, —CH$_2$CH$_2$— or —C≡C—. Especially desirable $Z^1$ or $Z^2$ is a single bond, —OCH$_2$—, —CH$_2$O— or —CH$_2$CH$_2$—. The most desirable $Z^1$ or $Z^2$ is a single bond.

2. Preparation of Compound (1)

The method for synthesizing compound (1) will be explained. Compound (1) can be prepared by a suitable combination of methods in synthetic organic chemistry. Methods of introducing the required terminal group, ring and bonding group into starting materials are described in books such as "Organic Syntheses" (John Wiley & Sons, Inc.), "Organic Reactions" (John Wiley & Sons, Inc.), "Comprehensive Organic Synthesis" (Pergamon Press) and "Shin Jikken Kagaku Kouza" (New Experimental Chemistry Course, in English; Maruzen Co., Ltd., Japan).

2-1. Formation of Bonding Group Z

In the method for forming bonding groups $Z^1$ to $Z^4$, the schemes will be shown first. Next, the reactions described in the schemes will be explained in methods (1) to (11). In the schemes, MSG$^1$ (or MSG$^2$) is a monovalent organic group having at least one ring. Monovalent organic groups represented by a plurality of MSG$^1$ (or MSG$^2$) may be the same or different. Compounds (1A) to (1K) correspond to compound (1).

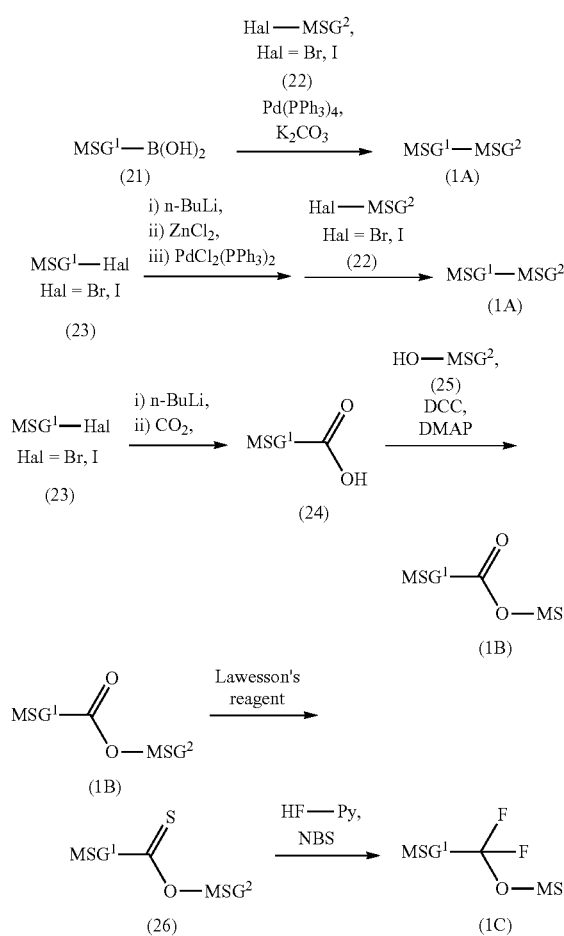

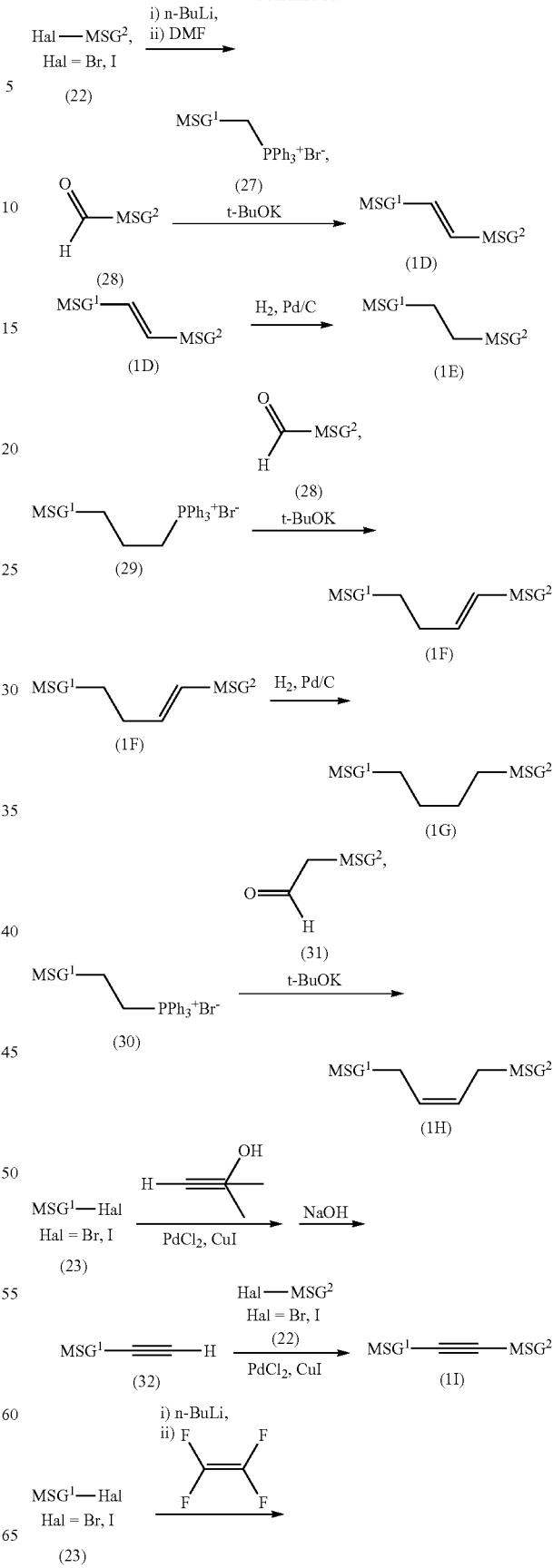

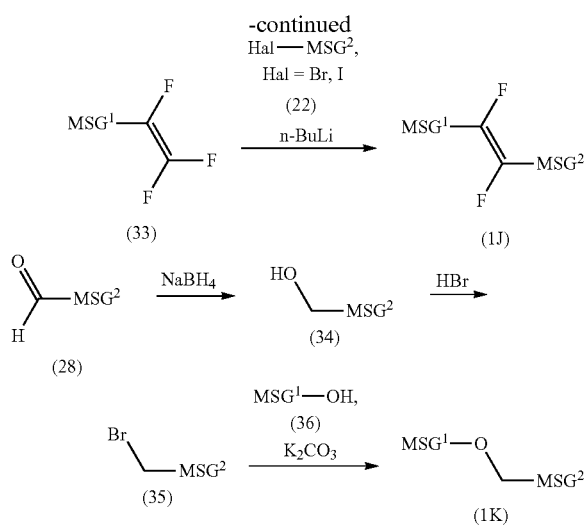

(1) Formation of a Single Bond

Compound (1A) is prepared by the reaction of arylboronic acid (21) prepared by known methods, with halide (22) in the presence of a carbonate and a catalyst such as tetrakis(triphenylphosphine)palladium. Compound (1A) is also be prepared by the reaction of halide (23) prepared by known methods, with n-butyllithium, and then with zinc chloride, and by the reaction with halide (22) in the presence of a catalyst such as dichlorobis(triphenylphosphine)palladium.

(2) Formation of —COO—

Carboxylic acid (24) is prepared by the reaction of halide (23) with n-butyllithium and then with carbon dioxide. Dehydration of compound (25) prepared by known methods and carboxylic acid (24), in the presence of DCC (1,3-dicyclohexylcarbodiimide) and DMAP (4-dimethylaminopyridine), gives compound (1B).

(3) Formation of —CF$_2$O—

Compound (1B) is treated with a thionating agent such as Lawesson's reagent, giving thionoester (26). Fluorination of thionoester (26) with a HF-pyridine complex and NBS (N-bromosuccinimide) gives compound (1C). See M. Kuroboshi et al., Chem. Lett., 1992, 827. Compound (1C) is also prepared by fluorination of thionoester (26) with (diethylamino)sulfur trifluoride (DAST). See W. H. Bunnelle et al., J. Org. Chem. 1990, 55, 768. This bonding group can also be formed by the method described in Peer. Kirsch et al., Angew. Chem. Int. Ed. 2001, 40, 1480.

(4) Formation of —CH=CH—

Halide (22) is treated with n-butyllithium, and then reacted with DMF (N,N-dimethylformamide) to give aldehyde (28). Phosphonium salt (27) is treated with a base such as potassium t-butoxide to generate a phosphorus ylide. The ylide is reacted with aldehyde (28) to give compound (1D). Since the cis-isomer is formed depending on the reaction conditions, the cis-isomer is isomerized to the trans-isomer by known methods as requested.

(5) Formation of —CH$_2$CH$_2$—

Compound (1E) is prepared by hydrogenation of compound (1D) in the presence of a catalyst such as palladium on carbon.

(6) Foramation of —(CH$_2$)$_2$—CH=CH—

Compound (1F) is obtained according to method (4) using phosphonium salt (29) instead of phosphonium salt (27). Since the cis-isomer is formed in this reaction, depending on the reaction conditions in some cases, the cis-isomer is isomerized to the trans-isomer by known methods.

(7) Formation of —(CH$_2$)$_4$—

Catalytic hydrogenation of compound (1F) gives compound (1G).

(8) Formation of —CH$_2$CH=CHCH$_2$—

Compound (1H) is prepared according to method (4) using phosphonium salt (30) instead of phosphonium salt (27), and using aldehyde (31) instead of aldehyde (28). Since the trans-isomer is formed depending on the reaction conditions, the trans-isomer is isomerized to the cis-isomer by known methods as requested.

(9) Formation of —C≡C—

The reaction of halide (23) with 2-methyl-3-butyn-2-ol in the presence of a catalyst of dichloropalladium and copper halide, followed by the deprotection of the product under basic conditions gives compound (32). Compound (32) is reacted with halide (22) in the presence of a catalyst of dichloropalladium and copper halide, giving compound (1I).

(10) Formation of —CF=CF—

Halide (23) is treated with n-butyllithium, which is allowed to react with tetrafluoroethylene to give compound (33). Halide (22) is treated with n-butyllithium, and then reacted with compound (33) to give compound (1J).

(11) Formation of —OCH$_2$—

Aldehyde (28) is reduced with a reducing agent such as sodium borohydride to give compound (34). Compound (34) is brominated with hydrobromic acid or the like, giving bromide (35). Bromide (35) is allowed to react with compound (36) in the presence of a base such as potassium carbonate to give compound (1K).

(12) Formation of —(CF$_2$)$_2$—

According to the method described in J. Am. Chem. Soc., 2001, 123, 5414, diketone (—COCO—) is fluorinated with sulfur tetrafluoride in the presence of a hydrogen fluoride catalyst, giving a compound having —(CF$_2$)$_2$—.

2-2. Formation of a Difluorocyclohexane Ring

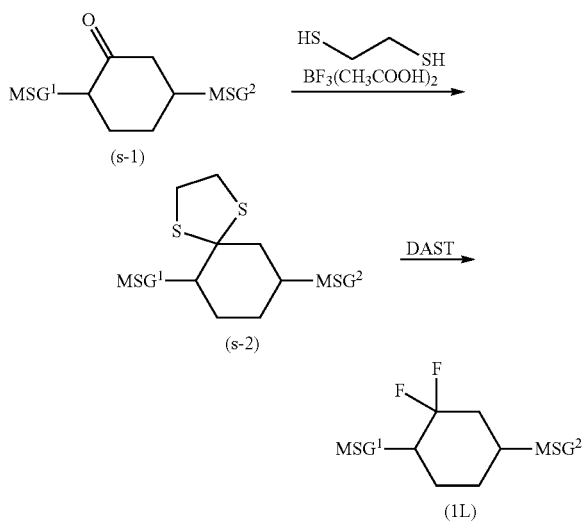

Methods for the formation of a difluorocyclohexane ring will be explained. Ketone (s-1) is commercially available, or methods for the formation are well known. Ketone (s-1) is reacted with ethanedithiol using a boron trifluoride-acetic acid complex to give thioketal (s-2). The thioketal is reacted with a fluorination agent such as (diethylamino)sulfur trifluoride (DAST) to give the target compound (1L).

3. Liquid Crystal Compositions

3-1. Component Compounds

The liquid crystal composition of the invention will be explained. The composition includes at least one of compound (1) as component A. The composition may include two or three or more of compound (1). The component of the composition may also be compound (1) alone. It is desirable that the composition should include at least one of compound (1) in the range of 1% to 50% by weight in order to exhibit good physical properties. Compound (1) has a small dielectric anisotropy. In a composition having positive dielectric anisotropy, a desirable content of compound (1) is in the range of 5% by weight to 50% by weight. In a composition having negative dielectric anisotropy, a desirable content of compound (1) is in the range of 5% by weight to 40% by weight.

TABLE 2

Dielectric anisotropy of component compounds

| Components of the composition | Component compounds | Dielectric anisotropy |
|---|---|---|
| Component A | Compound (1) | small |
| Component B | Compound (2) to Compound (4) | large positive |
| Component C | Compound (5) | large positive |
| Component D | Compound (6) to Compound (12) | large negative |
| Component E | Compound (13) to Compound (16) | small |

The composition includes compound (1) as component A. It is desirable that the composition should further include a liquid crystal compound selected from components B, C, D and E shown in Table 2. It is desirable that components B, C, D and E should be selected in consideration of the sign and magnitude of the dielectric anisotropy, when the composition is prepared. This composition may include a liquid crystal compound that is different from components B, C, D and E. This composition may not include such a liquid crystal compound.

Component B is a compound having halogen or a fluorine-containing group at the far right. Desirable examples of component B include compounds (2-1) to (2-16), compounds (3-1) to (3-113), compounds (4-1) to (4-57). In these compounds, $R^{11}$ is alkyl having 1 to 10 carbons or alkenyl having 2 to 10 carbons, and in the alkyl and alkenyl at least one —$CH_2$— may be replaced by —O—, and in these groups at least one hydrogen may be replaced by fluorine. $X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$.

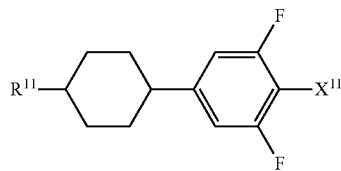
(2-1)

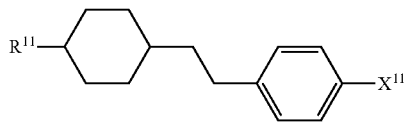
(2-2)

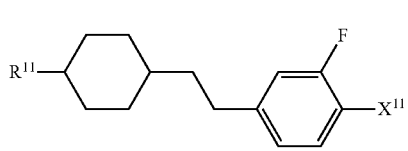
(2-3)

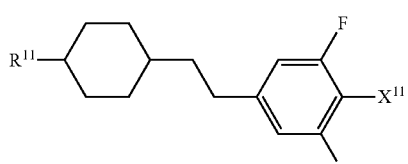
(2-4)

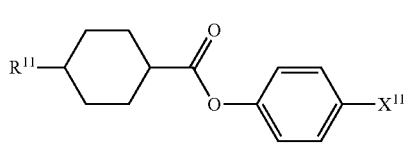
(2-5)

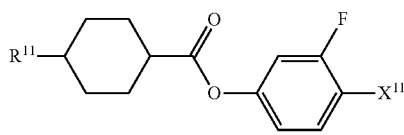
(2-6)

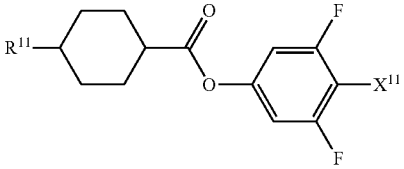
(2-7)

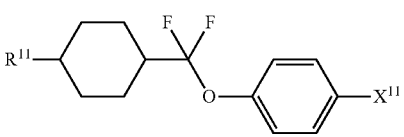
(2-8)

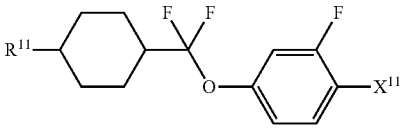
(2-9)

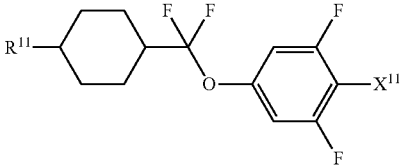
(2-10)

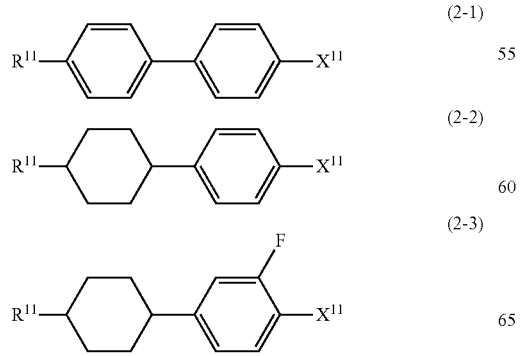
(2-11)

(2-12)

(2-13)

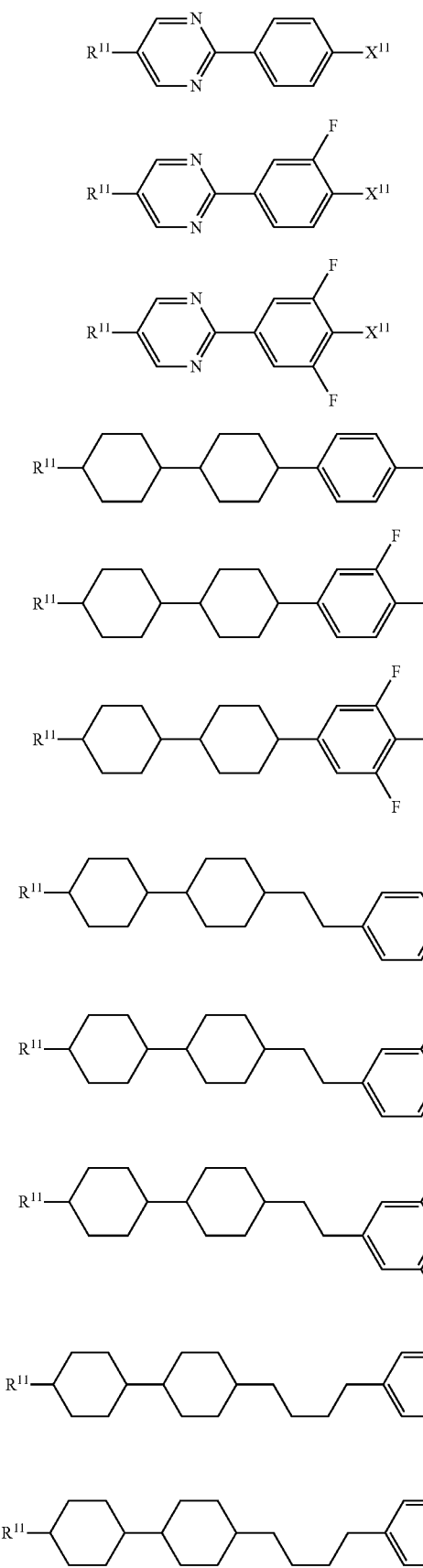
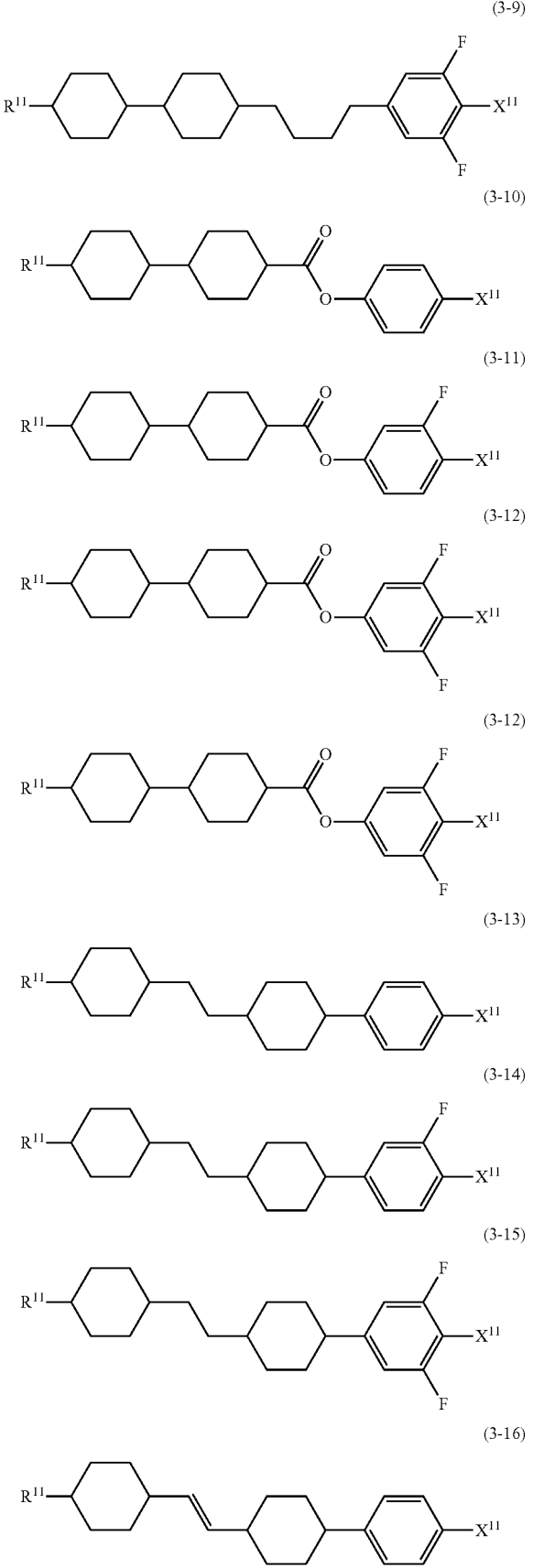

(3-17)
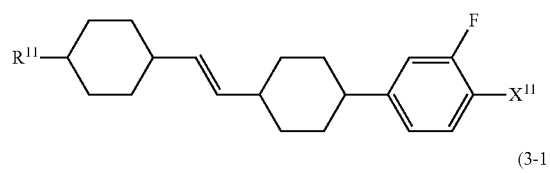
(3-18)
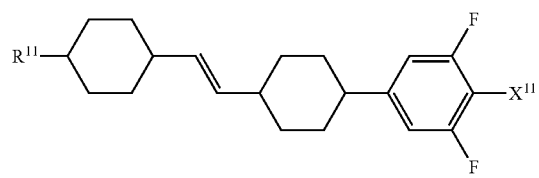
(3-19)
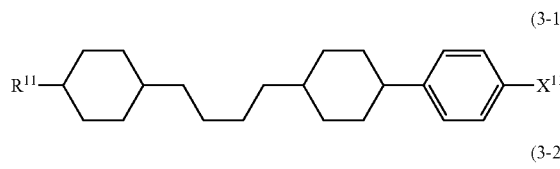
(3-20)
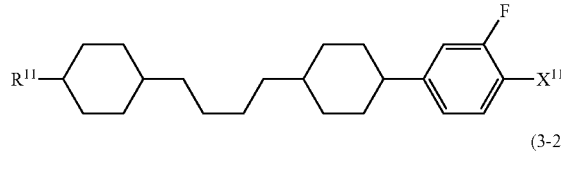
(3-21)
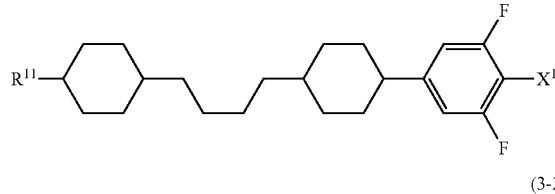
(3-22)
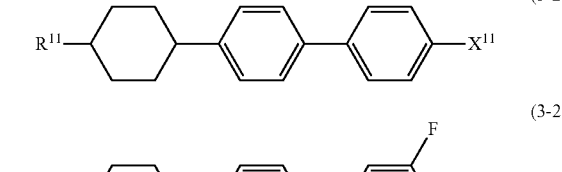
(3-23)
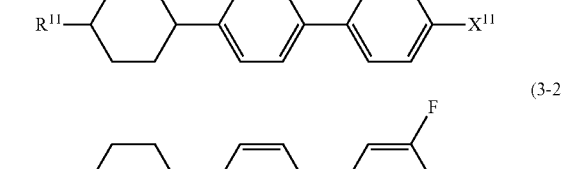
(3-24)
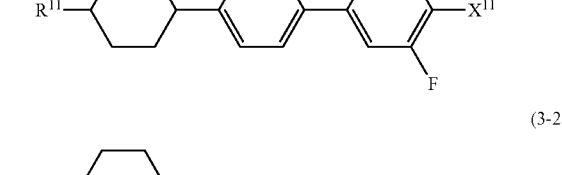
(3-25)
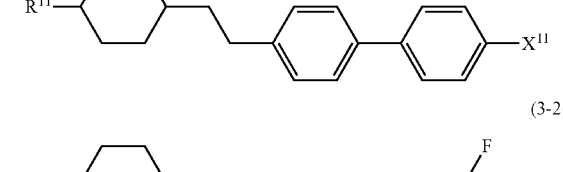
(3-26)
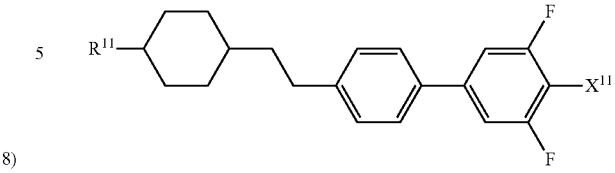
(3-27)
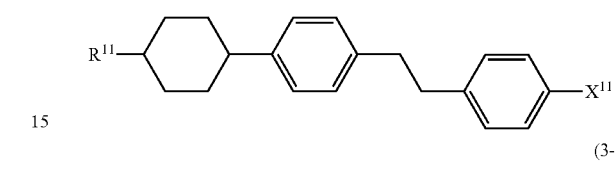
(3-28)
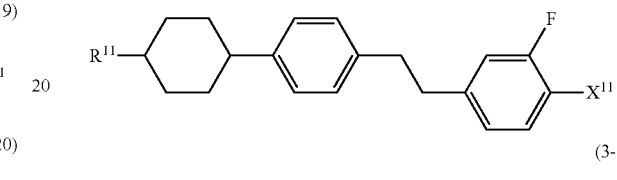
(3-29)
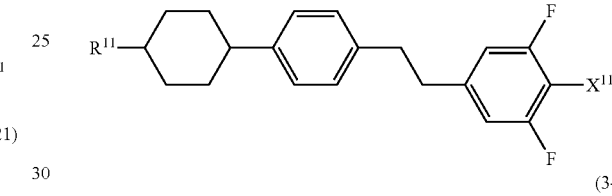
(3-30)
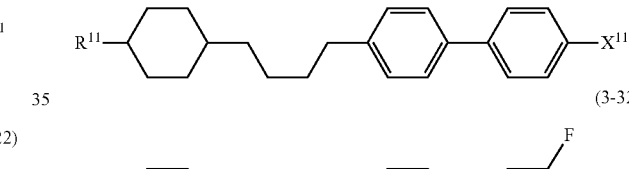
(3-31)
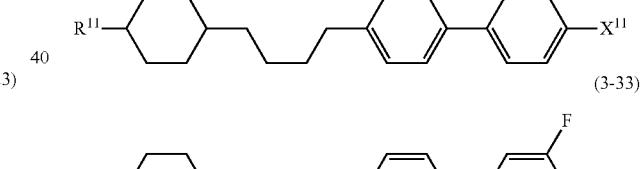
(3-32)
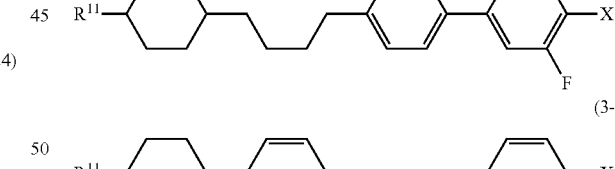
(3-33)
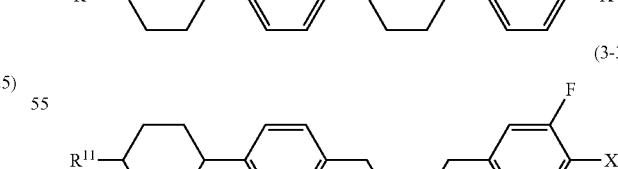
(3-34)
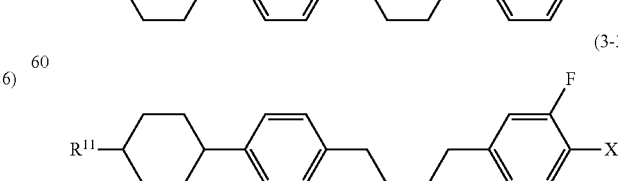

(3-37)
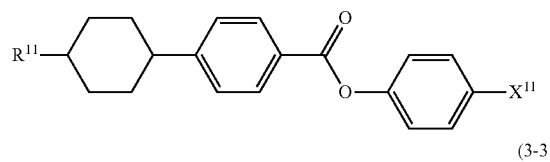
(3-38)
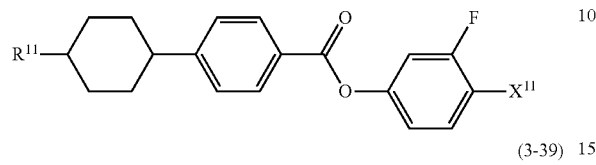
(3-39)
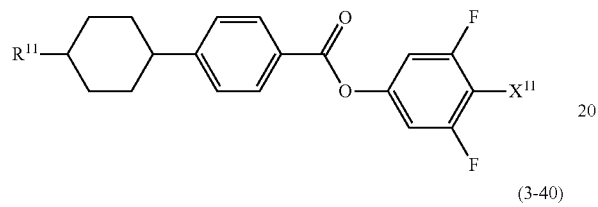
(3-40)
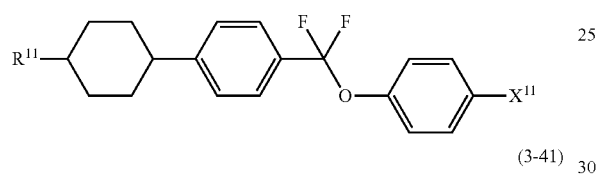
(3-41)
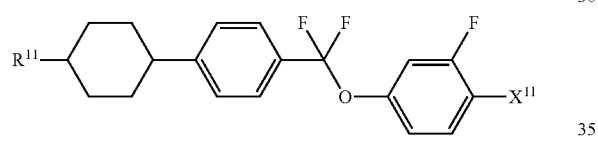
(3-42)
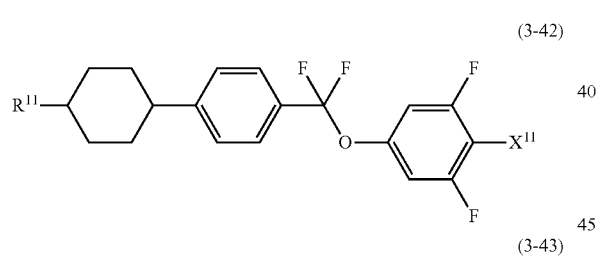
(3-43)
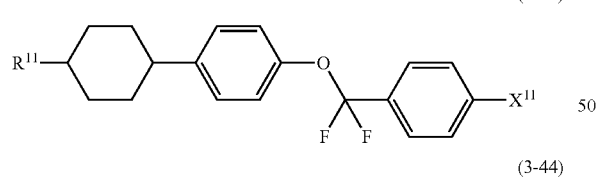
(3-44)
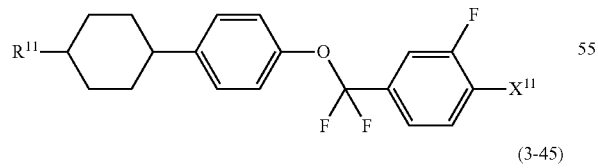
(3-45)
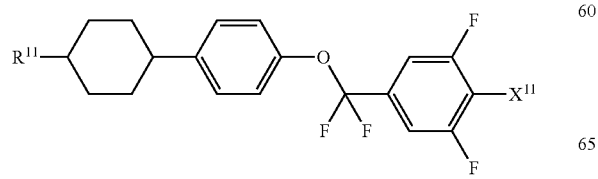
(3-46)
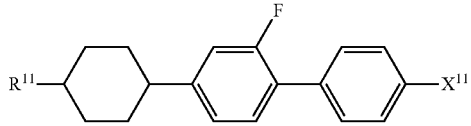
(3-47)
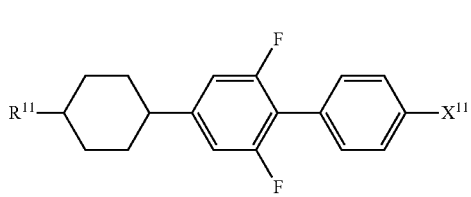
(3-48)
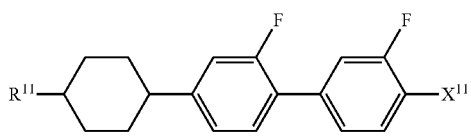
(3-49)
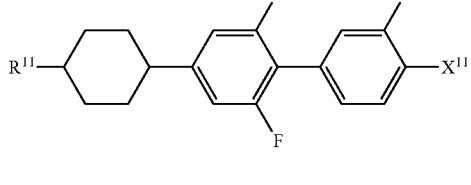
(3-50)
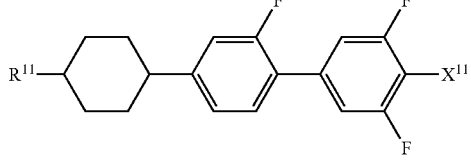
(3-51)
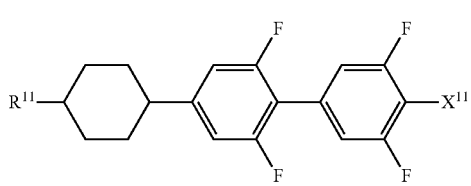
(3-52)
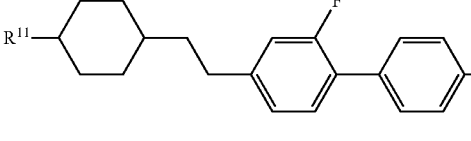
(3-53)
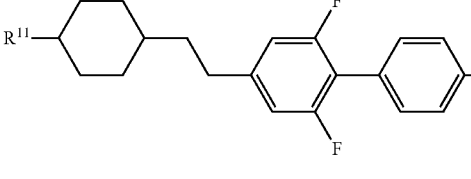
(3-54)
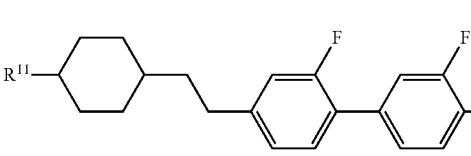

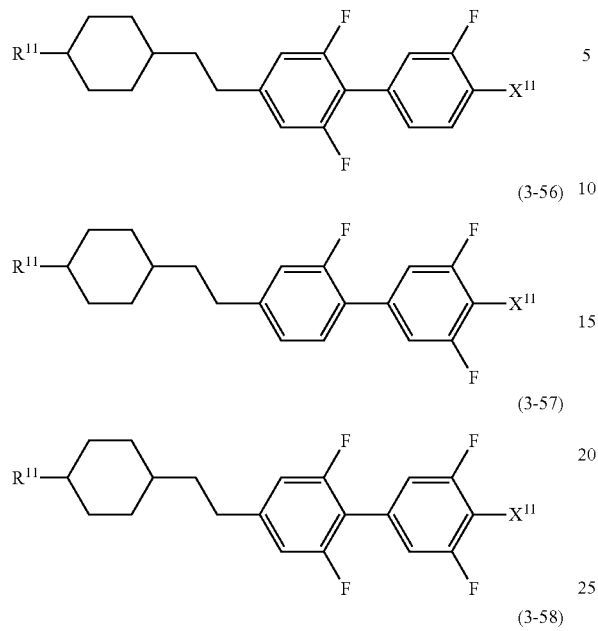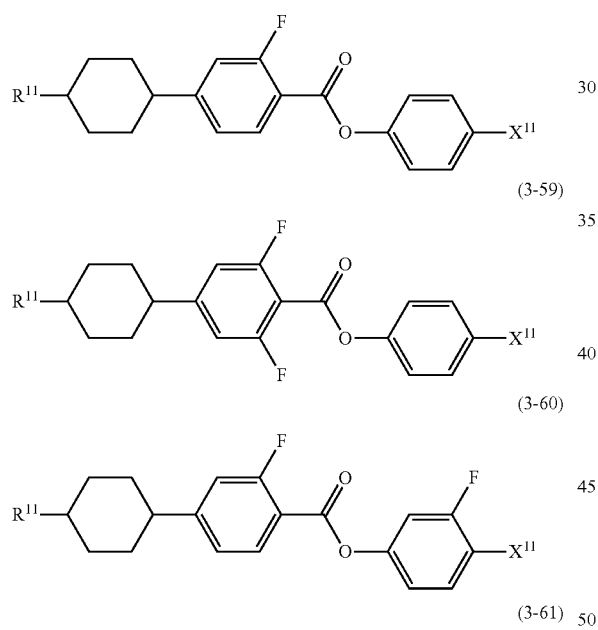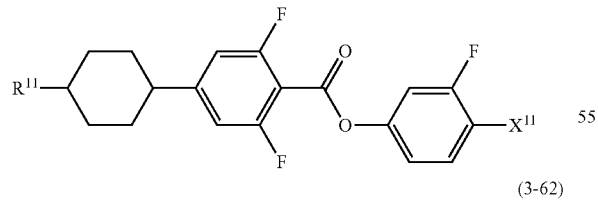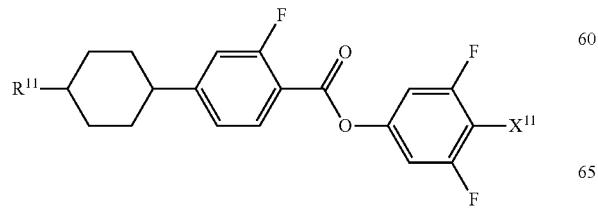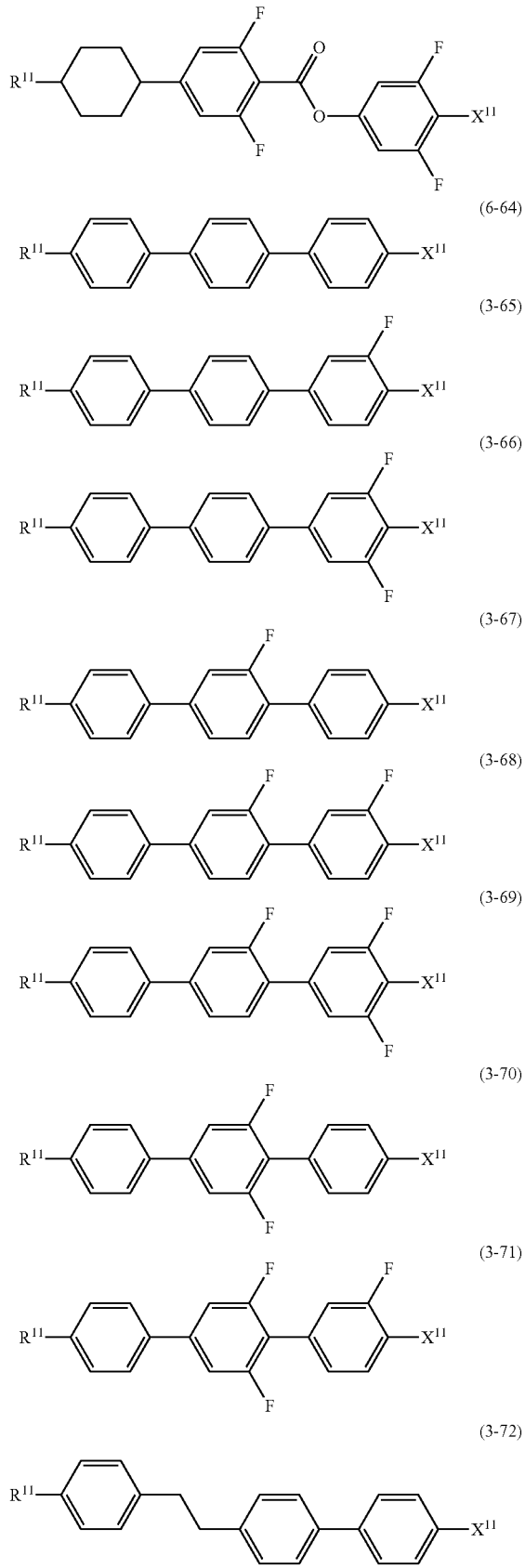

(3-73)
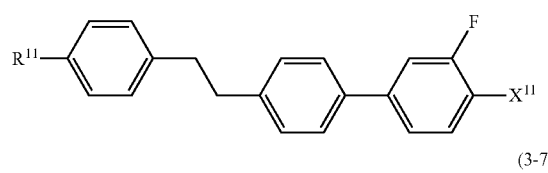
(3-74)
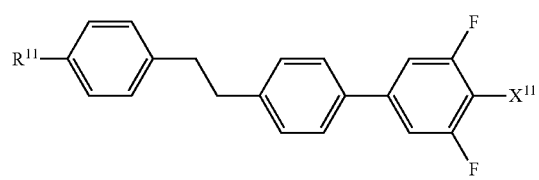
(3-75)
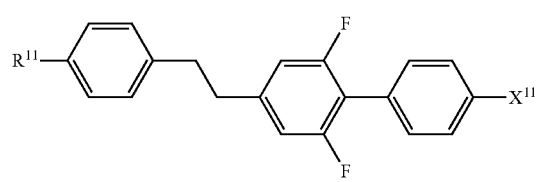
(3-76)
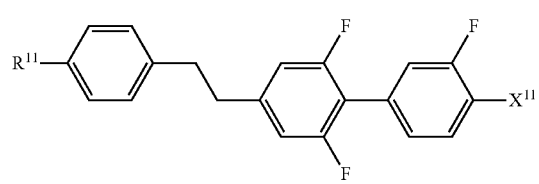
(3-77)
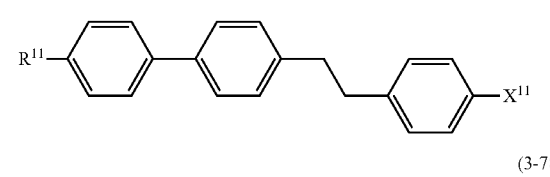
(3-78)
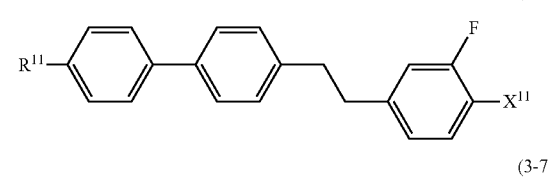
(3-79)
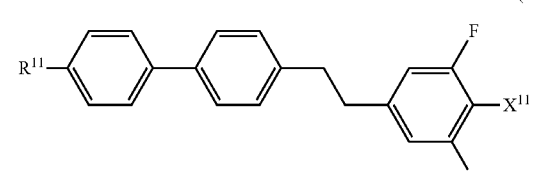
(3-80)
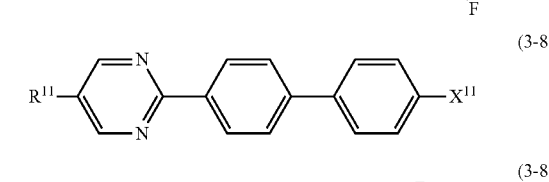
(3-81)
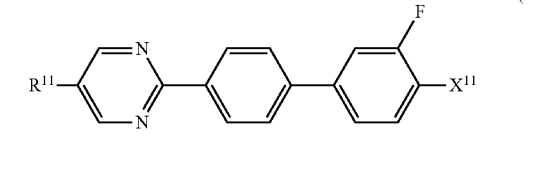
(3-82)
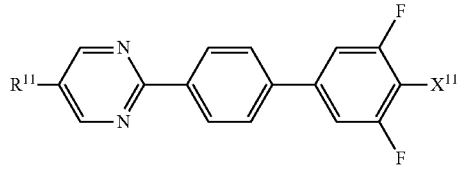
(3-83)
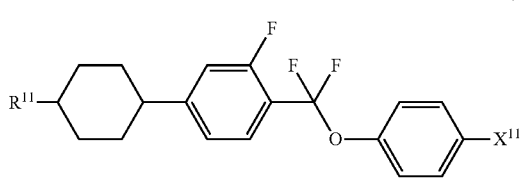
(3-84)
(3-85)
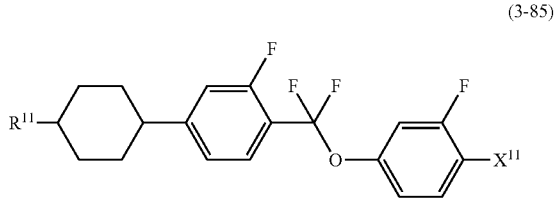
(3-86)
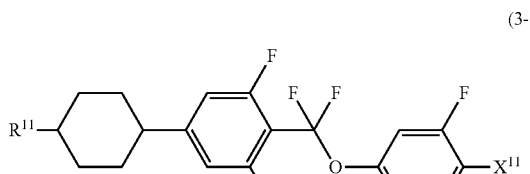
(3-87)
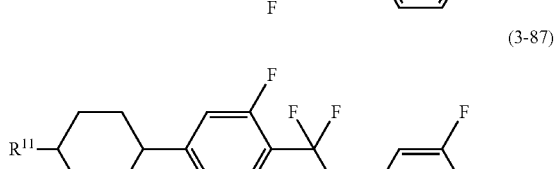
(3-88)
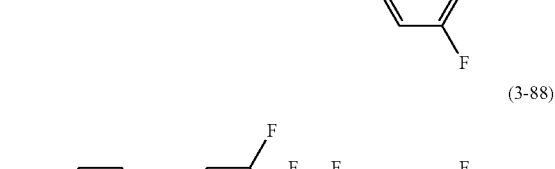
(3-89)
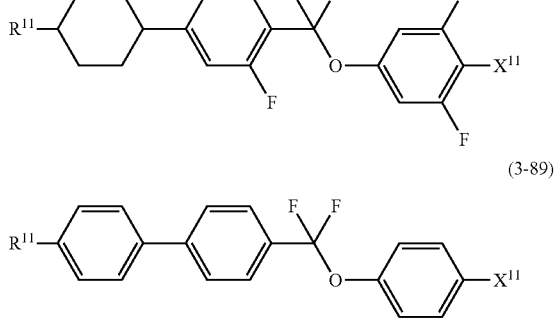

(3-90) 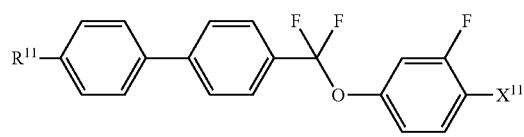
(3-91) 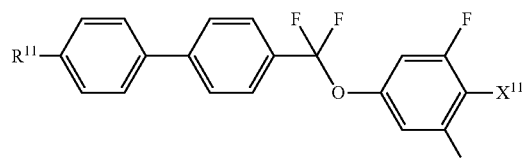
(3-92) 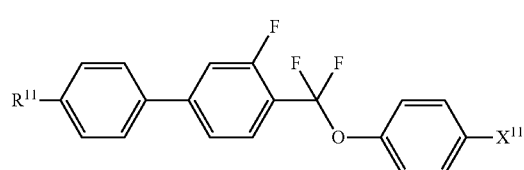
(3-93) 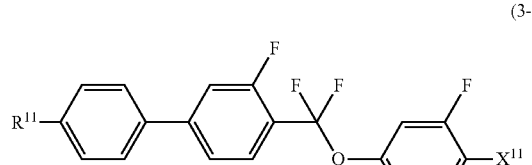
(3-94) 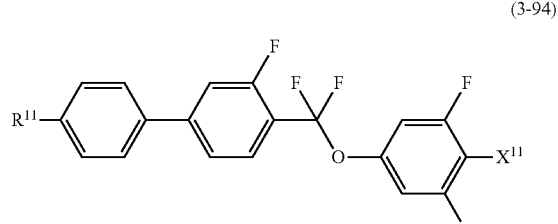
(3-95) 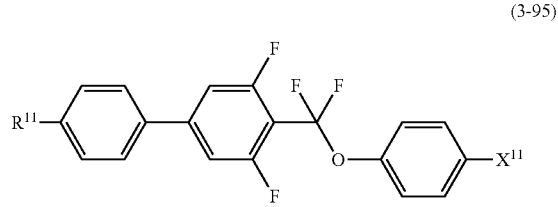
(3-96) 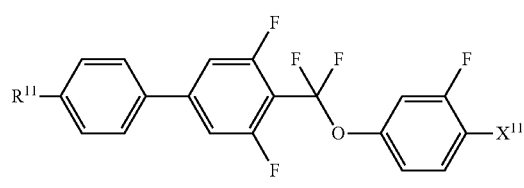
(3-97) 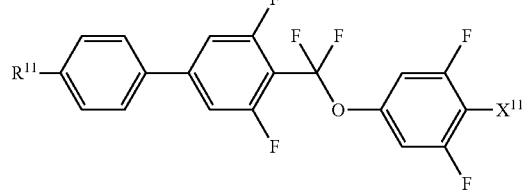
(3-98) 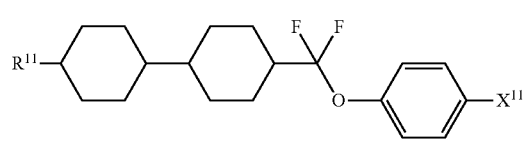
(3-99) 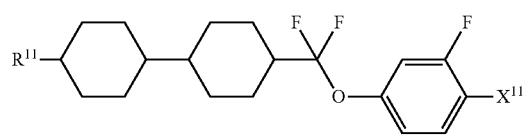
(3-100) 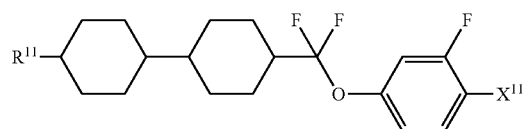
(3-101) 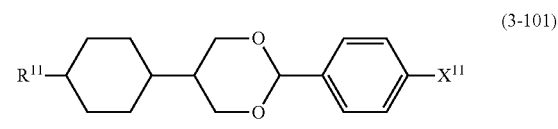
(3-102) 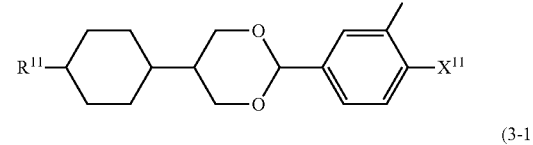
(3-103) 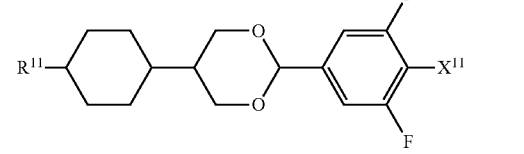
(3-104) 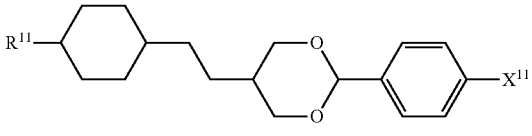
(3-105) 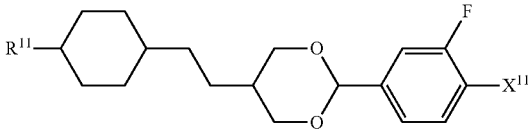
(3-106) 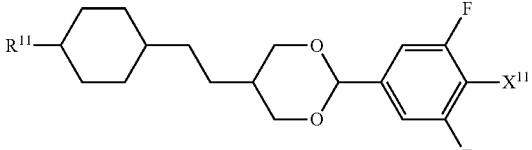
(3-107) 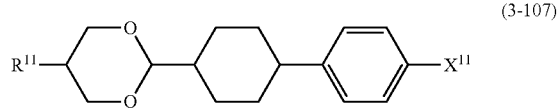

(3-108) 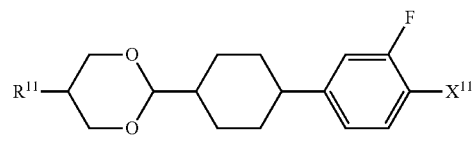
(3-109) 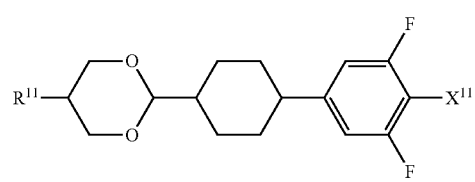
(3-110) 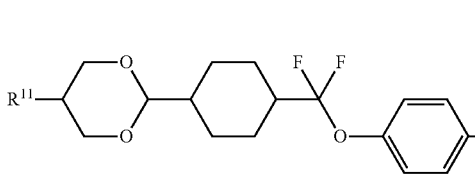
(3-111) 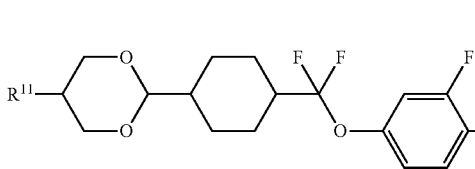
(3-112) 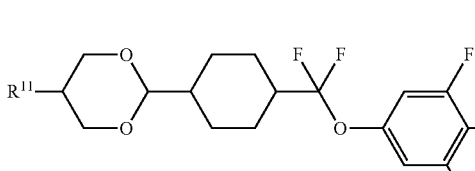
(3-113) 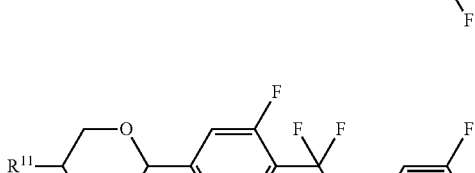
(4-1) 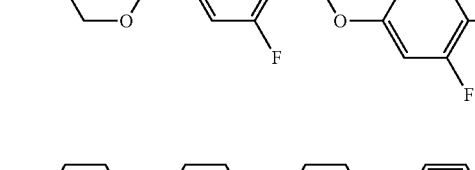
(4-2) 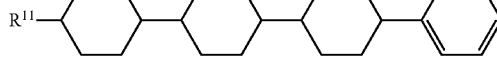
(4-3) 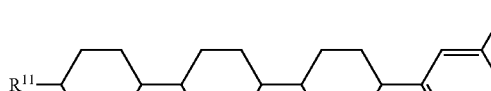
(4-4) 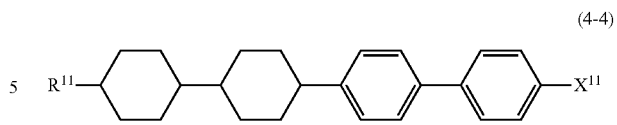
(4-5) 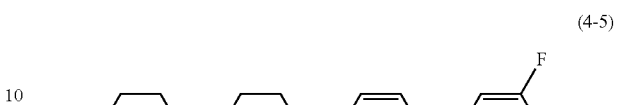
(4-6) 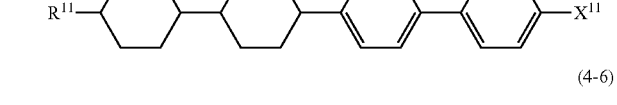
(4-7) 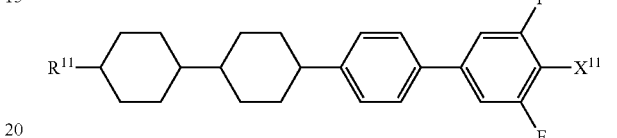
(4-8) 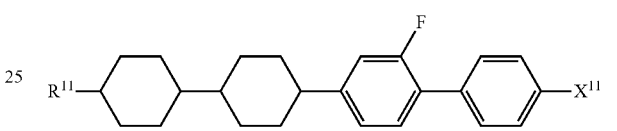
(4-9) 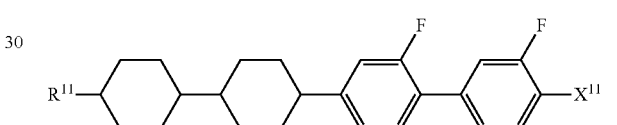
(4-10) 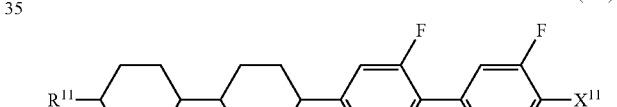
(4-11) 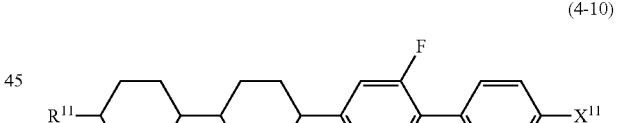
(4-12) 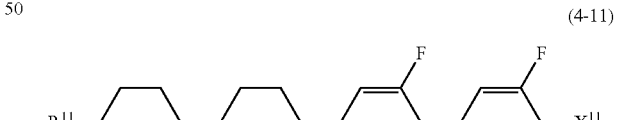

(4-13) 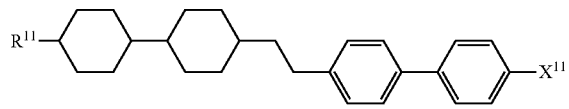
(4-14) 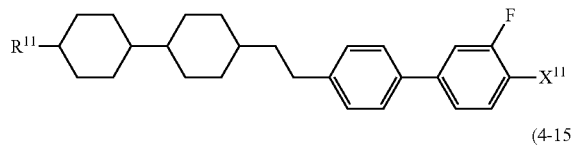
(4-15) 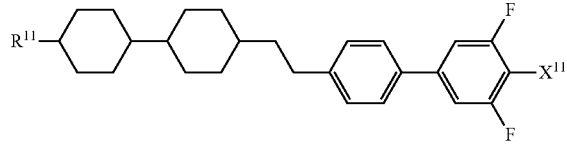
(4-16) 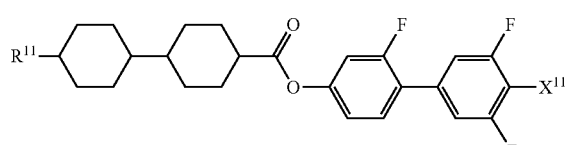
(4-17) 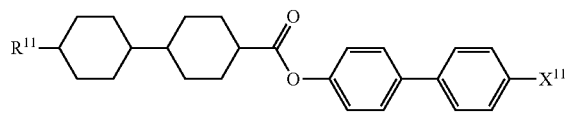
(4-18) 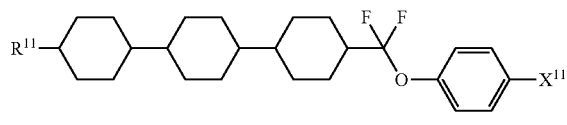
(4-19) 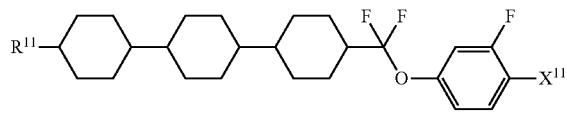
(4-20) 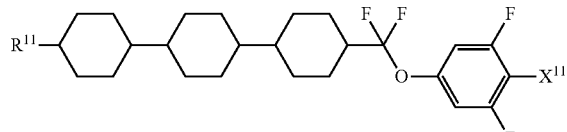
(4-21) 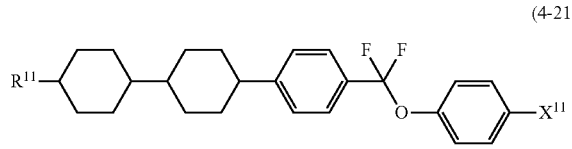
(4-22) 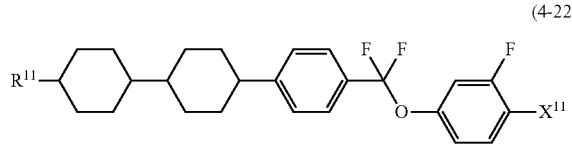
(4-23) 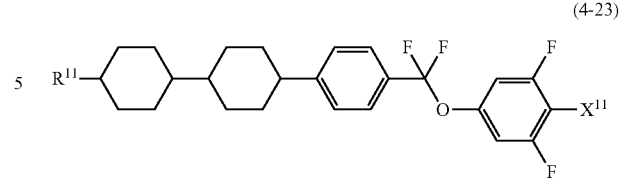
(4-24) 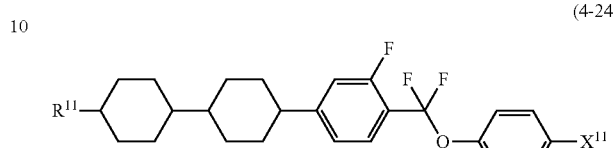
(4-25) 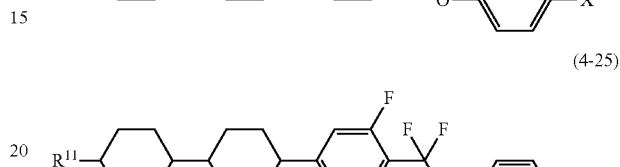
(4-26) 
(4-27) 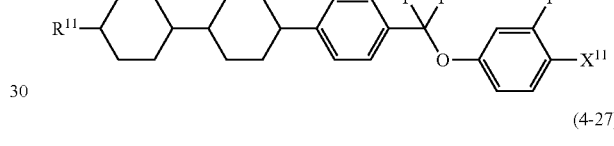
(4-28) 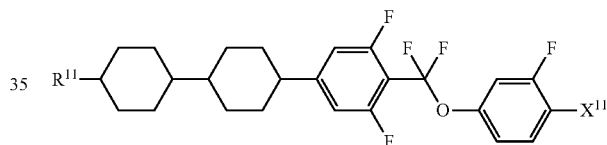
(4-29) 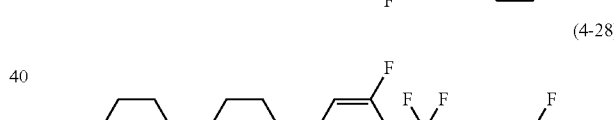
(4-30) 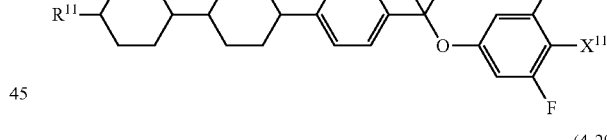
(4-31) 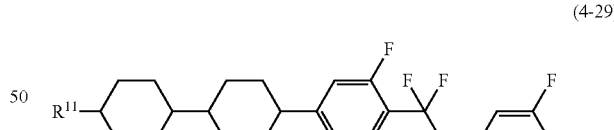

(4-48) 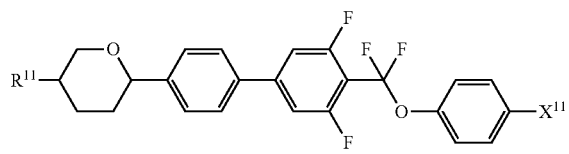

(4-49) 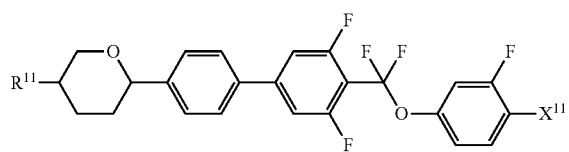

(4-50) 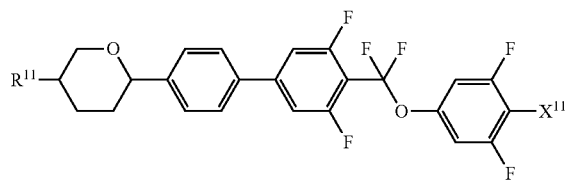

(4-51) 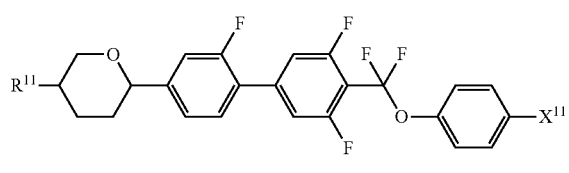

(4-52) 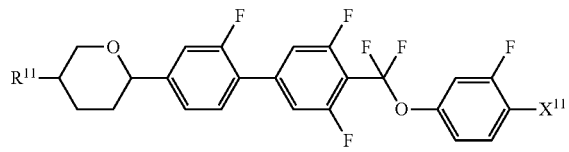

(4-53) 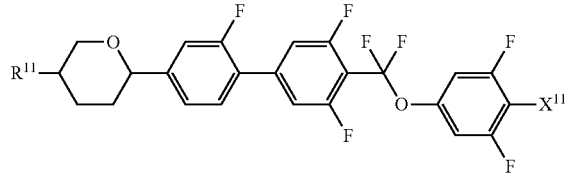

(4-54) 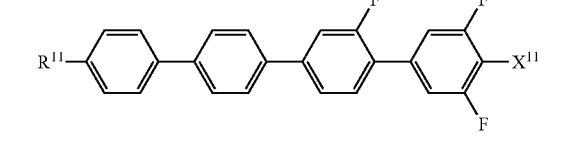

(4-55) 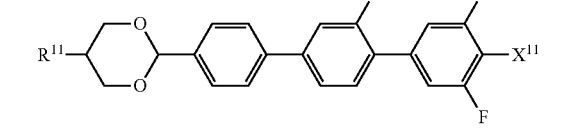

(4-56) 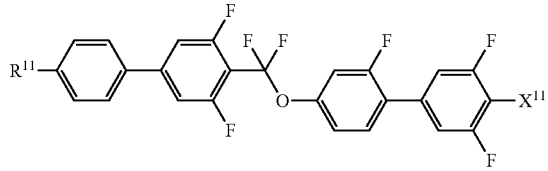

(4-57) 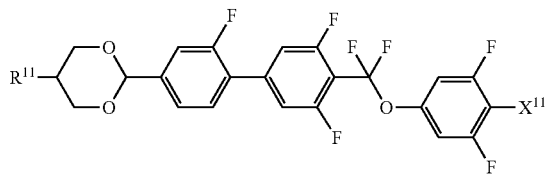

Component B is used for the preparation of a composition for modes such as IPS, FFS and OCB, since the dielectric anisotropy is positive and the stability to heat or light is quite good. The content of component B is suitably in the range of 1% by weight to 99% by weight, preferably in the range of 10% by weight to 97% by weight, more preferably in the range of 40% by weight to 95% by weight, based on the weight of the liquid crystal composition. It is desirable that the content of component B should be 30% by weight or less, when component B is added to a composition having negative dielectric anisotropy. The elastic constant of the composition can be adjusted and the voltage-transmission curve of the device can be adjusted, by the addition of component B.

Component C is compound (5) where the right-terminal group is —C≡N or —C≡C—C≡N. Desirable examples of component C include compounds (5-1) to (5-64). In these compounds, $R^{12}$ is alkyl having 1 to 10 carbons or alkenyl having 2 to 10 carbons, and in the alkyl and alkenyl at least one —CH$_2$— may be replaced by —O—, and in these groups at least one hydrogen may be replaced by fluorine. $X^{12}$ is —C≡N or —C≡C—C≡N.

(5-1) 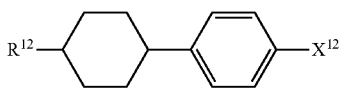

(5-2) 

(5-3) 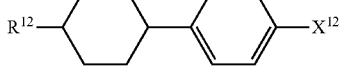

(5-4) 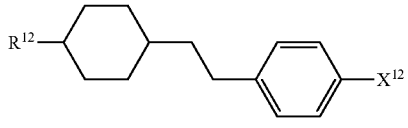

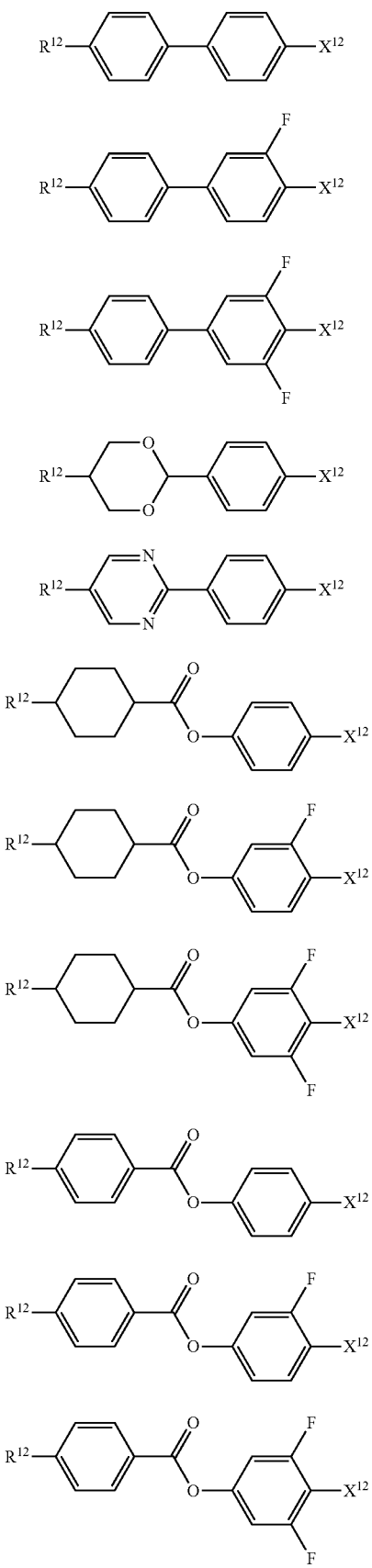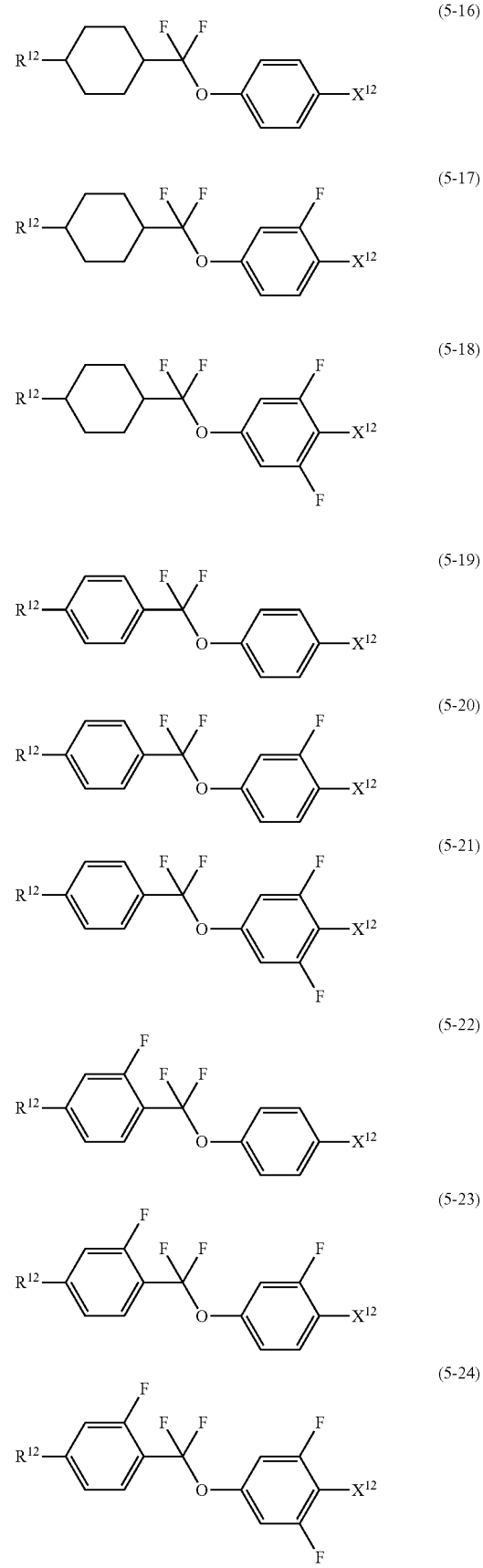

(5-25) 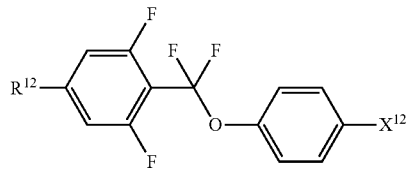
(5-26) 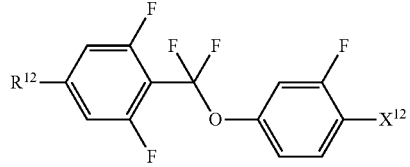
(5-27) 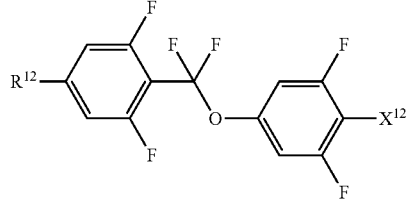
(5-28) 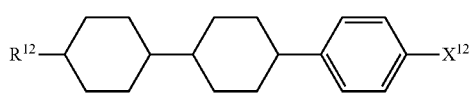
(5-29) 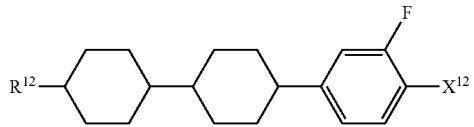
(5-30) 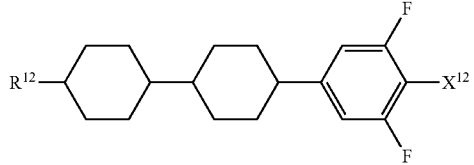
(5-31) 
(5-32) 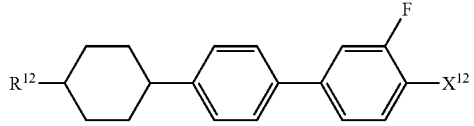
(5-33) 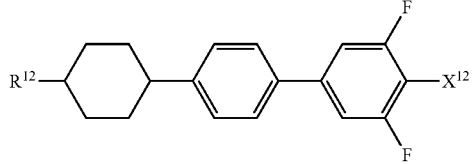
(5-34) 
(5-35) 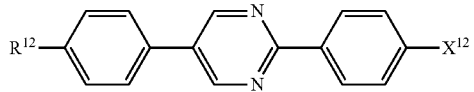
(5-36) 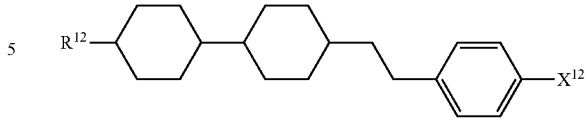
(5-37) 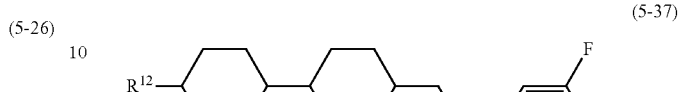
(5-38) 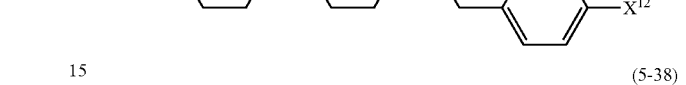
(5-39) 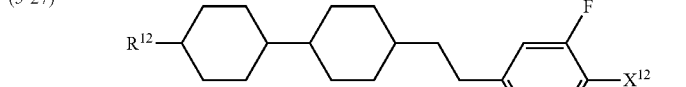
(5-40) 
(5-41) 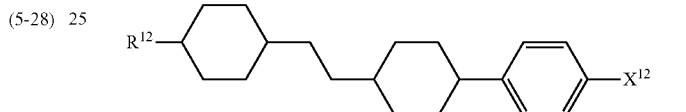
(5-42) 
(5-43) 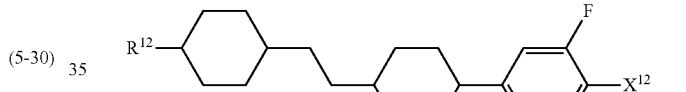
(5-44) 

(5-45)
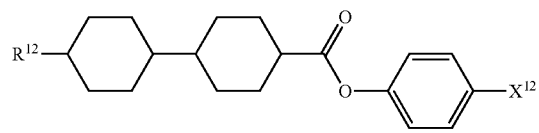
(5-46)
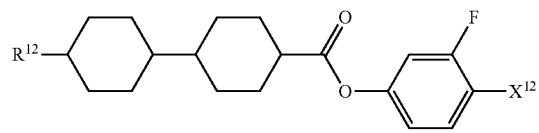
(5-47)
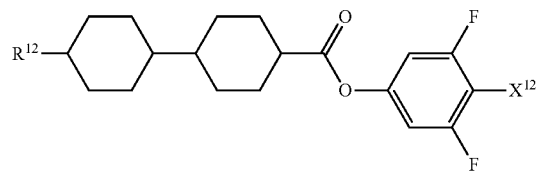
(5-48)
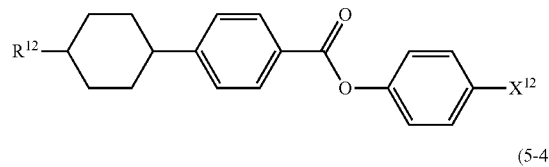
(5-49)
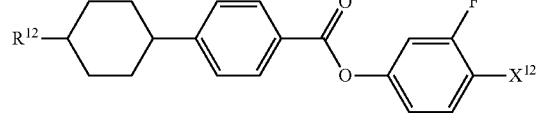
(5-50)
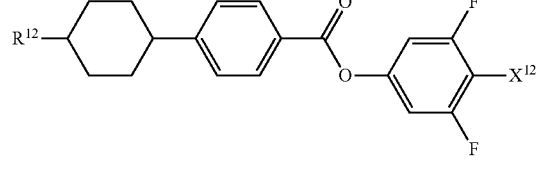
(5-51)
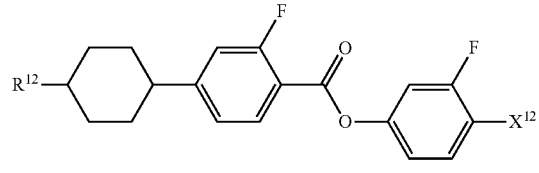
(5-52)
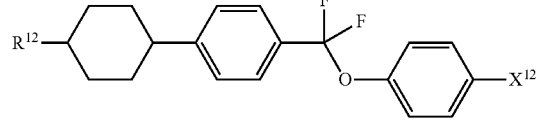
(5-53)
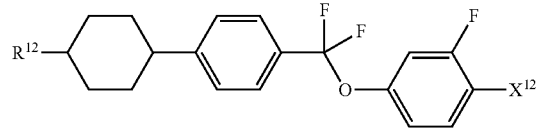
(5-54)
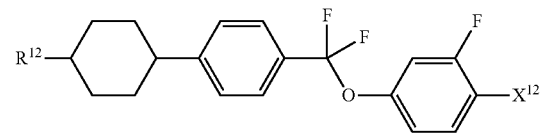
(5-55)
(5-56)
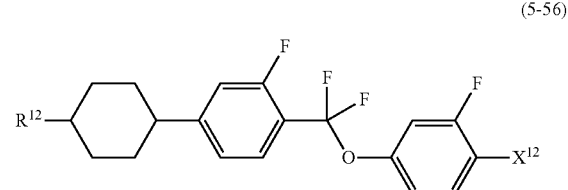
(5-57)
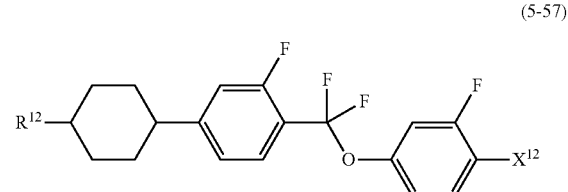
(5-58)
(5-59)
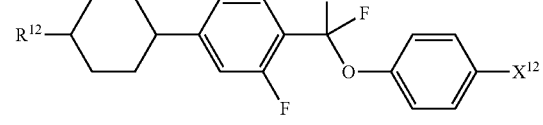
(5-60)
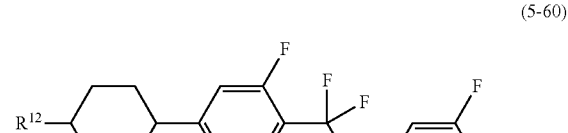
(5-61)
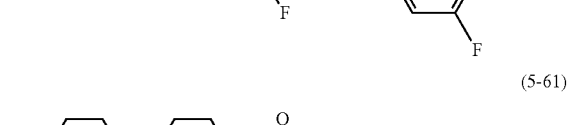

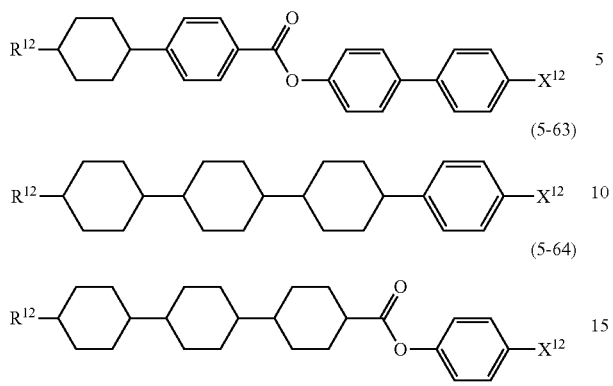

Component C is used for the preparation of a composition for modes such as TN, since the dielectric anisotropy is positive and its value is large. The dielectric anisotropy of the composition can be increased by the addition of component C. Component C has the effect of increasing the temperature range of a liquid crystal phase, adjusting the viscosity and adjusting the optical anisotropy. Component C is useful for adjusting the voltage-transmission curve of the device.

The content of component C is suitably in the range of 1% by weight to 99% by weight, preferably in the range of 10% by weight to 97% by weight, more preferably 40% by weight to 95% by weight based on the weight of the liquid crystal composition, in the preparation of a composition for modes such as TN. The content of component C is preferably 30% by weight or less, when component C is added to a composition having negative dielectric anisotropy. The elastic constant of the composition can be adjusted and the voltage-transmission curve of the device can be adjusted, by the addition of component C.

Component D is compounds (6) to (12). These compounds have two-halogen-substituted phenylene in the lateral position, such as 2,3-difluoro-1,4-phenylene. Desirable examples of component D include compounds (6-1) to (6-8), compounds (7-1) to (7-17), compound (8-1), compounds (9-1) to (9-3), compounds (10-1) to (10-11), compounds (11-1) to (11-3) and compounds (12-1) to (12-3). In these compounds, $R^{13}$, $R^{14}$ and $R^{15}$ are independently alkyl having 1 to 10 carbons or alkenyl having 2 to 10 carbons, and in the alkyl and alkenyl at least one —$CH_2$— may be replaced by —O—, and in these groups at least one hydrogen may be replaced by fluorine, and $R^{15}$ may also be hydrogen or fluorine.

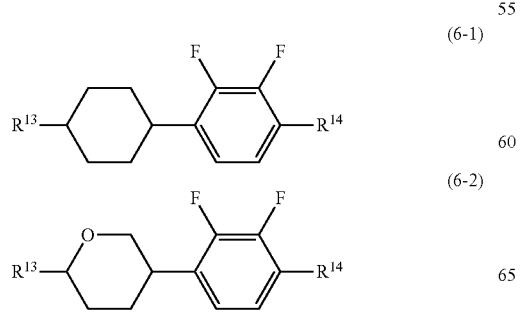

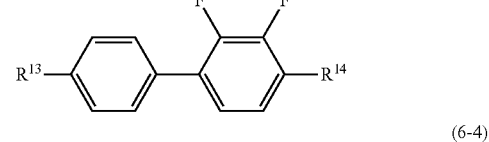
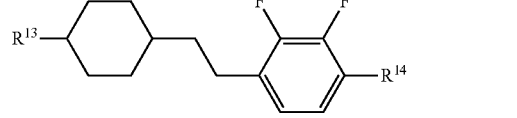
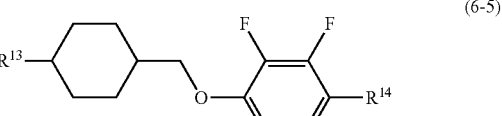
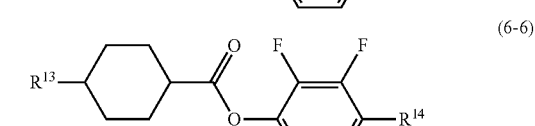
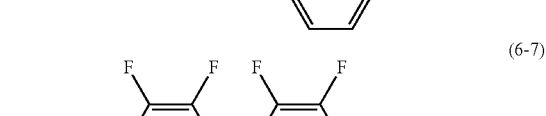

(7-6) 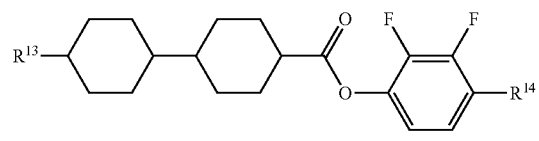
(7-7) 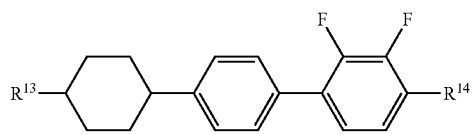
(7-8) 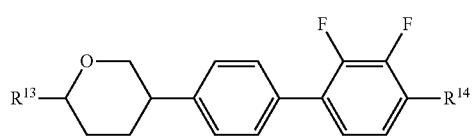
(7-9) 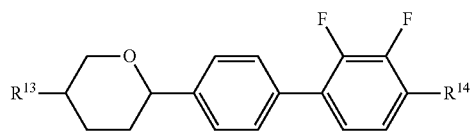
(7-10) 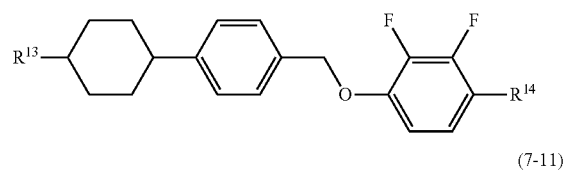
(7-11) 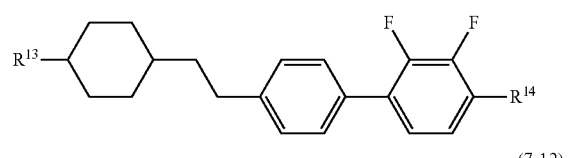
(7-12) 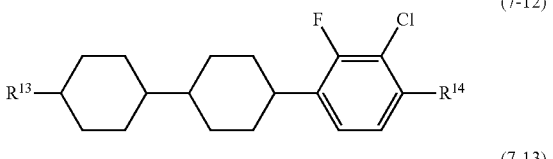
(7-13) 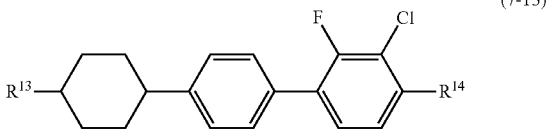
(7-14) 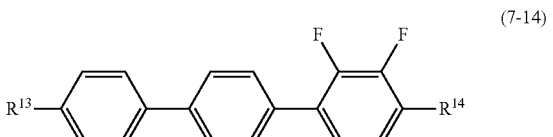
(7-15) 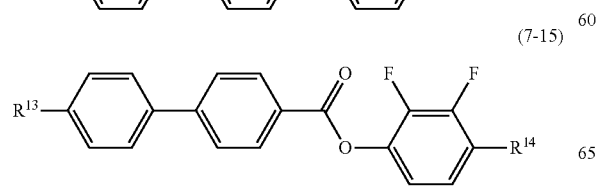
(7-16) 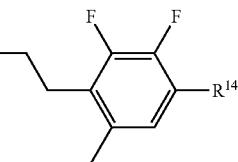
(7-17) 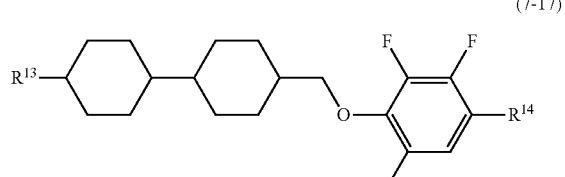
(8-1) 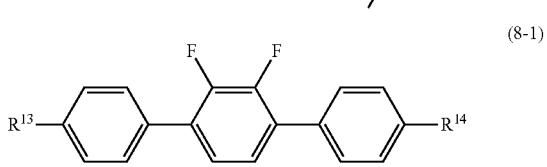
(9-1) 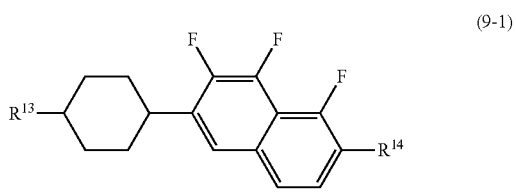
(9-2) 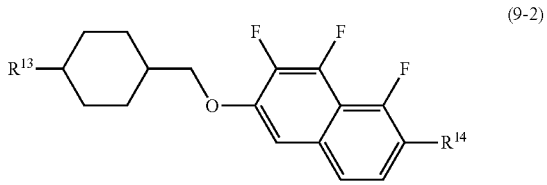
(9-3) 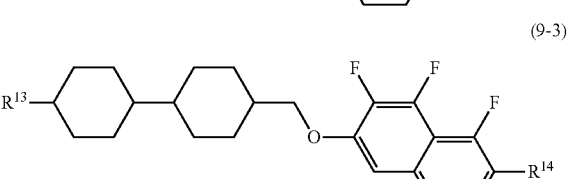
(10-1) 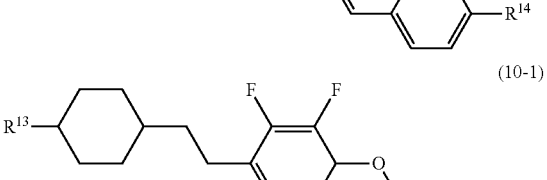
(10-2) 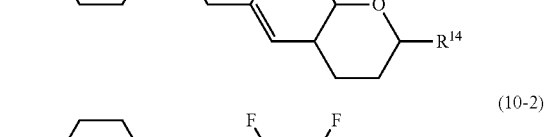
(10-3) 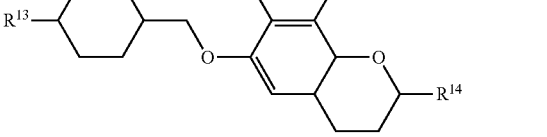

(10-4)
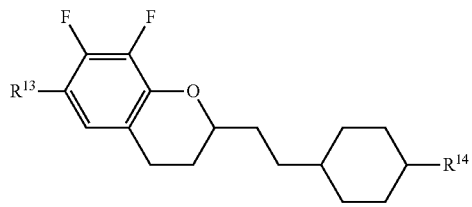

(10-5)
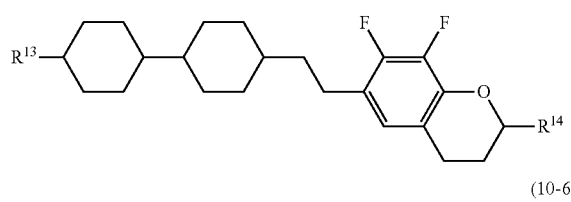

(10-6)
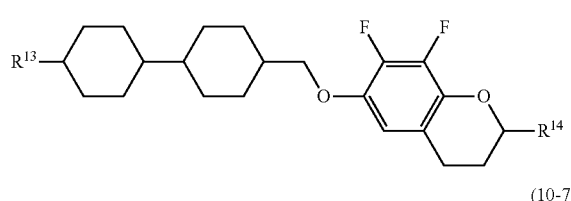

(10-7)
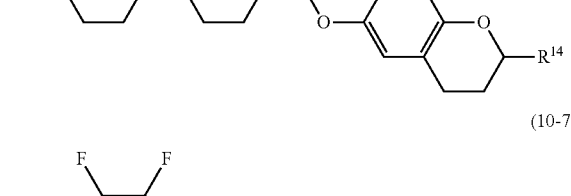

(10-8)
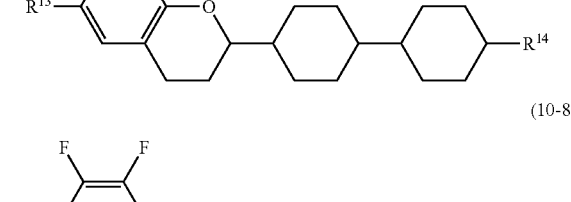

(10-9)
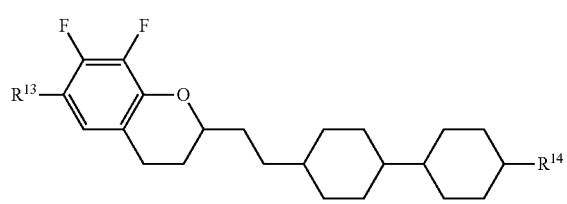

(10-10)
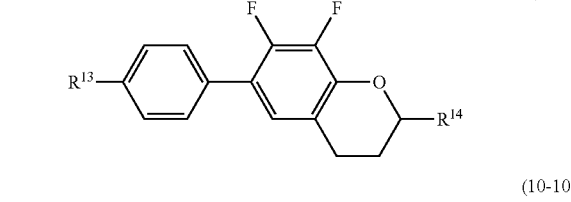

(10-11)
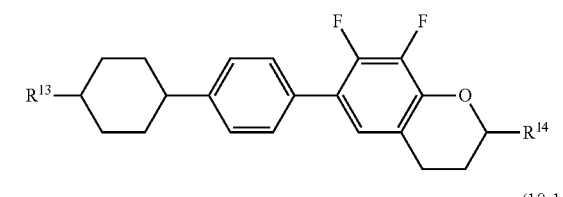

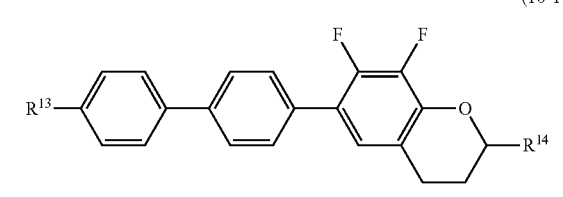

(11-1)
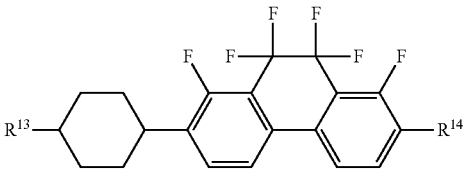

(11-2)
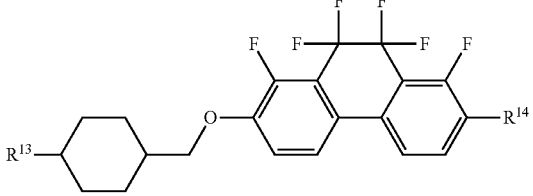

(11-3)
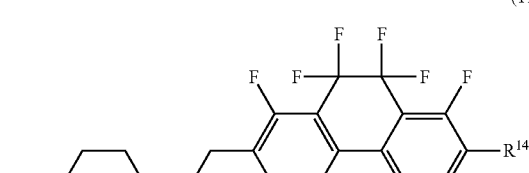

(12-1)
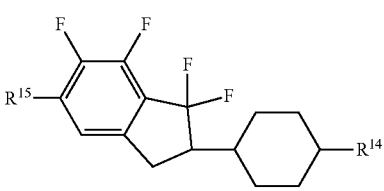

(12-2)
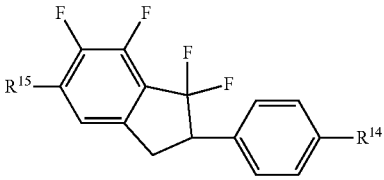

(12-3)
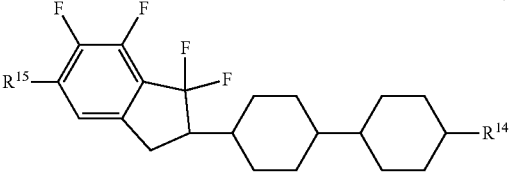

Component D has a large negative dielectric anisotropy. Component D is used for the preparation of a composition for modes such as IPS, VA and PSA. As the content of component D is increased, the dielectric anisotropy of the composition increases negatively. However, the viscosity increases. Thus, it is desirable that the content should be decreased as long as the required value of the threshold voltage of the device is satisfied. The content is preferably 40% by weight or more in order to ensure adequate voltage drive, in consideration that the value of the dielectric anisotropy is about −5.

In component D, compound (6) is effective in decreasing the viscosity, adjusting the optical anisotropy or increasing the dielectric anisotropy, since it is a two-ring compound. Compounds (7) and (8) are efftive in increasing the maximum temperature, increasing the optical anisotropy or increasing the dielectric anisotropy, since it is a three-ring compound. Compounds (9) to (12) are effective in increasing the dielectric anisotropy.

The content of component D is preferably 40% by weight or more, more preferably in the range of 50% by weight to 95% by weight based on the weight of the liquid crystal composition, in the preparation of a composition for modes such as IPS, VA and PSA. It is desirable that the content of component D should be 30% by weight or less when component D is added to a composition having positive dielectric anisotropy. The elastic constant of the composition can be adjusted and the voltage-transmission curve of the device can be adjusted by the addition of component D.

Component E is a compound where two terminal groups are alkyl or the like. Desirable examples of component E include compounds (13-1) to (13-11), compounds (14-1) to (14-19) and compounds (15-1) to (15-7). In these compounds, $R^{16}$ and $R^{17}$ are independently alkyl having 1 to 10 carbons or alkenyl having 2 to 10 carbons, and in the alkyl and alkenyl at least one —$CH_2$— may be replaced by —O—, and in these groups at least one hydrogen may be replaced by fluorine.

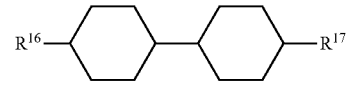 (13-1)

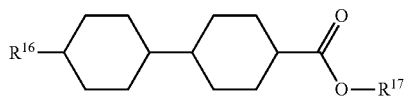 (13-2)

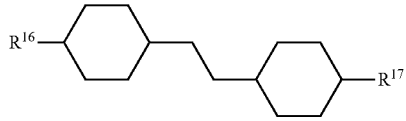 (13-3)

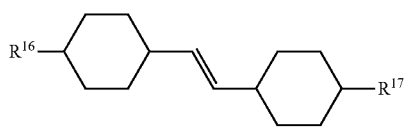 (13-4)

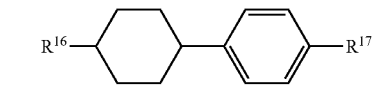 (13-5)

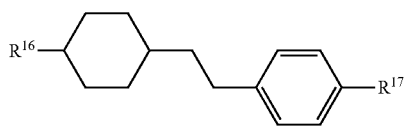 (13-6)

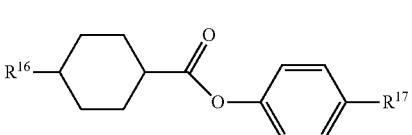 (13-7)

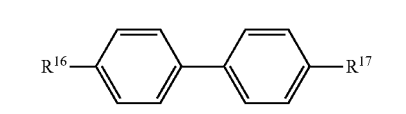 (13-8)

-continued

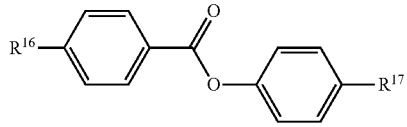 (13-9)

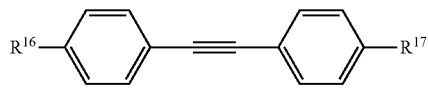 (13-10)

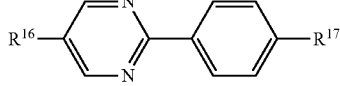 (13-11)

 (14-1)

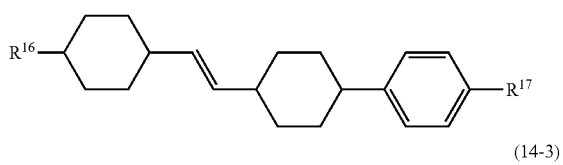 (14-2)

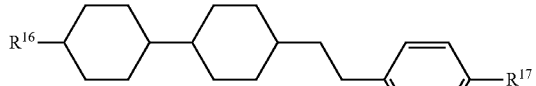 (14-3)

 (14-4)

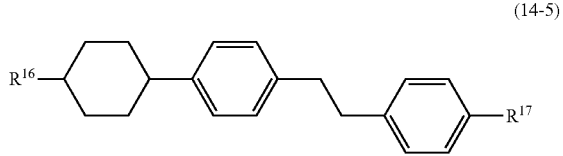 (14-5)

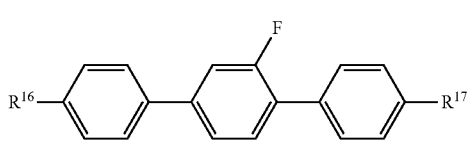 (14-6)

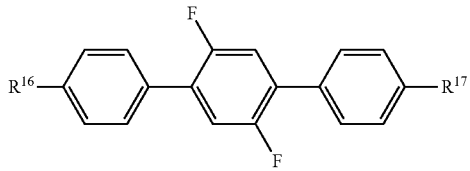 (14-7)

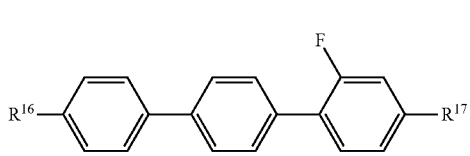 (14-8)

(14-9) 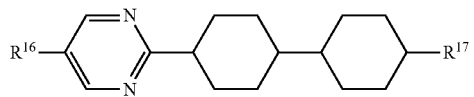

(14-10) 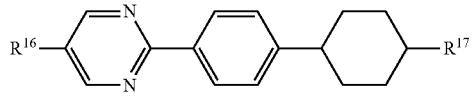

(14-11) 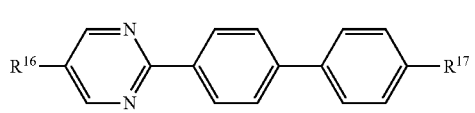

(14-12) 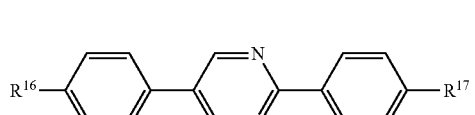

(14-13) 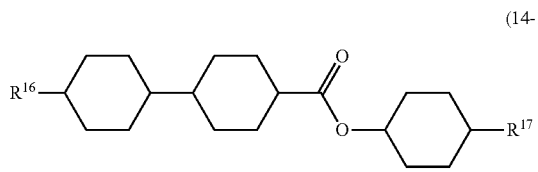

(14-14) 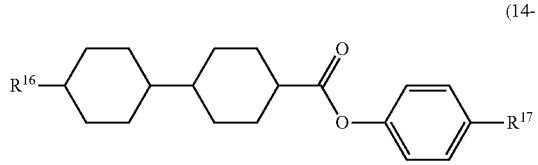

(14-15) 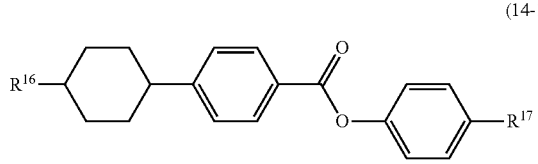

(14-16) 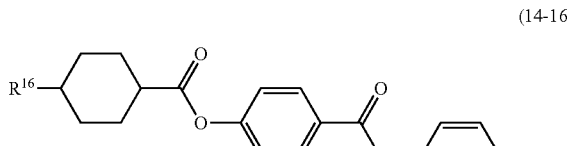

(14-17) 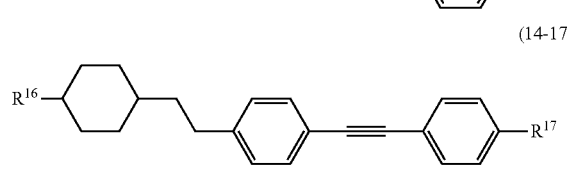

(14-18) 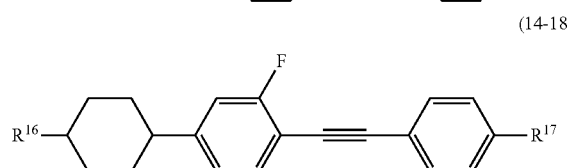

(14-19) 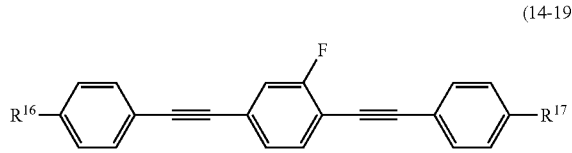

(15-1) 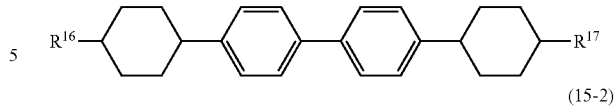

(15-2) 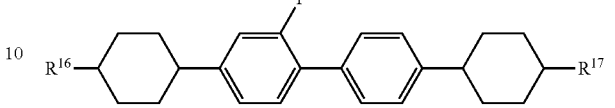

(15-3) 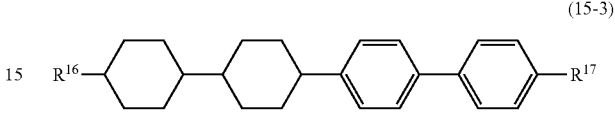

(15-4) 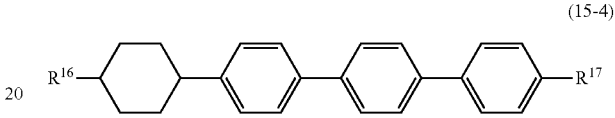

(15-5) 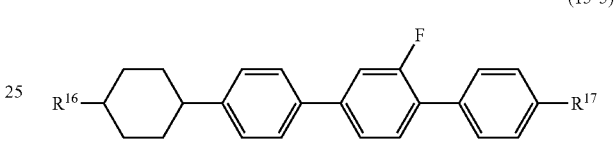

(15-6) 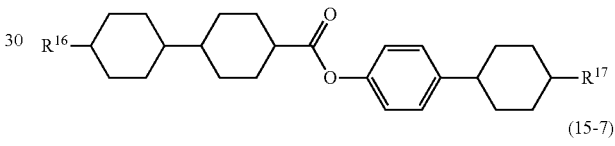

(15-7) 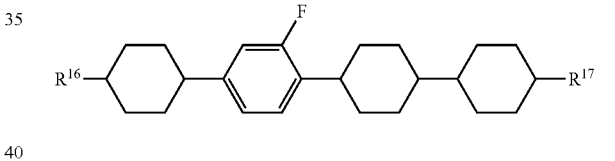

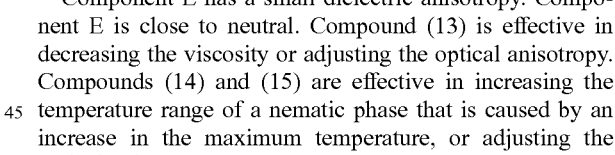

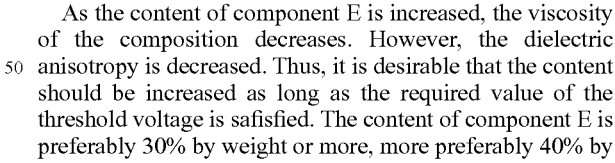

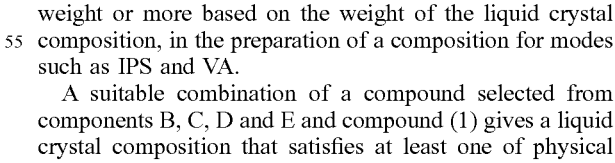

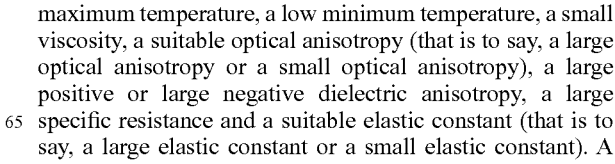

Component E has a small dielectric anisotropy. Component E is close to neutral. Compound (13) is effective in decreasing the viscosity or adjusting the optical anisotropy. Compounds (14) and (15) are effective in increasing the temperature range of a nematic phase that is caused by an increase in the maximum temperature, or adjusting the optical anisotropy.

As the content of component E is increased, the viscosity of the composition decreases. However, the dielectric anisotropy is decreased. Thus, it is desirable that the content should be increased as long as the required value of the threshold voltage is satisfied. The content of component E is preferably 30% by weight or more, more preferably 40% by weight or more based on the weight of the liquid crystal composition, in the preparation of a composition for modes such as IPS and VA.

A suitable combination of a compound selected from components B, C, D and E and compound (1) gives a liquid crystal composition that satisfies at least one of physical properties such as a high stability to heat or light, a high maximum temperature, a low minimum temperature, a small viscosity, a suitable optical anisotropy (that is to say, a large optical anisotropy or a small optical anisotropy), a large positive or large negative dielectric anisotropy, a large specific resistance and a suitable elastic constant (that is to say, a large elastic constant or a small elastic constant). A device containing such a composition has a wide temperature range in which the device can be used, a short response time, a large voltage holding ratio, a low threshold voltage, a large contrast ratio, a small flicker rate and a long service life.

A flicker is sometimes generated on a display screen, when a device is used for a long time. The flicker rate (%) is expressed by [|(brightness when positive voltage is applied)−(brightness when negative voltage is applied)|]/average brightness×100. In a device in which the flicker rate is in the range of 0% to 1%, the flicker is not easily generated on the display screen, even when the device is used for a long time. The flicker relates to image burn-in, and it is estimated that the flicker is caused by the potential difference between the positive and negative frames, when the device is driven by an alternating current. A composition including compound (1) is useful for decreasing the generation of the flicker.

3-2. Additives

The liquid crystal composition is prepared according to known methods. For example, component compounds are mixed and dissolved in each other by heating. An additive may be added to the composition depending on its intended use. Examples of the additive include a polymerizable compound, a polymerization initiator, a polymerization inhibitor, an optically active compound, an antioxidant, an ultraviolet light absorber, a light stabilizer, a thermal stabilizer, a coloring matter and an antifoaming agent. Such an additive is well-known to a person skilled in the art, and is described in the literature.

In a liquid crystal display device having a PSA (polymer sustained alignment) mode, the composition includes a polymer. A polymerizable compound is added to the composition in order to form a polymer in it. First, a composition to which a small amount of polymerizable compound has been added is poured into a device. Next, the composition is irradiated with ultraviolet light, while a voltage is applied between the substrates of this device. The polymerizable compound is polymerized to give a network structure of a polymer in the composition. In this composition, the polymer makes it possible to adjust the alignment of liquid crystal molecules, and thus the response time of the device is decreased and image burn-in is improved.

Desirable examples of the polymerizable compound include acrylates, methacrylates, vinyl compounds, vinyloxy compounds, propenyl ethers, epoxy compounds (oxiranes, oxetanes) and vinyl ketones. More desirable examples are a compound having at least one acryloyloxy and a compound having at least one metacryloyloxy. More desirable examples also include a compound having both acryloyloxy and metacryloyloxy.

More desirable examples are compounds (M-1) to (M-18). In these compounds, $R^{25}$ to $R^{31}$ are independently hydrogen or methyl; $R^{32}$, $R^{33}$ and $R^{34}$ are independently hydrogen or alkyl having 1 to 5 carbons, and at least one of $R^{32}$, $R^{33}$ and $R^{34}$ is alkyl having 1 to 5 carbons; v, w and x are independently 0 or 1; u and y are independently an integer from 1 to 10. $L^{21}$ to $L^{26}$ are independently hydrogen or fluorine; and $L^{27}$ and $L^{28}$ are independently hydrogen, fluorine or methyl.

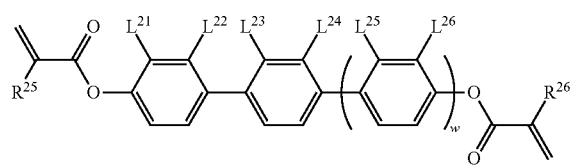

(M-1)

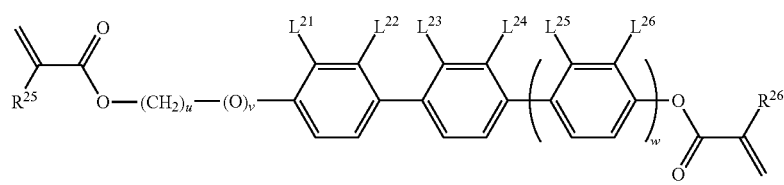

(M-2)

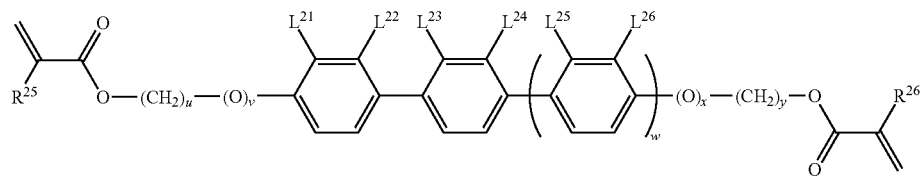

(M-3)

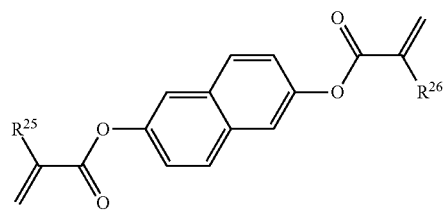

(M-4)

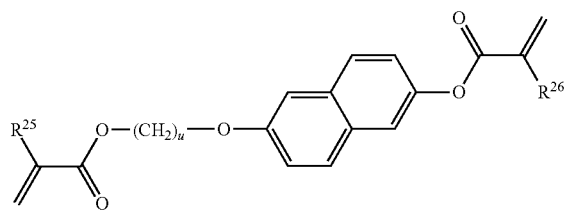

(M-5)

-continued
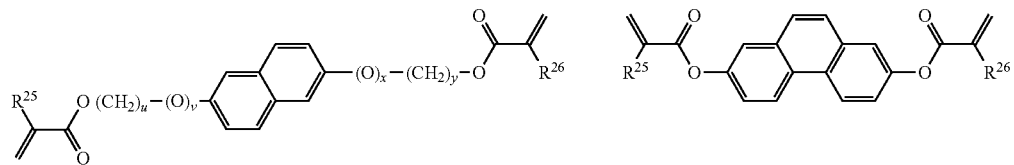 (M-6)
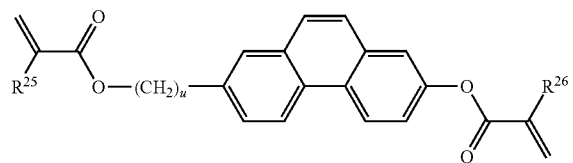 (M-7)
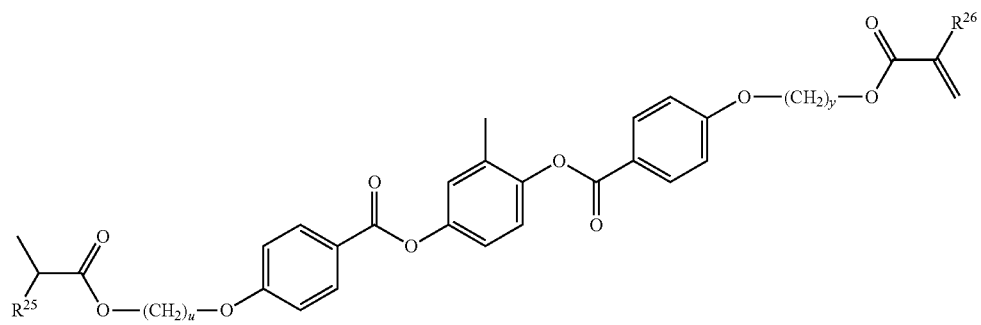 (M-8)
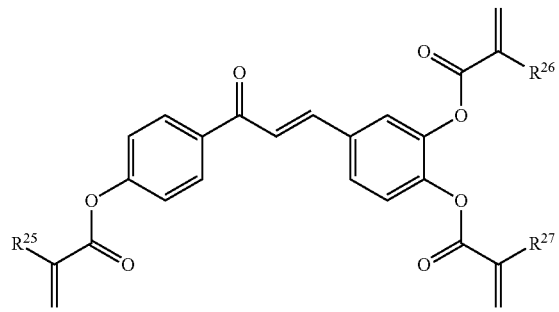 (M-9)
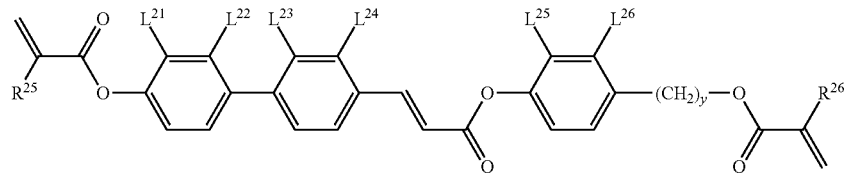 (M-10)
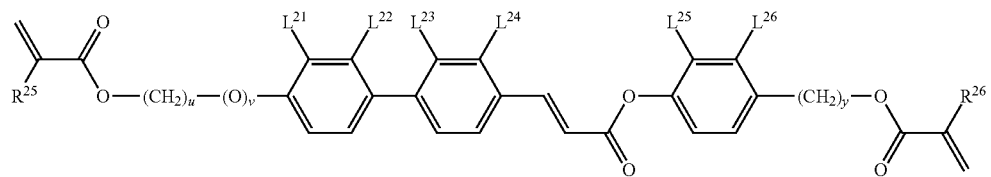 (M-11)
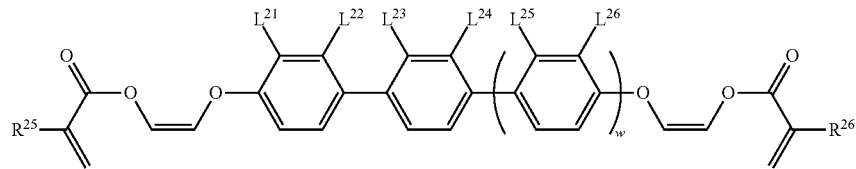 (M-12)
(M-13)

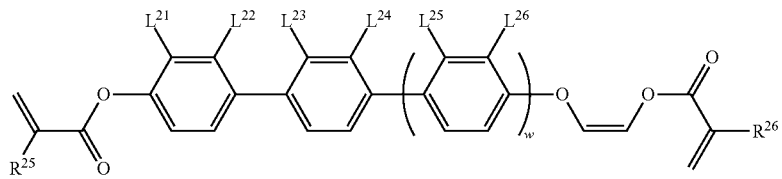

(M-14)

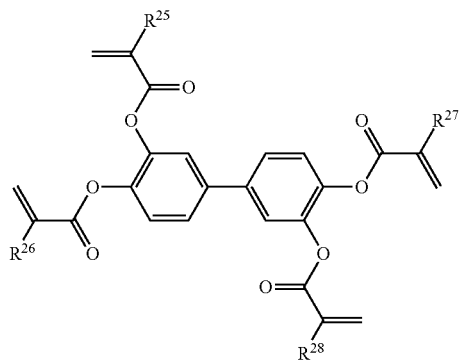

(M-15)

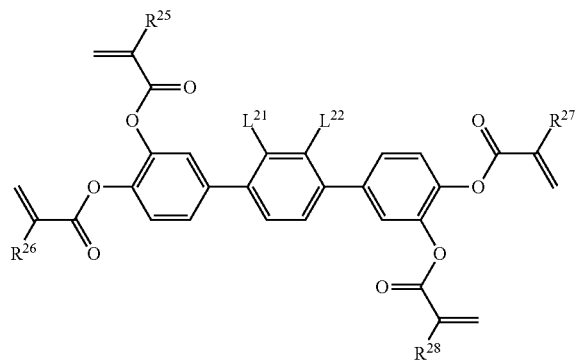

(M-16)

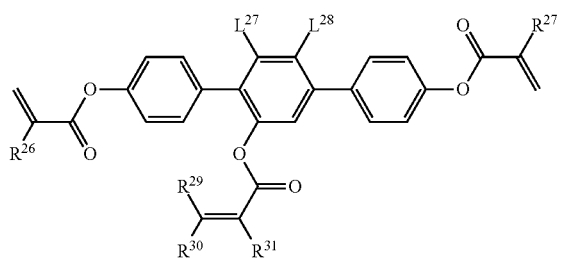

(M-17)

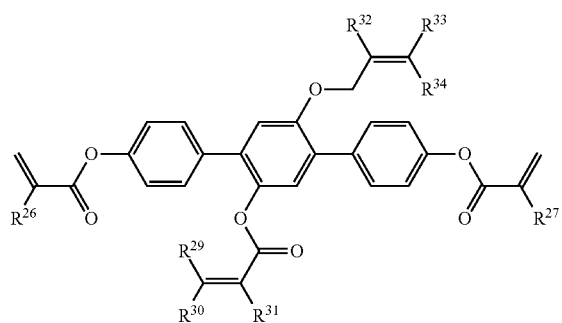

(M-18)

The polymerizable compound can be rapidly polymerized by the addition of a polymerization initiator. The remaining amount of the polymerizable compound can be decreased by optimizing the reaction conditions. Examples of a photo-radical polymerization initiator are TPO, 1173 and 4265 of Darocure series, and 184, 369, 500, 651, 784, 819, 907, 1300, 1700, 1800, 1850 and 2959 of Irgacure series, at BASF SE.

Additional examples of the photo-radical polymerization initiators are 4-methoxyphenyl-2,4-bis(trichloromethyl)triazine, 2-(4-butoxystyryl)-5-trichloromethyl-1,3,4-oxadiazole, 9-phenylacridine, 9,10-benzphenazine, a mixture of benzophenone/Michler's ketone, a mixture of hexaarylbiimidazole/mercaptobenzimidazole, 1-(4-isopropylphenyl)-2-hydroxy-2-methylpropan-1-one, benzyldimethylketal, 2-methyl-1-[4-(methylthio)phenyl]-2-morphorinopropan-1-one, a mixture of 2,4-diethylxanthone/methyl p-dimethyl-aminobenzoate and a mixture of benzophenone/methyltri-ethanolamine.

The polymerization can be carried out by irradiation with ultraviolet light under the conditions of an applied electric field, after a photo-radical polymerization initiator had been added to a liquid crystal composition. However, the unreacted polymerization initiator or the degradation product of the polymerization initiator may cause a poor display such as image burn-in to the device. The photo-polymerization may be carried out without the polymerization initiator in order to avoid it. Desirable wavelengths of the irradiated light are in the range of 150 nm to 500 nm. More desirable wavelengths are in the range of 250 nm to 450 nm, and the most desirable wavelengths are in the range of 300 nm to 400 nm.

A polymerization inhibitor may be added in order to prevent the polymerization, when a polymerizable compound is kept in storage. The polymerizable compound is usually added to a composition without removing the polymerization inhibitor. Examples of the polymerization inhibitor include hydroquinone derivatives such as hydroquinone and methylhydroquinone, 4-t-butylcatechol, 4-methoxyphenol and phenothiazine.

An optically active compound is effective in inducing a helical structure in liquid crystal molecules, giving a necessary twist angle and thus preventing a reverse twist. A helical pitch can be adjusted by the addition of the optically active compound. Two or more optically active compounds may be added for the purpose of adjusting the temperature dependence of the helical pitch. Desirable examples of the optically active compound include the following compounds (Op-1) to (Op-18). In compound (Op-18), ring J is 1,4-cyclohexylene or 1,4-phenylene, and $R^{28}$ is alkyl having 1 to 10 carbons. An asterisk indicates an asymmetric carbon.

(Op-1)
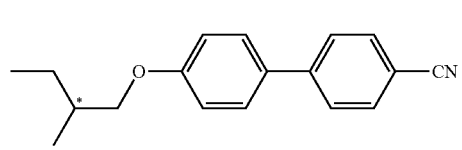
(Op-2)
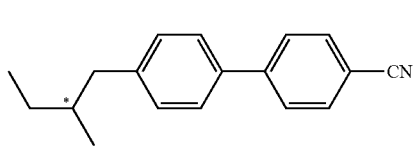
(Op-3)
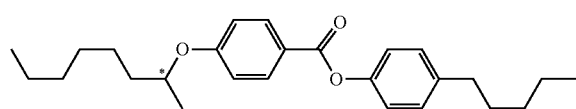
(Op-4)
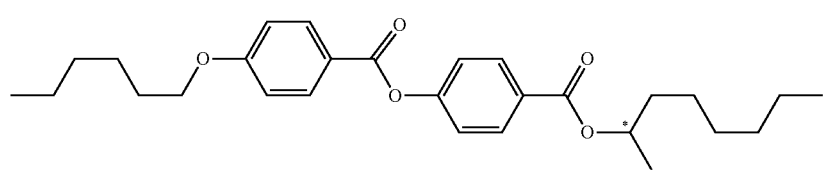
(Op-5)
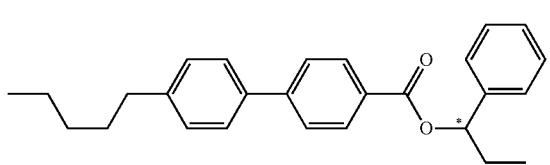
(Op-6)
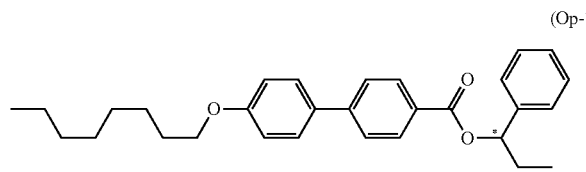
(Op-7)
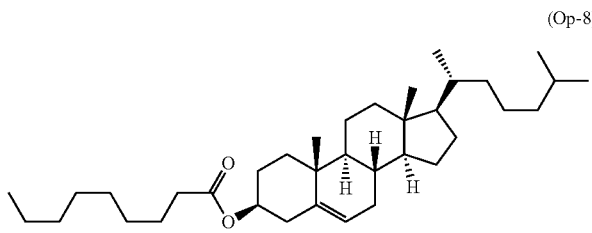
(Op-8)
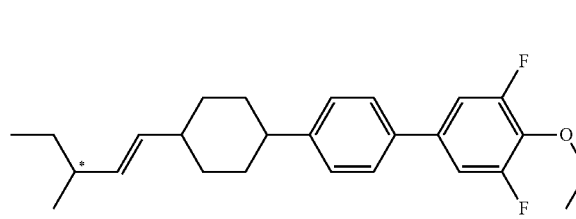
(Op-9)
(Op-10)
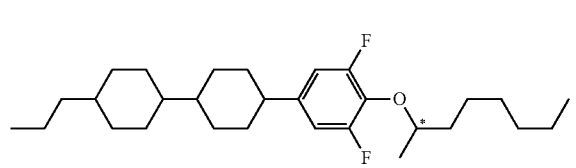
(Op-11)
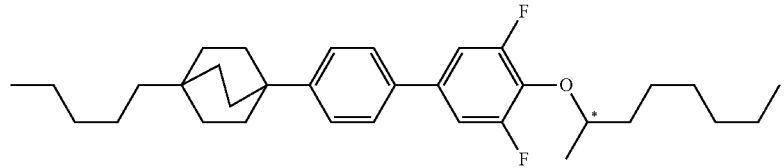
(Op-12)

(Op-13)
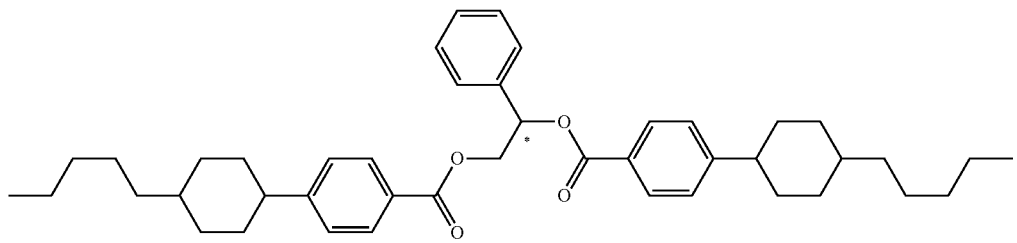

(Op-14)
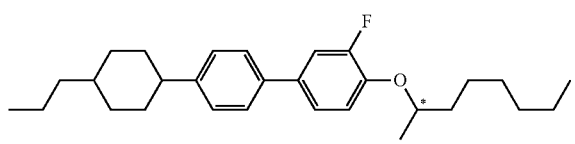

(Op-15)
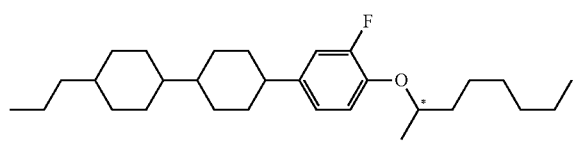

(Op-16)
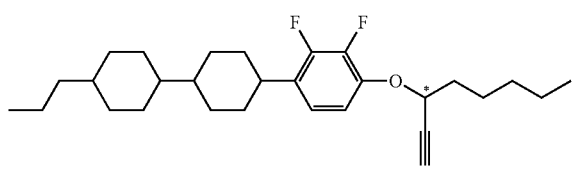

(Op-17)
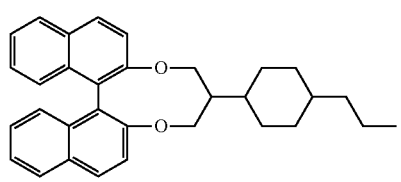

(Op-18)
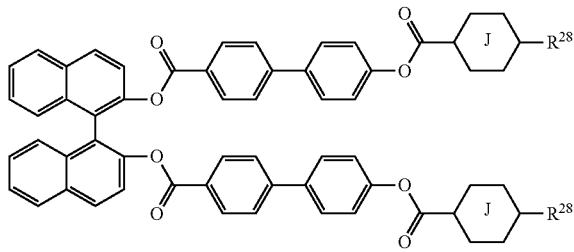

An antioxidant is effective in maintaining a large voltage holding ratio. Desirable examples of the antioxidant include compounds (AO-1) and (AO-2) described below; and Irganox 415, Irganox 565, Irganox 1010, Irganox 1035, Irganox 3114 and Irganox 1098 (trade name of BASF SE). An ultraviolet light absorber is effective for preventing a decrease in the maximum temperature. Desirable examples of the ultraviolet light absorber include benzophenone derivatives, benzoate derivatives and triazole derivatives. Specific examples include compounds (AO-3) and (AO-4) described below; Tinuvin 329, Tinuvin P, Tinuvin 326, Tinuvin 234, Tinuvin 213, Tinuvin 400, Tinuvin 328, Tinuvin 99-2 (trade name of BASF SE); and 1,4-diazabicyclo[2.2.2]octane (DABCO).

A light stabilizer such as amines with steric hindrance is also desirable for maintaining a large voltage holding ratio. Desirable examples of the light stabilizer include compounds (AO-5) and (AO-6) described below; and Tinuvin 144, Tinuvin 765 and Tinuvin 770DF (trade name of BASF SE). A thermal stabilizer is also effective in maintaining a large voltage holding ratio. Desirable examples include Irgafos 168 (trade name of BASF SE). A dichroic dye such as an azo dye or an anthraquinone dye is added to the composition for adjusting to a device having a guest host (GH) mode. An antifoaming agent is effective in preventing foam formation. Desirable examples of the antifoaming agent include dimethyl silicone oil and methyl phenyl silicone oil.

(AO-1)
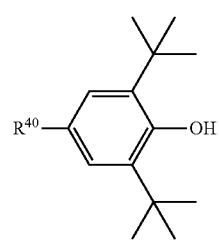

(AO-2)
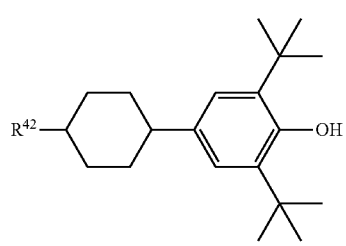

-continued

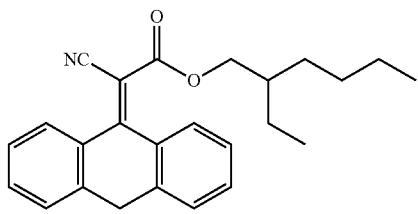
(AO-3)

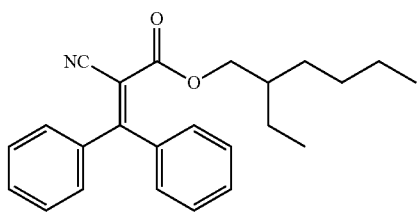
(AO-4)

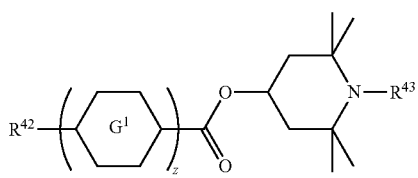
(AO-5)

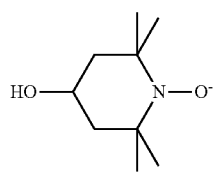
(AO-6)

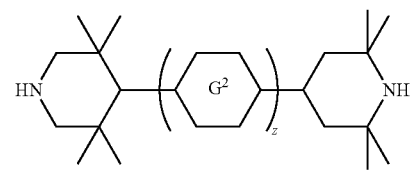
(AO-7)

In compound (AO-1), $R^{40}$ is alkyl having 1 to 20 carbons, alkoxy having 1 to 20 carbons, —COOR$^{41}$ or —CH$_2$CH$_2$COOR$^{41}$, where $R^{41}$ is alkyl having 1 to 20 carbons. In compounds (AO-2) and (AO-5), $R^{42}$ is alkyl having 1 to 20 carbons. In compound (AO-5), $R^{43}$ is hydrogen, methyl or O' (oxygen radical); ring G$^1$ is 1,4-cyclohexylene or 1,4-phenylene; in compound (AO-7), ring G$^2$ is 1,4-cyclohexylene, 1,4-phenylene or 1,4-phenylene in which at least one hydrogen has been replaced by fluorine; and in compounds (AO-5) and (AO-7), and z is 1, 2 or 3.

4. Liquid Crystal Display Devices

The liquid crystal composition can be used for a liquid crystal display device having a driving mode such as PC, TN, STN, OCB or PSA, which is driven by means of an active matrix mode. The composition can also be used for a liquid crystal display device having a driving mode such as PC, TN, STN, OCB, VA or IPS, which is driven by means of a passive matrix mode. These devices can be applied to any of a reflection type, a transmission type or a semi-transmission type.

The composition is suitable for a NCAP (nematic curvilinear aligned phase) device, where the composition is micro-encapsulated. The composition can be used for a polymer dispersed liquid crystal display device (PDLCD) or for a polymer network liquid crystal display device (PN-LCD). In these compositions, a polymerizable compound is added in large amounts. In contrast, a liquid crystal display device having a PSA mode is produced, when the ratio of the polymerizable compound is 10% by weight or less based on the weight of this liquid crystal composition. A desirable ratio is in the range of 0.1% by weight to 2% by weight. A more desirable ratio is in the range of 0.2% by weight to 1.0% by weight. The device having a PSA mode can be driven by means of a driving mode such as an active matrix mode or a passive matrix mode. This kind of device can be applied to any of a reflection type, a transmission type or a semi-transmission type.

EXAMPLES

1. Examples of Compound (1)

The invention will be explained in more detail by way of Examples. Examples are typical cases, and thus the invention is not limited by Examples. Compound (1) was prepared according to the procedures described below. Compounds prepared herein were identified by methods such as NMR analysis. The physical properties of compounds or compositions and the characteristics of devices were measured by the methods described below.

NMR Analysis: A model DRX-500 apparatus made by Bruker BioSpin Corporation was used for measurement. In the measurement of $^1$H-NMR, a sample was dissolved in a deuterated solvent such as CDCl$_3$, and measured under the conditions of room temperature, 500 MHz and 16 scan accumulation. Tetramethylsilane was used as an internal standard. In the measurement of $^{19}$F-NMR, CFCl$_3$ was used as an internal standard, and 24 scans were accumulated. In the explanation of the nuclear magnetic resonance spectra, the symbols s, d, t, q, quin, sex, m and br stand for a singlet, a doublet, a triplet, a quartet, a quintet, a sextet, a multiplet and line-broadening, respectively.

Gas Chromatographic Analysis: A gas chromatograph Model GC-2010 made by Shimadzu Corporation was used for measurement. The column used was a capillary column DB-1 (length 60 meters, bore 0.25 millimeters, film thickness 0.25 micrometers) made by Agilent Technologies, Inc. The carrier gas was helium (1 mL per minute). The sample injector and the detector (FID) were set to 300° C. A sample was dissolved in acetone to give a 0.1% solution by weight, and 1 microliter of the solution was injected into the sample injector. A recorder used was Model GC Solution System made by Shimadzu Corporation or the like.

HPLC Analysis: Model Prominence (LC-20AD; SPD-20A) made by Shimadzu Corporation was used for measurement. A column YMC-Pack ODS-A (length 150 millimeters, bore 4.6 millimeters, particle size 5 micrometers) made by YMC Co., Ltd. was used. Acetonitrile and water were properly mixed and used as eluent. A detector such as a UV detector, a RI detector or a Corona detector was properly used. The measurement wavelength was 254 nanometers when the UV detector was used. A sample was dissolved in acetonitrile to give a 0.1% by weight solution, and then 1 microliter of the solution was injected into the sample injector. Model C-R7Aplus made by Shimadzu Corporation was used as a recorder.

Ultraviolet and Visible Spectrophotometric Analysis: Model PharmaSpec UV-1700 made by Shimadzu Corporation was used for measurement. Wavelengths in the range of 190 nm to 700 nm were used for the detection. A sample was dissolved in acetonitrile, giving a 0.01 mmol/L solution, which was placed in a quartz cell (optical path length: 1 cm) and measured.

Sample for measurement: A compound itself was used as a sample when the phase structure and the transition temperature (a clearing point, a melting point, a starting temperature of polymerization or the like) were measured. A mixture of the compound and mother liquid crystals was used as a sample when physical properties such as the maximum temperature of a nematic phase, viscosity, optical anisotropy and dielectric anisotropy were measured.

When a mixture of a compound and mother liquid crystals was used as a sample, measurement was carried out in the following manner. The sample was prepared by mixing 15% by weight of the compound and 85% by weight of the mother liquid crystals. An extrapolated value was calculated from the measured value of the sample, according to the following equation, and the value was reported: [Extrapolated value]=(100×[Measured value of sample]−[% by weight of mother liquid crystals]×[Measured value of mother liquid crystals])/[% by weight of compound].

When crystals (or a smectic phase) deposited at 25° C. at this ratio, the ratio of the compound to the mother liquid crystals was changed in the order of (10% by weight: 90% by weight), (5% by weight: 95% by weight), and (1% by weight: 99% by weight). The physical properties of the sample were measured at the ratio in which the crystals (or the smectic phase) did not deposit at 25° C. Incidentally, the ratio of the compound to the mother liquid crystals is (15% by weight: 85% by weight), unless otherwise noted.

When the dielectric anisotropy of the compound was zero or positive, mother liquid crystals (A) described below was used. The ratio of each component was expressed as a percentage by weight.

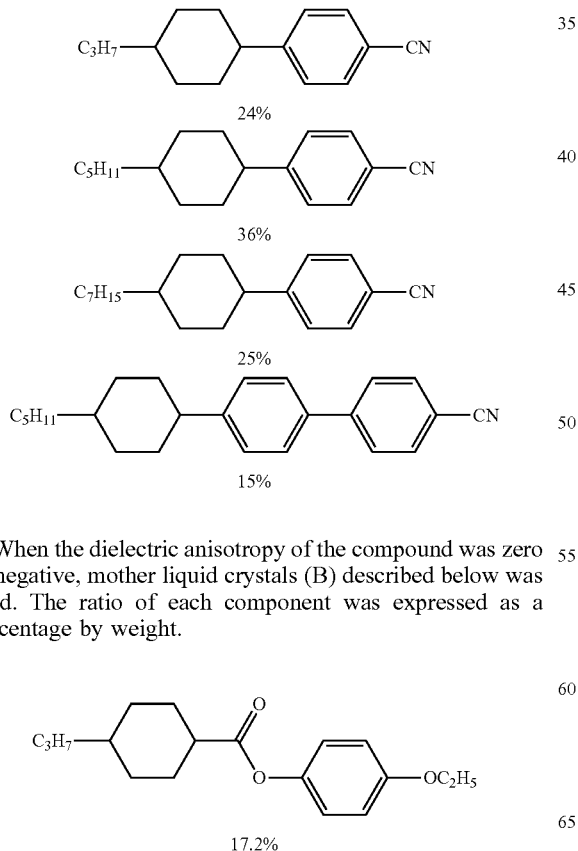

When the dielectric anisotropy of the compound was zero or negative, mother liquid crystals (B) described below was used. The ratio of each component was expressed as a percentage by weight.

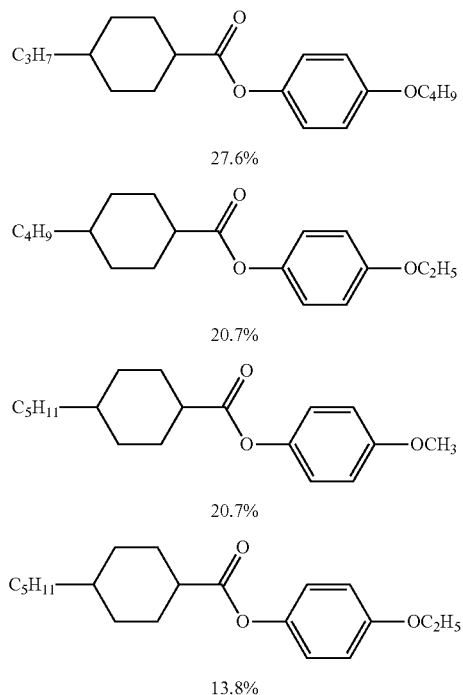

Mother liquid crystals (C): Mother liquid crystals (C) are sometimes used in which the component is the following fluorine compounds.

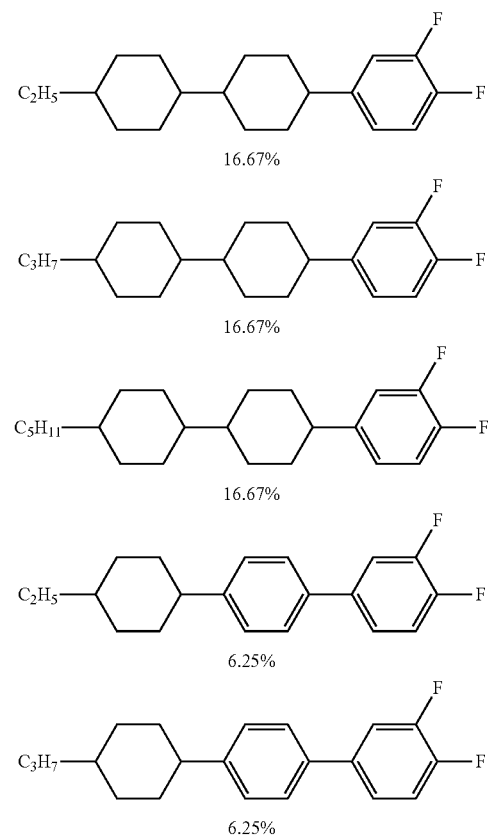

-continued

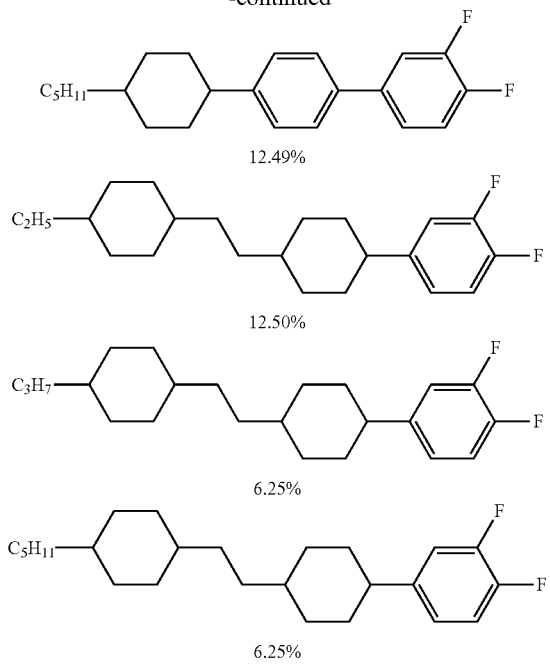

Measurement method: The physical properties were measured according to the following methods. Most of them are described in the JEITA standards (JEITA-ED-2521B) which was deliberated and established by Japan Electronics and Information Technology Industries Association (abbreviated to JEITA). A modified method was also used. No TFT was attached to a TN device used for measurement.

(1) Phase Structure: A sample was placed on a hot plate of a melting point apparatus (Hot Stage Model FP-52 made by Mettler Toledo International Inc.) equipped with a polarizing microscope, and the phase conditions and their changes were observed with the polarizing microscope while the sample was heated at the rate of 3° C. per minute, and the type of phase was specified.

(2) Transition Temperature (° C.): A differential scanning calorimeter, a Diamond DSC System made by PerkinElmer Inc. or a X-DSC7000 high sensitivity differential scanning analyzer made by SII NanoTechnology Inc. was used for measurement. A sample was heated and then cooled at the rate of 3° C. per minute, and the starting point of an endothermic peak or an exothermic peak caused by the phase change of the sample was obtained by extrapolation, and thus the transition temperature was determined. The melting point and the starting temperature of polymerization of a compound were also measured with this apparatus. The transition temperature of a compound from solid to a liquid crystal phase such as a smectic phase or a nematic phase is sometimes abbreviated to "the minimum temperature of a liquid crystal phase". The transition temperature of a compound from a liquid crystal phase to liquid is sometimes abbreviated to "clearing point".

The symbol C stood for crystals. When two types of crystals can be distinguished, each was expressed as $C_1$ or $C_2$. The symbols S and N stood for a smectic phase and a nematic phase, respectively. When phases such as a smectic A phase, a smectic B phase, a smectic C phase and a smectic F can be distinguished, they were expressed as $S_A$, $S_B$, $S_C$ and $S_F$, respectively. The symbol I stood for a liquid (isotropic). Transition temperatures were expressed as, for example, "C 50.0 N 100.0 Iso", which means that the transition temperature from crystals to a nematic phase was 50.0° C., and the transition temperature from the nematic phase to a liquid was 100.0° C.

(3) Compatibility of Compounds: Samples were prepared by mixing a compound with mother liquid crystals so that the ratio of the compound became 20% by weight, 15% by weight, 10% by weight, 5% by weight, 3% by weight or 1% by weight. The samples were placed in glass vials, and kept in a freezer at a temperature of −10° C. and −20° C. for a certain period of time. They were observed to determine whether or not the nematic phase was maintained or whether or not crystals (or a smectic phase) were deposited. The conditions that the nematic phase was maintained were used as a measure of the compatibility. The ratio of the compound or the temperature in the freezer may be changed, as requested.

(4) Maximum Temperature of a Nematic Phase ($T_{NI}$ or NI; ° C.): A sample was placed on a hot plate in a melting point apparatus equipped with a polarizing microscope and was heated at the rate of 1° C. per minute. The temperature was measured when part of the sample began to change from a nematic phase to an isotropic liquid. The symbol $T_{NI}$ means that the sample was a mixture of compound (1) and mother liquid crystals. The symbol NI means that the sample was a mixture of a compound (1) and compounds selected from compounds (2) to (15). The maximum temperature of a nematic phase is sometimes abbreviated to "maximum temperature".

(5) Minimum Temperature of a Nematic Phase ($T_C$; ° C.): A sample having a nematic phase was placed in a glass vials and kept in freezers at temperatures of 0° C., −10° C., −20° C., −30° C. and −40° C. for 10 days, and then the liquid crystal phases were observed. For example, when the sample maintained the nematic phase at −20° C. and changed to crystals or a smectic phase at −30° C., $T_C$ was expressed as <−20° C. A lower limit of the temperature range of a nematic phase is sometimes abbreviated to "minimum temperature".

(6) Viscosity (bulk viscosity; η; measured at 20° C.; mPa·s): An E-type viscometer made by Tokyo Keiki Inc. was used for measurement.

(7) Optical Anisotropy (Refractive Index Anisotropy; Δn; measured at 25° C.): Measurement was carried out using an Abbe refractometer with a polarizing plate attached to the ocular, using light at a wavelength of 589 nanometers. The surface of the main prism was rubbed in one direction, and then a sample was placed on the main prism. The refractive index (n||) was measured when the direction of the polarized light was parallel to that of the rubbing. The refractive index (n⊥) was measured when the direction of polarized light was perpendicular to that of the rubbing. The value of the optical anisotropy (Δn) was calculated from the equation: Δn=n||−n⊥.

(8) Specific Resistance (ρ; measured at 25° C.; Ωcm): A sample of 1.0 mL was poured into a vessel equipped with electrodes. A DC voltage (10 V) was applied to the vessel, and the DC current was measured after 10 seconds. The specific resistance was calculated from the following equation: (specific resistance)=[(voltage)×(electric capacity of vessel)]/[(DC current)×(dielectric constant in vacuum)].

(9) Voltage Holding Ratio (VHR-1; measured at 25° C.; %): A TN device used for measurement had a polyimide-alignment film, and the distance between the two glass substrates (cell gap) was 5 micrometers. A sample was poured into the device, and then the device was sealed with a UV-curable adhesive. A pulse voltage (60 microseconds at 5 V) was applied to the device and the device was charged. A decreasing voltage was measured for 16.7 milliseconds with a high-speed voltmeter, and area A between a voltage curve and a horizontal axis in a unit cycle was obtained. Area B was an area without the decrease. The voltage holding ratio was a percentage of area A to area B.

(10) Voltage Holding Ratio (VHR-2; measured at 80° C.; %): The voltage holding ratio was measured by the method described above, except that it was measured at 80° C. instead of 25° C. The resulting value was represented by the symbol VHR-2.

(11) Flicker Rate (measured at 25° C.; %): A multimedia display tester 3298F made by Yokogawa Electric Corporation was used for measurement. The light source was LED. A sample was poured into an FFS device having a normally black mode, in which the distance between the two glass substrates (cell gap) was 3.5 micrometers and the rubbing direction was antiparallel. This device was sealed with a UV-curable adhesive. A voltage was applied to the device and a voltage was measured when the amount of light passed through the device reached a maximum. The sensor was brought close to the device while this voltage was applied to the device, and the flicker rate displayed was recorded.

The measurement method of physical properties for a sample having positive dielectric anisotropy is sometimes different from these for a sample having negative dielectric anisotropy. Measurement methods were described in measurements (12a) to (16a) when the dielectric anisotropy was positive. They were described in measurements (12b) to (16b) when it was negative.

(12a) Viscosity (Rotational Viscosity; γl; measured at 25° C.; mPa·s; for samples having positive dielectric anisotropy): The measurement was carried out according to the method described in M. Imai, et al., Molecular Crystals and Liquid Crystals, Vol. 259, 37 (1995). A sample was poured into a TN device in which the twist angle was 0 degrees and the distance between the two glass substrates (cell gap) was 5 micrometers. A voltage was applied to the device and increased stepwise from 16 V to 19.5 V in increments of 0.5 V. After a period of 0.2 seconds with no voltage, a voltage was applied repeatedly under the conditions of a single rectangular wave alone (rectangular pulse; 0.2 seconds) and of no voltage (2 seconds). The peak current and the peak time of the transient current generated by the applied voltage were measured. The value of rotational viscosity was obtained from these measured values and equation (8) on page 40 of the paper presented by M. Imai, et al. The value of dielectric anisotropy necessary for this calculation was obtained by using the device that had been used for the measurement of rotational viscosity, according to the method that will be described below.

(12b) Viscosity (Rotational Viscosity; γl; measured at 25° C.; mPa·s; for samples having negative dielectric anisotropy): The measurement was carried out according to the method described in M. Imai, et al., Molecular Crystals and Liquid Crystals, Vol. 259, p. 37 (1995). A sample was poured into a VA device in which the distance between the two glass substrates (cell gap) was 20 micrometers. A voltage was applied to the device and increased from 39 V to 50 V in increments of 1 V. After a period of 0.2 seconds with no voltage, a voltage was applied repeatedly under the conditions of only one rectangular wave (rectangular pulse; 0.2 seconds) and no voltage (2 seconds). The peak current and the peak time of the transient current generated by the applied voltage were measured. The value of rotational viscosity was obtained from these measured values and equation (8) on page 40 of the paper presented by M. Imai, et al. The value of the dielectric anisotropy necessary for the present calculation was obtained by the method that will be described below, under the heading "Dielectric anisotropy".

(13a) Dielectric Anisotropy ($\Delta\varepsilon$; measured at 25° C.; for samples having positive dielectric anisotropy): A sample was poured into a TN device in which the distance between the two glass substrates (cell gap) was 9 micrometers and the twist angle was 80 degrees. Sine waves (10 V, 1 kHz) were applied to this device, and the dielectric constant ($\varepsilon\|$) in the major axis direction of liquid crystal molecules was measured after 2 seconds. Sine waves (0.5 V, 1 kHz) were applied to this device and the dielectric constant ($\varepsilon\perp$) in the minor axis direction of the liquid crystal molecules was measured after 2 seconds. The value of dielectric anisotropy was calculated from the equation: $\Delta\varepsilon=\varepsilon\|-\varepsilon\perp$.

(13b) Dielectric Anisotropy ($\Delta\varepsilon$; measured at 25° C.; for samples having negative dielectric anisotropy): The value of dielectric anisotropy was calculated from the equation: $\Delta\varepsilon=\varepsilon\|-\varepsilon\perp$. Dielectric constants ($\varepsilon\|$ and $\varepsilon\perp$) were measured as follows.

1) Measurement of a dielectric constant ($\varepsilon\|$): A solution of octadecyltriethoxysilane (0.16 mL) in ethanol (20 mL) was applied to thoroughly cleaned glass substrates. The glass substrates were rotated with a spinner, and then heated at 150° C. for one hour. A sample was poured into a VA device in which the distance between the two glass substrates (cell gap) was 4 micrometers, and then this device was sealed with a UV-curable adhesive. Sine waves (0.5 V, 1 kHz) were applied to this device, and the dielectric constant (Ell) in the major axis direction of liquid crystal molecules was measured after 2 seconds.

2) Measurement of a dielectric constant ($\varepsilon\perp$): A polyimide solution was applied to thoroughly cleaned glass substrates. The glass substrates were calcined, and then the resulting alignment film was subjected to rubbing. A sample was poured into a TN device in which the distance between the two glass substrates (cell gap) was 9 micrometers and the twist angle was 80 degrees. Sine waves (0.5 V, 1 kHz) were applied to this device, and the dielectric constant ($\varepsilon\perp$) in the minor axis direction of liquid crystal molecules was measured after 2 seconds.

(14a) Elastic Constants (K; measured at 25° C.; pN; for samples having positive dielectric anisotropy): A LCR meter Model HP 4284-A made by Yokogawa Hewlett-Packard, Ltd. was used for measurement. A sample was poured into a homogeneous device in which the distance between the two glass substrates (cell gap) was 20 micrometers. An electric charge of 0 V to 20 V was applied to this device, and the electrostatic capacity (C) and the applied voltage (V) were measured. These measured values were fitted to equation (2.98) and equation (2.101) on page 75 of the "Ekisho Debaisu Handobukku" (Liquid Crystal Device Handbook, in English; The Nikkan Kogyo Shimbun, Ltd., Japan) and the values of $K_{11}$ and $K_{33}$ were obtained from equation (2.99). Next, the value of $K_{22}$ was calculated from equation (3.18) on page 171 and the values of $K_{11}$ and $K_{33}$ thus obtained. The elastic constant K was expressed as an average value of $K_{11}$, $K_{22}$ and $K_{33}$.

(14b) Elastic Constants ($K_{11}$ and $K_{33}$; measured at 25° C.; pN; for samples having negative dielectric anisotropy): An elastic constant measurement system Model EC-1 made by Toyo Corporation was used for measurement. A sample was poured into a homeotropic device in which the distance between the two glass substrates (cell gap) was 20 micrometers. An electric charge of 20 V to 0 V was applied to this device, and electrostatic capacity and applied voltage were measured. The values of the electrostatic capacity (C) and the applied voltage (V) were fitted to equation (2.98) and equation (2.101) on page 75 of the "Ekisho Debaisu Handobukku" (Liquid Crystal Device Handbook, in English; The Nikkan Kogyo Shimbun, Ltd., Japan), and the value of the elastic constant was obtained from equation (2.100).

(15a) Threshold Voltage (Vth; measured at 25° C.; V; for samples having positive dielectric anisotropy): The measurement was carried out with an LCD evaluation system Model LCD-5100 made by Otsuka Electronics Co., Ltd. The light source was a halogen lamp. A sample was poured into a TN device having a normally white mode, in which the distance between the two glass substrates (cell gap) was 4.45/An (micrometer) and the twist angle was 80 degrees. The voltage to be applied to this device (32 Hz, rectangular waves) was stepwise increased in 0.02 V increments from 0 V up to 10 V. The device was simultaneously irradiated with light in the perpendicular direction, and the amount of light passing through the device was measured. A voltage-transmittance curve was prepared, in which the maximum amount of light corresponded to 100% transmittance and the minimum amount of light corresponded to 0% transmittance. The threshold voltage was expressed as voltage at 90% transmittance.

(15b) Threshold Voltage (Vth; measured at 25° C.; V; for samples having negative dielectric anisotropy): The measurement was carried out with an LCD evaluation system Model LCD-5100 made by Otsuka Electronics Co., Ltd. The light source was a halogen lamp. A sample was poured into a VA device having a normally black mode, in which the distance between the two glass substrates (cell gap) was 4 micrometers and the rubbing direction was antiparallel, and then this device was sealed with a UV-curable adhesive. The voltage to be applied to this device (60 Hz, rectangular waves) was stepwise increased in 0.02 V increments from 0 V up to 20 V. The device was simultaneously irradiated with light in the perpendicular direction, and the amount of light passing through the device was measured. A voltage-transmittance curve was prepared, in which the maximum amount of light corresponded to 100% transmittance and the minimum amount of light corresponded to 0% transmittance. The threshold voltage was voltage at 10% transmittance.

(16a) Response Time (τ; measured at 25° C.; millisecond; for samples having positive dielectric anisotropy): The measurement was carried out with an LCD evaluation system Model LCD-5100 made by Otsuka Electronics Co., Ltd. The light source was a halogen lamp. The low-pass filter was set at 5 kHz. A sample was poured into a TN device having a normally white mode, in which the distance between the two glass substrates (cell gap) was 5.0 micrometers and the twist angle was 80 degrees. Rectangular waves (60 Hz, 5 V, 0.5 seconds) were applied to this device. The device was simultaneously irradiated with light in the perpendicular direction, and the amount of light passing through the device was measured. The transmittance was regarded as 100% when the amount of light reached a maximum. The transmittance was regarded as 0% when the amount of light reached a minimum. Rise time (τr; millisecond) was the time required for a change from 90% to 10% transmittance. Fall time (τf; millisecond) was the time required for a change from 10% to 90% transmittance. The response time was expressed as the sum of the rise time and the fall time thus obtained.

(16b) Response Time (τ; measured at 25° C.; millisecond; for samples having negative dielectric anisotropy): The measurement was carried out with an LCD evaluation system Model LCD-5100 made by Otsuka Electronics Co., Ltd. The light source was a halogen lamp. The low-pass filter was set at 5 kHz. A sample was poured into a PVA device having a normally black mode, in which the distance between the two glass substrates (cell gap) was 3.2 micrometers, and the rubbing direction was antiparallel. This device was sealed with a UV-curable adhesive. A voltage that was a little more than the threshold voltage was applied to this device for 1 minute, and then the device was irradiated with ultraviolet light of 23.5 mW/cm² for 8 minutes while a voltage of 5.6 V was applied. Rectangular waves (60 Hz, 10 V, 0.5 seconds) were applied to this device. The device was simultaneously irradiated with light in the perpendicular direction, and the amount of light passing through the device was measured. The transmittance was regarded as 100% when the amount of light reached a maximum. The transmittance was regarded as 0% when the amount of light reached a minimum. The response time was expressed as the period of time required for the change from 90% to 10% transmittance (fall time: millisecond).

Starting materials: Solmix A-11 was a mixture of ethanol (85.5%), methanol (13.4%) and isopropanol (1.1%), and was available from Japan Alcohol Trading Co., Ltd.

Synthetic Example 1

Preparation of Compound (No. 109)

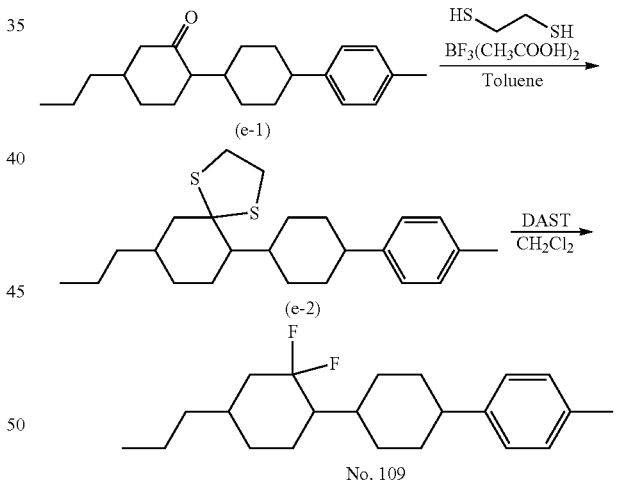

First Step:

Compound (e-1) (made by Organoscience Co., Ltd.) (9.3 g, 29.8 mmol), ethanedithiol (5.6 g, 59.5 mmol) was dissolved in toluene (54 ml) under an atmosphere of nitrogen. Boron trifluoride-acetic acid complex (5.6 g, 29.8 mmol) was added dropwise at 30° C., and the mixture was stirred overnight at room temperature. An aqueous solution (10%, 47 g) of sodium hydroxide was added to make pH=12. The mixture was extracted with toluene (50 ml). The resulting organic layer was separated, washed with brine, and dried over anhydrous magnesium sulfate. The solution was concentrated under reduced pressure to give compound (e-2) (11.6 g, 34.7 mmol).

Second Step:

Compound (e-2) (11.6 g, 34.7 mmol) and dichloromethane (140 ml) were placed in an reaction vessel under an atmosphere of nitrogen, and cooled to −15° C. (Diethylamino)sulfur trifluoride (DAST; 96.0 g, 595.6 mmol) was added dropwise in the temperature range of −15° C. to −10° C. After the addition, the reaction mixture was returned to 25° C., and stirred for 48 hours. The reaction solution was added dropwise to an aqueous solution of sodium carbonate to which ice was added, and the resulting precipitates were filtered. The organic layer of the filtrate was washed successively with an aqueous solution (10%) of sodium hydroxide, dilute hydrochloric acid, an aqueous solution of sodium hydrogencarbonate and brine, and dried over anhydrous magnesium sulfate. The solution was concentrated under reduced pressure, and the residue was purified by silica gel chromatography (heptane). Recrystallization from Solmix A-11 gave compound (No. 109) (3.1 g, 9.3 mmol).

$^1$H-NMR (δ ppm; CDCl$_3$): 7.09 (m, 4H), 2.41 (m, 1H), 2.31 (s, 3H), 2.11 (m, 1H), 1.99-1.76 (m, 7H), 1.58-1.20 (m, 13H), 0.89 (t, 3H).

The physical properties of compound (No. 109) were as follows. Transition temperature: C 62.3 N 145.6 I. $T_{NI}$=118.3° C.; η=28.7 mPa·s; Δn=0.100; Δε=−1.0.

Comparative Example 1

Comparison of Physical Properties

Compound (J) was selected as a comparative compound, and prepared. This compound is described in Example (25) of JP S57-165328 (1982), and is similar to the compound of the invention.

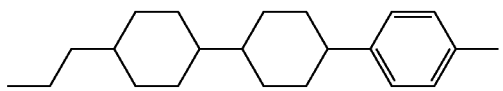 [SMILES: CCCC1CCC(C2CCC(c3ccc(C)cc3)CC2)CC1]

$^1$H-NMR (δ ppm; CDCl$_3$): 7.09 (s, 4H), 2.43-2.37 (m, 1H), 2.31 (s, 3H), 1.91-1.88 (m, 2H), 1.84-1.82 (m, 2H), 1.77-1.72 (m, 4H), 1.44-1.25 (m, 6H), 1.16-0.96 (m, 7H), 0.89-0.82 (m, 5H).

The physical properties of comparative compound (J) were as follows. Transition temperature: C 64.6 S 104.8 N 178.5 I. Maximum temperature ($T_{NI}$)=155.9° C.; viscosity (η)=15.0 mPa·s; optical anisotropy (Δn)=0.107; dielectric anisotropy (Δε)=0.3.

The physical properties of compound (No. 109) prepared in Synthetic example 1 and comparative compound (J) were summarized in Table 3. The measurement of the compatibility at low temperatures was carried out according to measurement (3) described above. A sample was prepared from 85% by weight of mother liquid crystals (B) and 15% by weight of the compound. The sample was kept in a refrigerator at −20° C., and the time was measured in which a nematic phase was maintained. It was found from Table 3 that compound (No. 109) was superior to the comparative compound in terms of the compatibility at low temperatures. Moreover, the elastic constant was measured according to measurement (14b) described above. Compound (No. 109) was superior in terms of a large elastic constant ratio ($K_{33}/K_{11}$).

Comparative Example 2

Comparison of Physical Properties

Compound (K) was prepared as a comparative compound. This was because this compound was compound (CCP-31FF) described in Example 7 of JP H08-048978 (1996), and was similar to the compound of the invention.

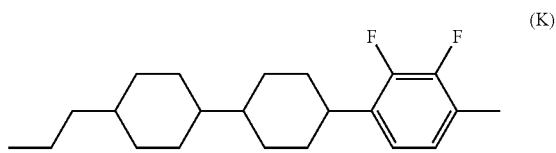 [SMILES: CCCC1CCC(C2CCC(c3ccc(C)c(F)c3F)CC2)CC1]

$^1$H-NMR (δ ppm; CDCl$_3$): 6.86-6.81 (m, 2H), 2.80-2.74 (m, 1H), 2.25 (d, 3H), 1.88-1.82 (m, 4H), 1.77-1.71 (m, 4H), 1.46-1.39 (m, 2H), 1.34-1.26 (m, 2H), 1.20-0.93 (m, 9H), 0.87-0.82 (m, 5H).

The physical properties of comparative compound (K) were as follows. Transition temperature: C 67.1 N 146.4 I. Maximum temperature ($T_{NI}$)=123.0° C.; viscosity (η)=27.4 mPa·s; optical anisotropy (Δn)=0.107; dielectric anisotropy (Δε)=−2.9.

TABLE 3

Physical properties of compound (No. 109) and comparative compound (J)

| | Compound (No. 109) | Comparative compound (J) |
|---|---|---|
| Structure | | |
| Compatibility at low temperatures (−20° C.) | 7 days | 3 days |
| Elastic constant ratio (K33/K11) | 1.23 | 1.00 |

TABLE 4

Physical properties of compound (No. 109) and comparative compound (K)

| | Compound (No. 109) | Comparative compound (K) |
|---|---|---|
| Structure | (see figure) | (see figure) |
| Elastic constant ratio ($K_{33}/K_{11}$) | 1.23 | 0.94 |
| Rotational viscosity ($\gamma 1$) (mPa·s) | 79.24 | 82.34 |

Compound (K) was selected for comparison. This was because two fluorines were common between compound (No. 109) prepared in Synthetic example 1 and comparative compound (K). A sample was prepared from 15% by weight of compound (No. 109) and 85% by weight of mother liquid crystals (B) for measuring the elastic constant ($K_{33}$ and $K_{11}$). The elastic constant was measured according to measurement (14b) described above. A sample was prepared from 92% by weight of mother liquid crystals (D) described below and 8% by weight of compound (No. 109) for the rotational viscosity (γ1). The rotational viscosity was measured according to measurement (12a) described above. The results were summarized in Table 4. It was found that compound (No. 109) was superior in terms of a large elastic constant ratio. It was found that compound (No. 109) was superior in terms of a small rotational viscosity.

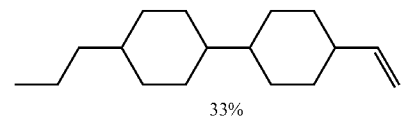

33%

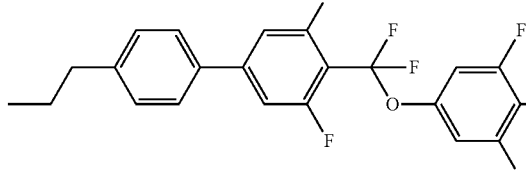

14%

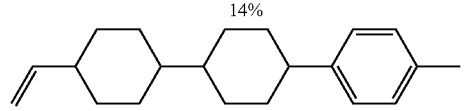

14%

3%

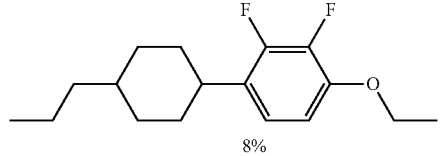

8%

-continued

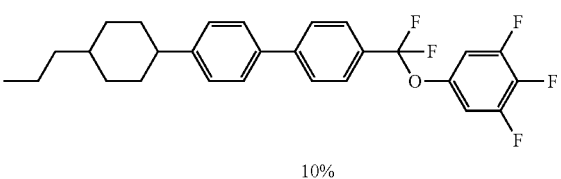

10%

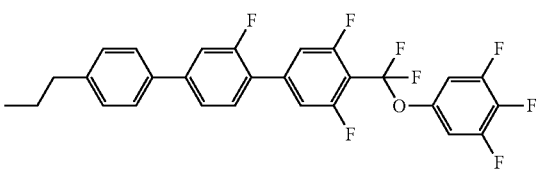

2%

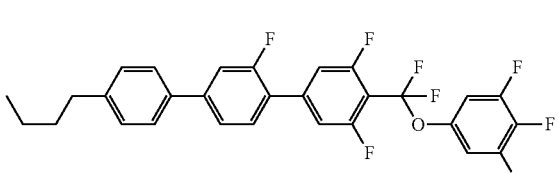

8%

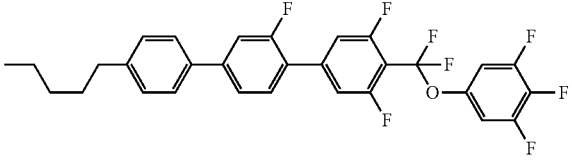

4%

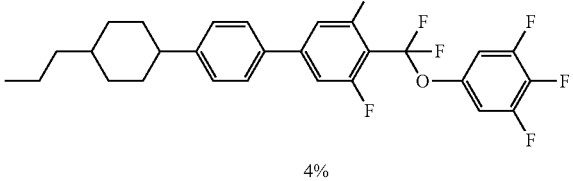

4%

2. Preparation of Compound (1)

Compound (1) is prepared according to "2. Preparation of compound (1)" and "Synthetic examples", these of which were described above. Examples of this type of compounds includes compounds (No. 1) to (No. 216) described below.

| No. | |
|---|---|
| 1 | 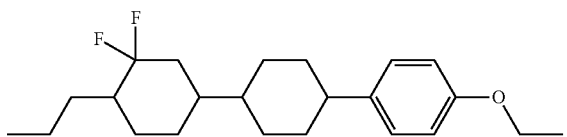 [SMILES: CCCC1CCC(C2CCC(c3ccc(OCC)cc3)CC2)CC1(F)F] |
| 2 | 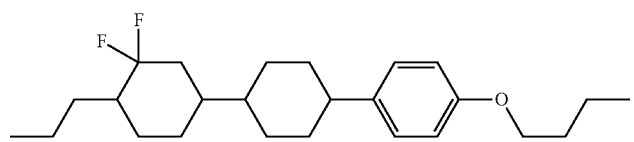 [SMILES: CCCCOc1ccc(C2CCC(C3CCC(CCC)C(F)(F)C3)CC2)cc1] |
| 3 | 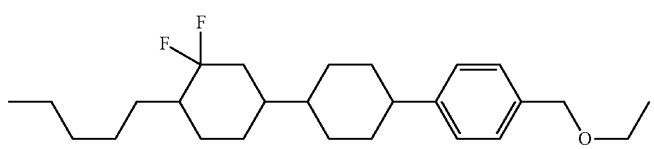 [SMILES: CCCCCC1CCC(C2CCC(c3ccc(COCC)cc3)CC2)CC1(F)F] |
| 4 | 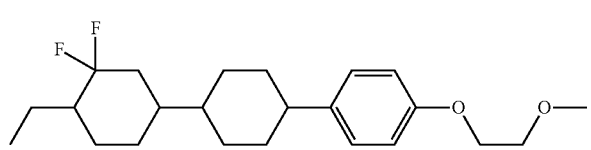 [SMILES: CCC1CCC(C2CCC(c3ccc(OCCOC)cc3)CC2)CC1(F)F] |
| 5 | 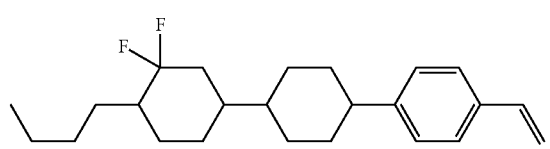 |
| 6 | 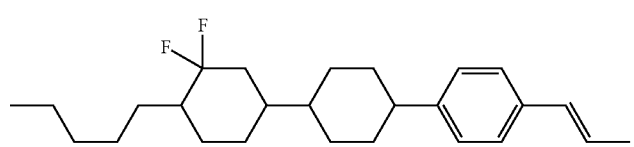 [SMILES: C/C=C/c1ccc(C2CCC(C3CCC(CCCCC)C(F)(F)C3)CC2)cc1] |
| 7 | 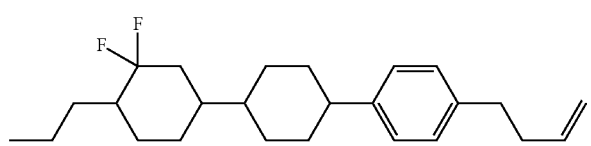 |
| 8 | 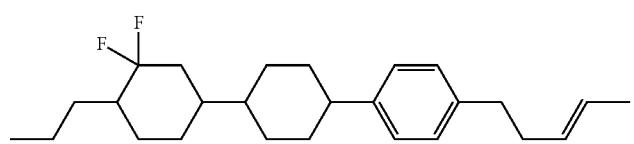 |
| 9 | 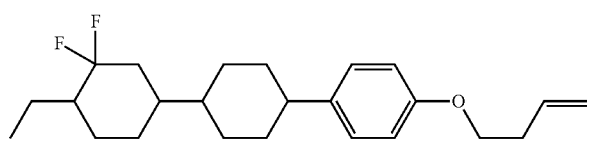 [SMILES: C=CCCOc1ccc(C2CCC(C3CCC(CC)C(F)(F)C3)CC2)cc1] |
| 10 | 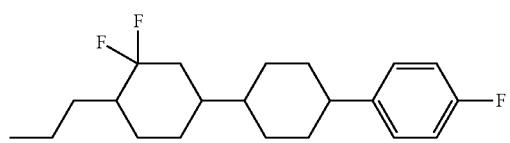 [SMILES: CCCC1CCC(C2CCC(c3ccc(F)cc3)CC2)CC1(F)F] |
| 11 | 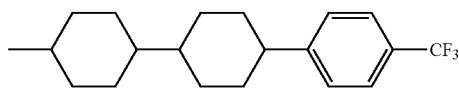 |

-continued
| No. | |
|---|---|
| 12 | 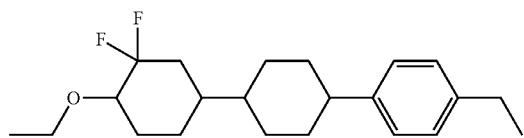 [SMILES: CCOC1CCC(C2CCC(c3ccc(CC)cc3)CC2)CC1(F)F] |
| 13 | 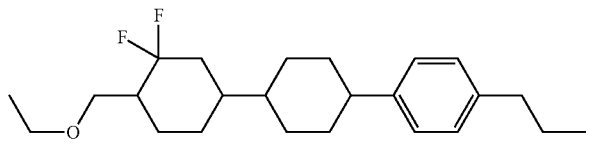 [SMILES: CCCc1ccc(C2CCC(C3CCC(COCC)C(F)(F)C3)CC2)cc1] |
| 14 | 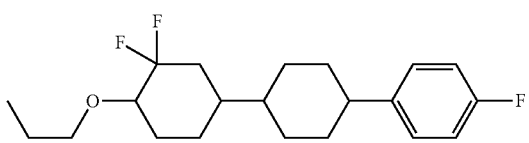 [SMILES: CCCOC1CCC(C2CCC(c3ccc(F)cc3)CC2)CC1(F)F] |
| 15 | 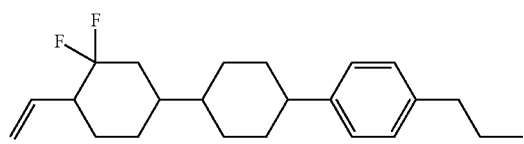 [SMILES: C=CC1CCC(C2CCC(c3ccc(CCC)cc3)CC2)CC1(F)F] |
| 16 | 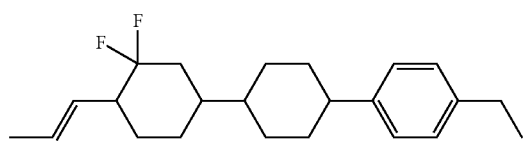 |
| 17 | 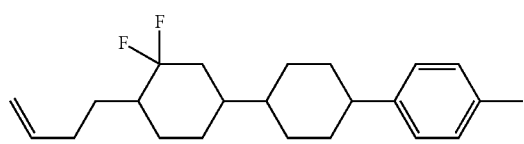 [SMILES: C=CCCC1CCC(C2CCC(c3ccc(C)cc3)CC2)CC1(F)F] |
| 18 | 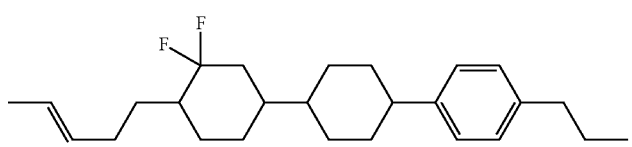 [SMILES: C/C=C/CCC1CCC(C2CCC(c3ccc(CCC)cc3)CC2)CC1(F)F] |
| 19 | 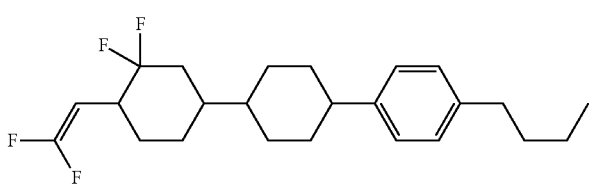 [SMILES: CCCCc1ccc(C2CCC(C3CCC(C=C(F)F)C(F)(F)C3)CC2)cc1] |
| 20 | 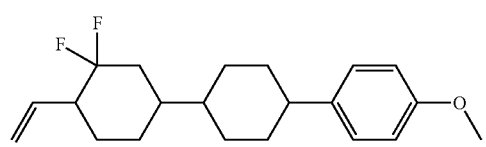 [SMILES: C=CC1CCC(C2CCC(c3ccc(OC)cc3)CC2)CC1(F)F] |
| 21 | 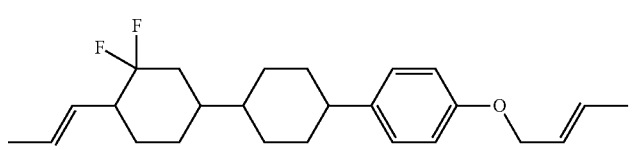 |

-continued
| No. | |
|---|---|
| 22 | 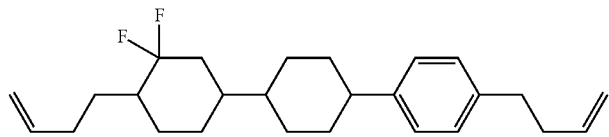 [SMILES: C=CCCc1ccc(C2CCC(C3CCC(CCC=C)C(F)(F)C3)CC2)cc1] |
| 23 | 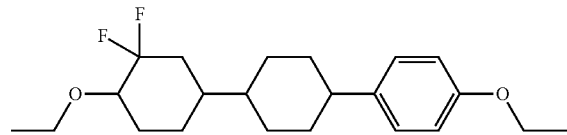 [SMILES: CCOc1ccc(C2CCC(C3CCC(OCC)C(F)(F)C3)CC2)cc1] |
| 24 | 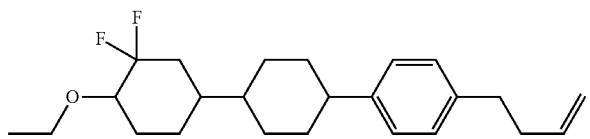 [SMILES: C=CCCc1ccc(C2CCC(C3CCC(OCC)C(F)(F)C3)CC2)cc1] |
| 25 | 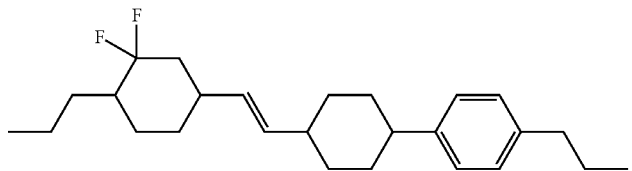 [SMILES: CCCc1ccc(C2CCC(/C=C/C3CCC(CCC)C(F)(F)C3)CC2)cc1] |
| 26 | 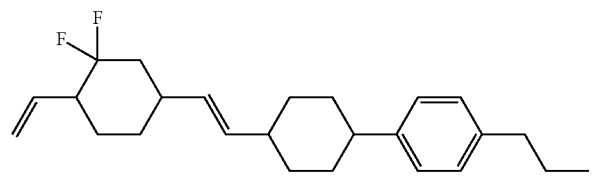 [SMILES: C=CC1CCC(/C=C/C2CCC(c3ccc(CCC)cc3)CC2)CC1(F)F] |
| 27 | 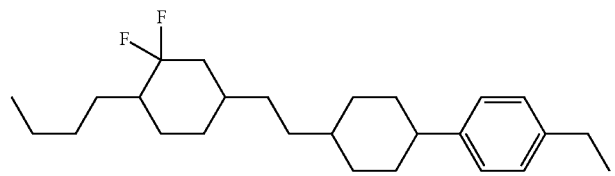 [SMILES: CCCCC1CCC(CCC2CCC(c3ccc(CC)cc3)CC2)CC1(F)F] |
| 28 | 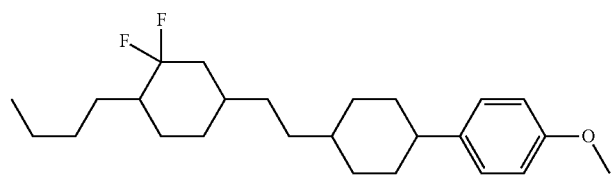 [SMILES: CCCCC1CCC(CCC2CCC(c3ccc(OC)cc3)CC2)CC1(F)F] |
| 29 | 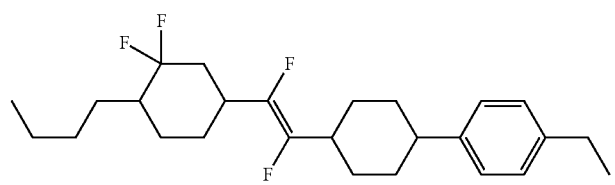 [SMILES: CCCCC1CCC(/C(F)=C(\F)C2CCC(c3ccc(CC)cc3)CC2)CC1(F)F] |
| 30 | 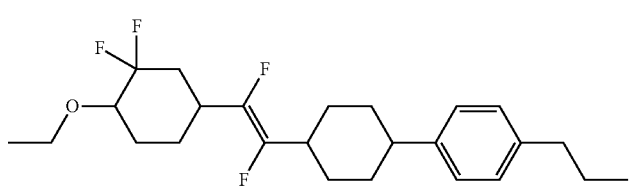 [SMILES: CCCc1ccc(C2CCC(/C(F)=C(\F)C3CCC(OCC)C(F)(F)C3)CC2)cc1] |

-continued
| No. | |
|---|---|
| 31 | 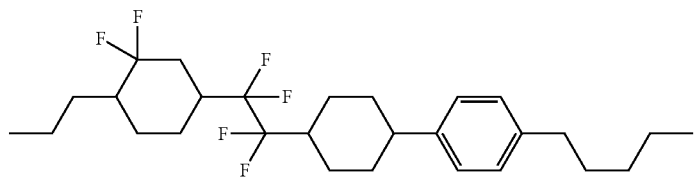 |
| 32 | 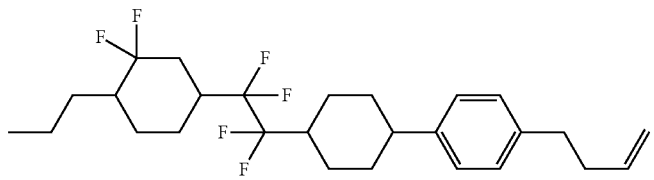 [SMILES: C=CCCc1ccc(C2CCC(C(F)(F)C(F)(F)C3CCC(CCC)C(F)(F)C3)CC2)cc1] |
| 33 | 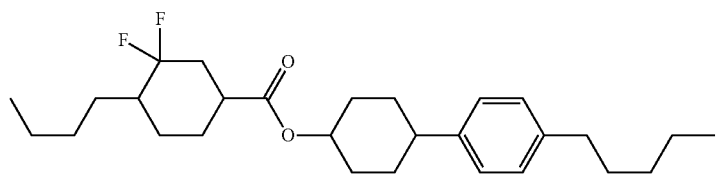 [SMILES: CCCCCc1ccc(C2CCC(OC(=O)C3CCC(CCCC)C(F)(F)C3)CC2)cc1] |
| 34 | 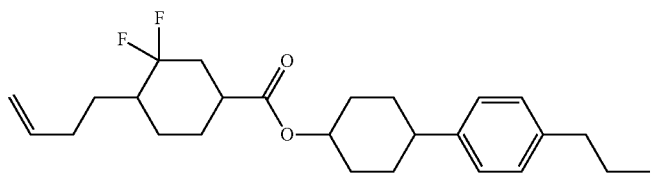 [SMILES: C=CCCC1CCC(C(=O)OC2CCC(c3ccc(CCC)cc3)CC2)CC1(F)F] |
| 35 | 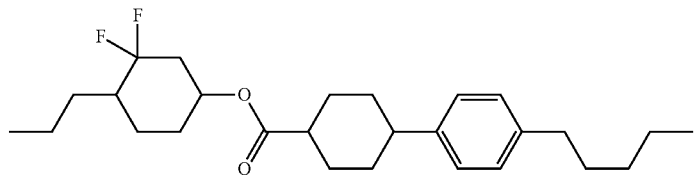 [SMILES: CCCCCc1ccc(C2CCC(C(=O)OC3CCC(CCC)C(F)(F)C3)CC2)cc1] |
| 36 | 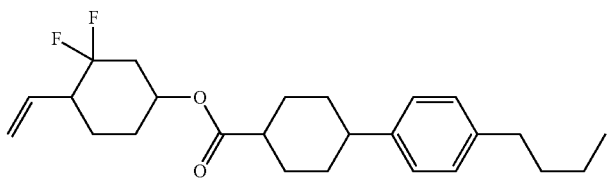 [SMILES: C=CC1CCC(OC(=O)C2CCC(c3ccc(CCCC)cc3)CC2)CC1(F)F] |
| 37 | 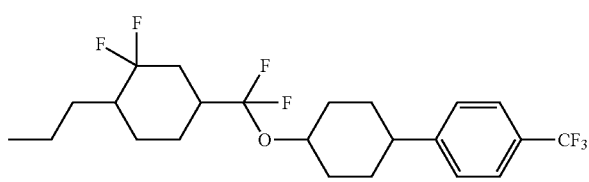 [SMILES: CCCC1CCC(C(F)(F)OC2CCC(c3ccc(C(F)(F)F)cc3)CC2)CC1(F)F] |
| 38 | 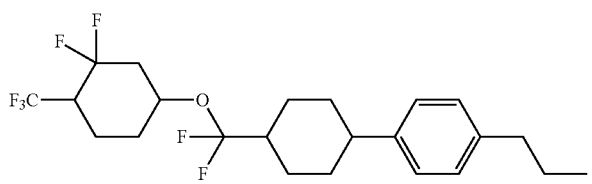 [SMILES: CCCc1ccc(C2CCC(C(F)(F)OC3CCC(C(F)(F)F)C(F)(F)C3)CC2)cc1] |

| No. |
| --- |
| 39 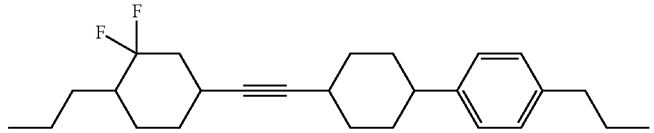 [SMILES: CCCc1ccc(C2CCC(C#CC3CCC(CCC)C(F)(F)C3)CC2)cc1] |
| 40 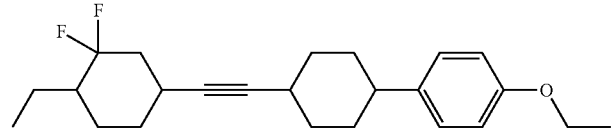 [SMILES: CCOc1ccc(C2CCC(C#CC3CCC(CC)C(F)(F)C3)CC2)cc1] |
| 41 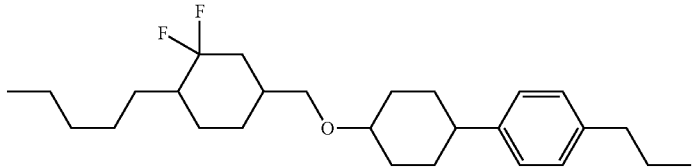 [SMILES: CCCCCC1CCC(COC2CCC(c3ccc(CCC)cc3)CC2)CC1(F)F] |
| 42 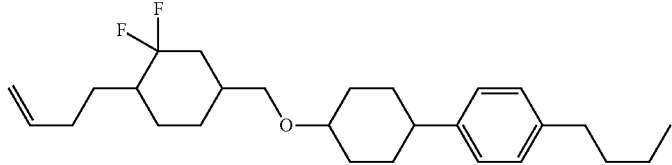 [SMILES: C=CCCC1CCC(COC2CCC(c3ccc(CCCC)cc3)CC2)CC1(F)F] |
| 43 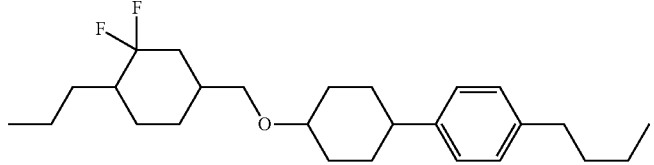 [SMILES: CCCCc1ccc(C2CCC(OCC3CCC(CCC)C(F)(F)C3)CC2)cc1] |
| 44 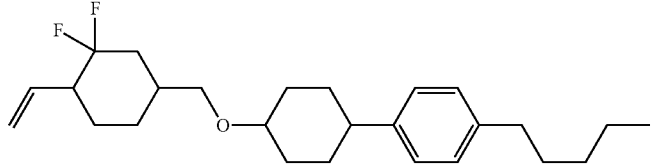 [SMILES: C=CC1CCC(COC2CCC(c3ccc(CCCCC)cc3)CC2)CC1(F)F] |
| 45 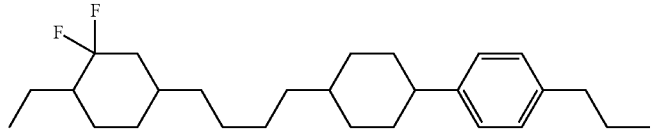 [SMILES: CCCc1ccc(C2CCC(CCCCC3CCC(CC)C(F)(F)C3)CC2)cc1] |
| 46 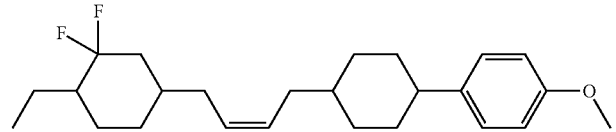 [SMILES: CCC1CCC(C/C=C\CC2CCC(c3ccc(OC)cc3)CC2)CC1(F)F] |
| 47 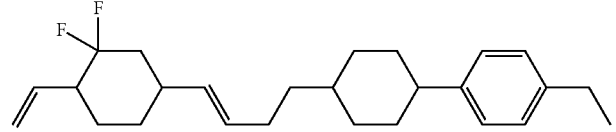 |
| 48 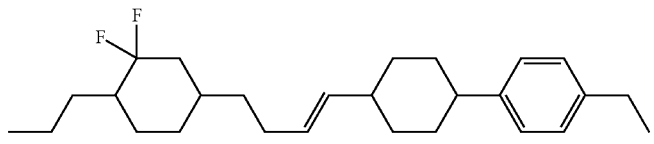 [SMILES: CCCC1CCC(CC/C=C/C2CCC(c3ccc(CC)cc3)CC2)CC1(F)F] |

-continued
| No. | |
|---|---|
| 49 | 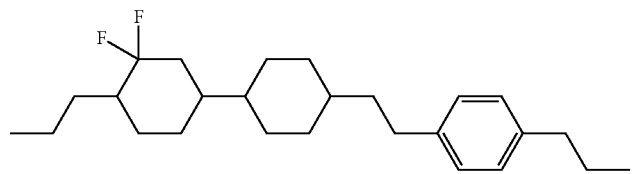 [SMILES: CCCc1ccc(CCC2CCC(C3CCC(CCC)C(F)(F)C3)CC2)cc1] |
| 50 | 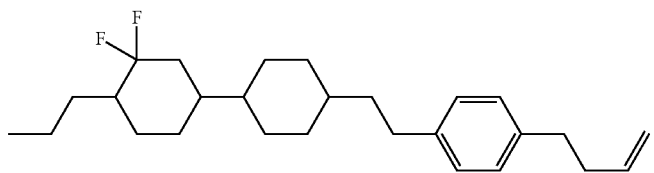 [SMILES: C=CCCc1ccc(CCC2CCC(C3CCC(CCC)C(F)(F)C3)CC2)cc1] |
| 51 | 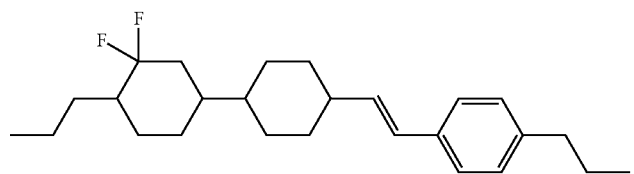 [SMILES: CCCc1ccc(/C=C/C2CCC(C3CCC(CCC)C(F)(F)C3)CC2)cc1] |
| 52 | 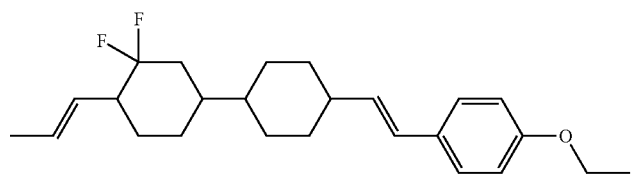 [SMILES: C/C=C/C1CCC(C2CCC(/C=C/c3ccc(OCC)cc3)CC2)CC1(F)F] |
| 53 | 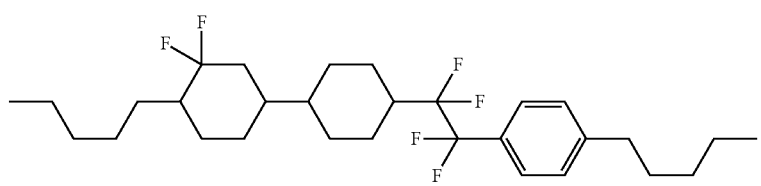 [SMILES: CCCCCc1ccc(C(F)(F)C(F)(F)C2CCC(C3CCC(CCCCC)C(F)(F)C3)CC2)cc1] |
| 54 | 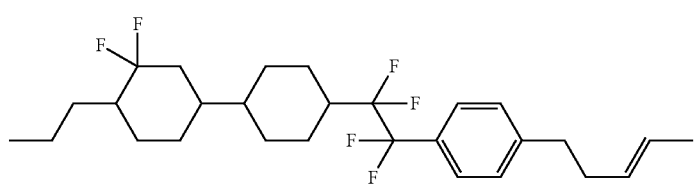 [SMILES: C/C=C/CCc1ccc(C(F)(F)C(F)(F)C2CCC(C3CCC(CCC)C(F)(F)C3)CC2)cc1] |
| 55 | 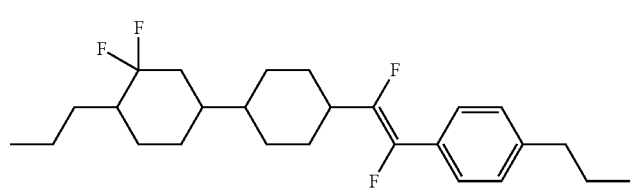 [SMILES: CCCc1ccc(/C(F)=C(\F)C2CCC(C3CCC(CCC)C(F)(F)C3)CC2)cc1] |
| 56 | 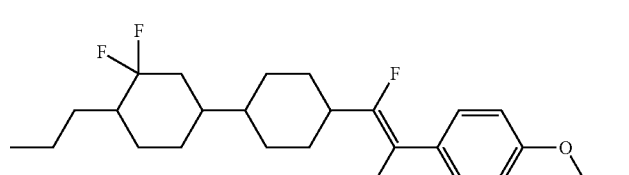 |

-continued
| No. | |
|---|---|
| 57 | 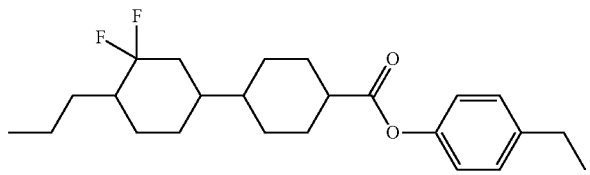 [SMILES: CCCC1CCC(C2CCC(C(=O)Oc3ccc(CC)cc3)CC2)CC1(F)F] |
| 58 | 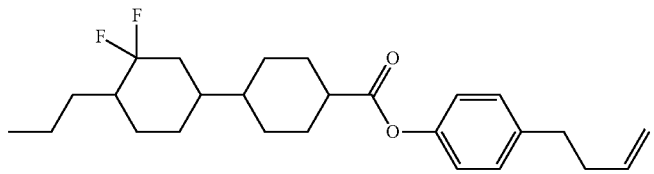 [SMILES: C=CCCc1ccc(OC(=O)C2CCC(C3CCC(CCC)C(F)(F)C3)CC2)cc1] |
| 59 | 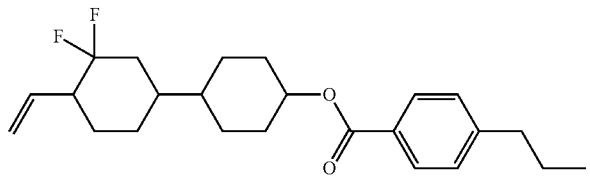 |
| 60 | 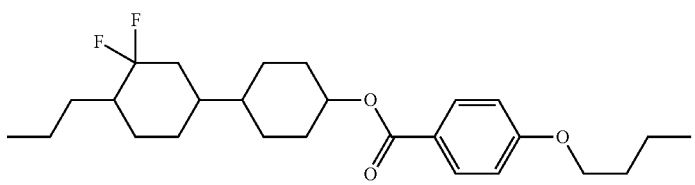 [SMILES: CCCCOc1ccc(C(=O)OC2CCC(C3CCC(CCC)C(F)(F)C3)CC2)cc1] |
| 61 | 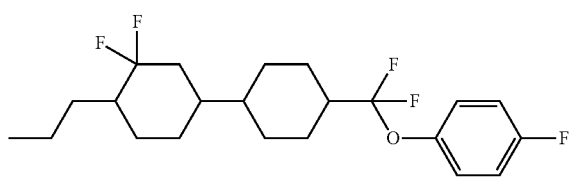 [SMILES: CCCC1CCC(C2CCC(C(F)(F)Oc3ccc(F)cc3)CC2)CC1(F)F] |
| 62 | 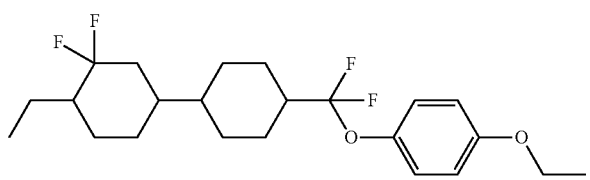 |
| 63 | 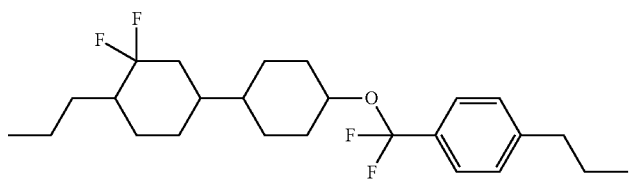 [SMILES: CCCc1ccc(C(F)(F)OC2CCC(C3CCC(CCC)C(F)(F)C3)CC2)cc1] |
| 64 | 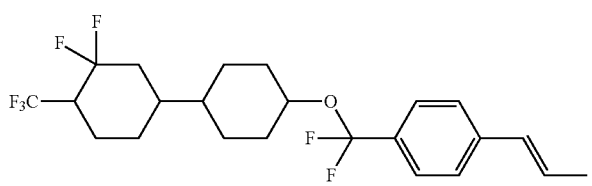 [SMILES: C/C=C/c1ccc(C(F)(F)OC2CCC(C3CCC(C(F)(F)F)C(F)(F)C3)CC2)cc1] |

| No. |
| --- |
| 65 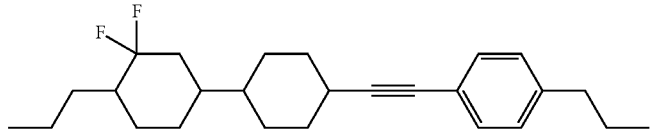 [SMILES: CCCc1ccc(C#CC2CCC(C3CCC(CCC)C(F)(F)C3)CC2)cc1] |
| 66 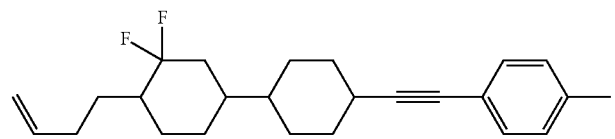 [SMILES: C=CCCC1CCC(C2CCC(C#Cc3ccc(C)cc3)CC2)CC1(F)F] |
| 67 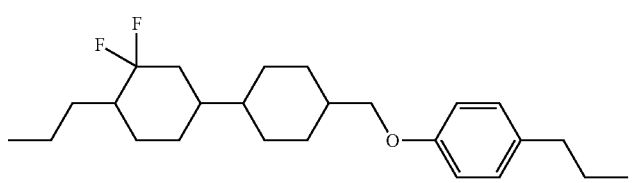 [SMILES: CCCc1ccc(OCC2CCC(C3CCC(CCC)C(F)(F)C3)CC2)cc1] |
| 68 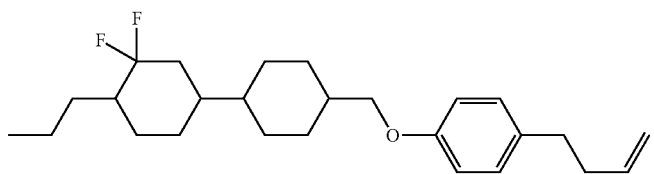 [SMILES: C=CCCc1ccc(OCC2CCC(C3CCC(CCC)C(F)(F)C3)CC2)cc1] |
| 69 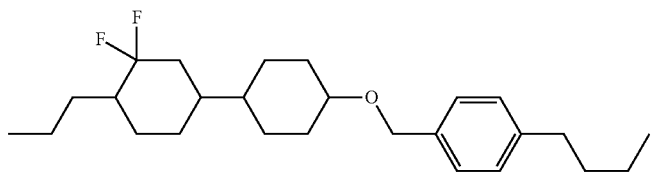 [SMILES: CCCCc1ccc(COC2CCC(C3CCC(CCC)C(F)(F)C3)CC2)cc1] |
| 70 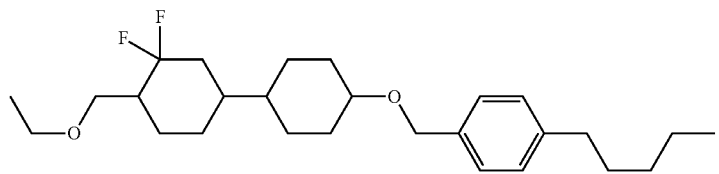 |
| 71 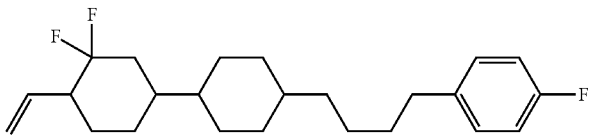 |
| 72 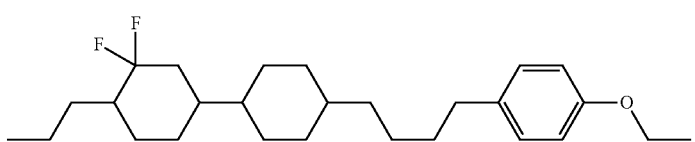 [SMILES: CCCC1CCC(C2CCC(CCCCc3ccc(OCC)cc3)CC2)CC1(F)F] |
| 73 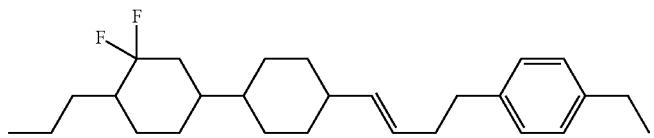 [SMILES: CCCC1CCC(C2CCC(/C=C/CCc3ccc(CC)cc3)CC2)CC1(F)F] |
| 74 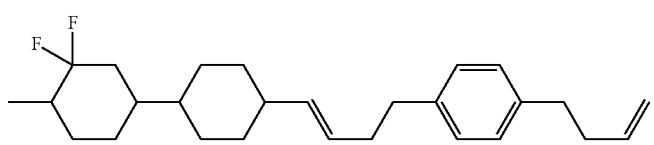 [SMILES: C=CCCc1ccc(CC/C=C/C2CCC(C3CCC(C)C(F)(F)C3)CC2)cc1] |

| No. | |
|---|---|
| 75 | 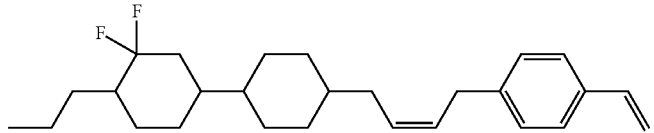 [SMILES: C=Cc1ccc(C/C=C\CC2CCC(C3CCC(CCC)C(F)(F)C3)CC2)cc1] |
| 76 | 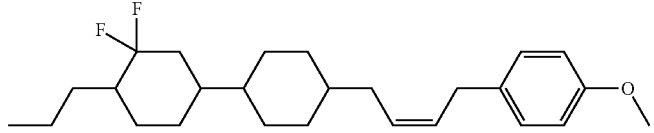 [SMILES: CCCC1CCC(C2CCC(C/C=C\Cc3ccc(OC)cc3)CC2)CC1(F)F] |
| 77 | 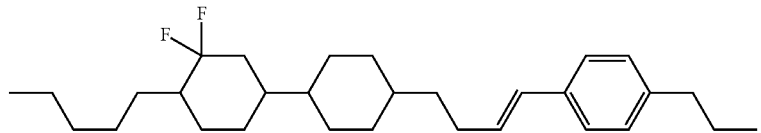 [SMILES: CCCCCC1CCC(C2CCC(CC/C=C/c3ccc(CCC)cc3)CC2)CC1(F)F] |
| 78 | 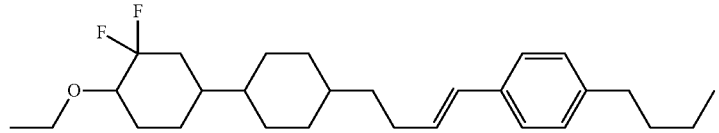 [SMILES: CCCCc1ccc(/C=C/CCC2CCC(C3CCC(OCC)C(F)(F)C3)CC2)cc1] |
| 79 | 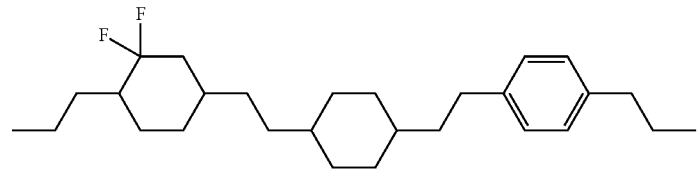 |
| 80 | 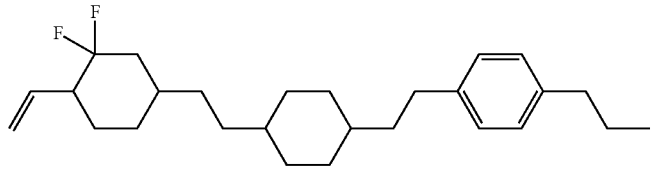 [SMILES: C=CC1CCC(CCC2CCC(CCc3ccc(CCC)cc3)CC2)CC1(F)F] |
| 81 | 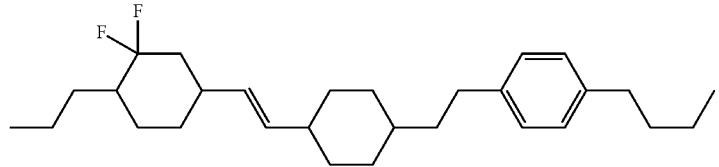 |
| 82 | 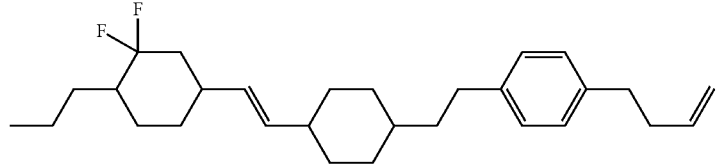 [SMILES: CCCCc1ccc(CCC2CCC(/C=C/C3CCC(CCC)C(F)(F)C3)CC2)cc1] |
| 83 | 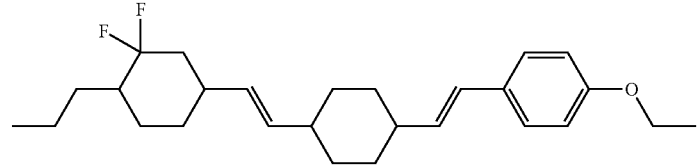 [SMILES: CCCC1CCC(/C=C/C2CCC(/C=C/c3ccc(OCC)cc3)CC2)CC1(F)F] |

| No. |  |
|---|---|
| 84 | 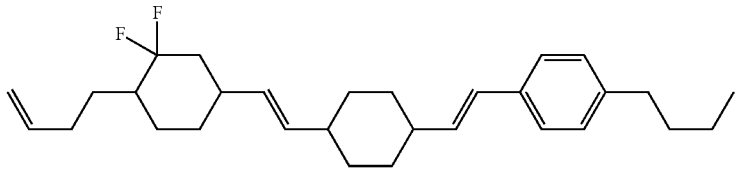 [SMILES: C=CCCC1CCC(/C=C/C2CCC(/C=C/c3ccc(CCCC)cc3)CC2)CC1(F)F] |
| 85 | 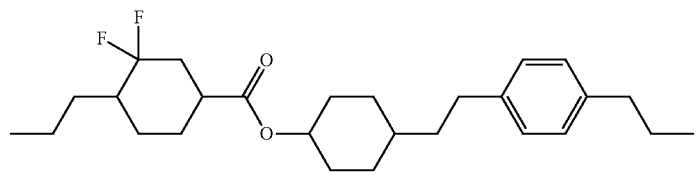 |
| 86 | 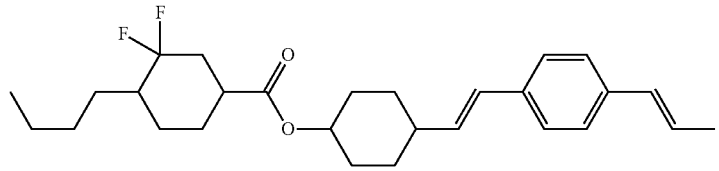 [SMILES: C/C=C/c1ccc(/C=C/C2CCC(OC(=O)C3CCC(CCCC)C(F)(F)C3)CC2)cc1] |
| 87 | 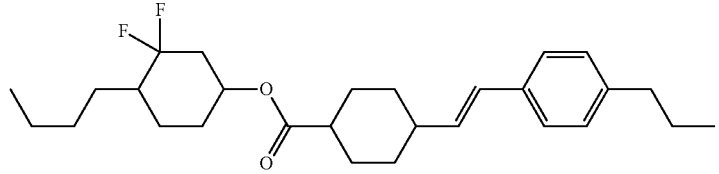 [SMILES: CCCCC1CCC(OC(=O)C2CCC(/C=C/c3ccc(CCC)cc3)CC2)CC1(F)F] |
| 88 | 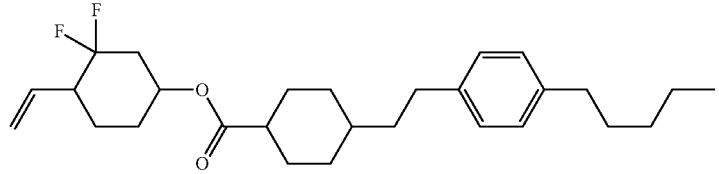 [SMILES: C=CC1CCC(OC(=O)C2CCC(CCc3ccc(CCCCC)cc3)CC2)CC1(F)F] |
| 89 | 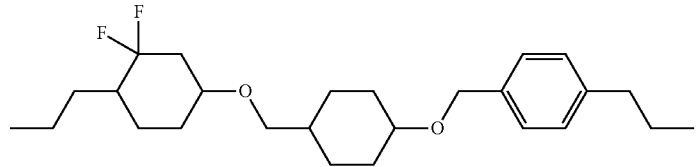 [SMILES: CCCc1ccc(COC2CCC(COC3CCC(CCC)C(F)(F)C3)CC2)cc1] |
| 90 | 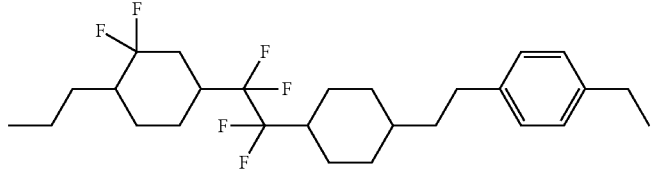 [SMILES: CCCC1CCC(C(F)(F)C(F)(F)C2CCC(CCc3ccc(CC)cc3)CC2)CC1(F)F] |
| 91 | 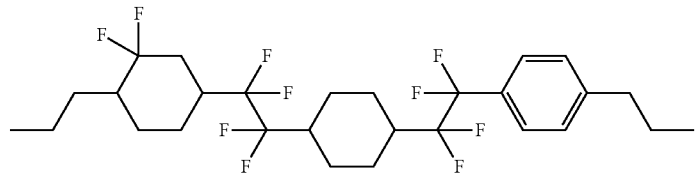 [SMILES: CCCc1ccc(C(F)(F)C(F)(F)C2CCC(C(F)(F)C(F)(F)C3CCC(CCC)C(F)(F)C3)CC2)cc1] |

-continued
| No. | |
|---|---|
| 92 | 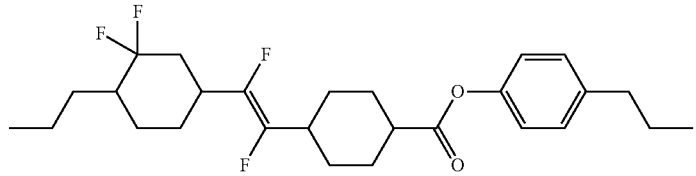 |
| 93 | 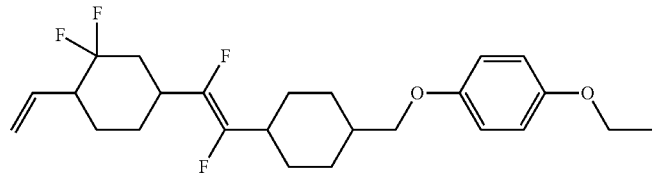 [SMILES: C=CC1CCC(/C(F)=C(\F)C2CCC(COc3ccc(OCC)cc3)CC2)CC1(F)F] |
| 94 | 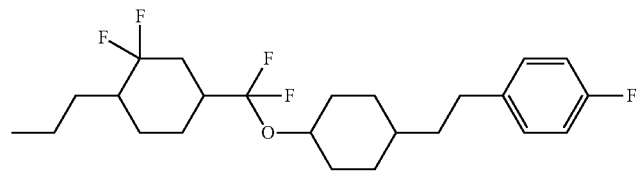 [SMILES: CCCC1CCC(C(F)(F)OC2CCC(CCc3ccc(F)cc3)CC2)CC1(F)F] |
| 95 | 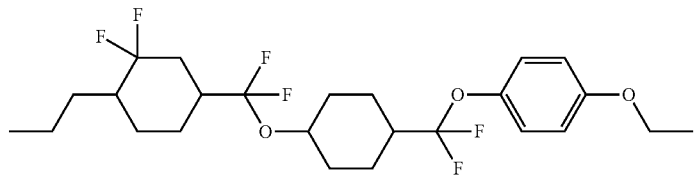 [SMILES: CCCC1CCC(C(F)(F)OC2CCC(C(F)(F)Oc3ccc(OCC)cc3)CC2)CC1(F)F] |
| 96 | 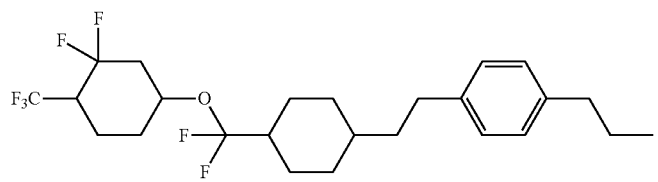 [SMILES: CCCc1ccc(CCC2CCC(C(F)(F)OC3CCC(C(F)(F)F)C(F)(F)C3)CC2)cc1] |
| 97 | 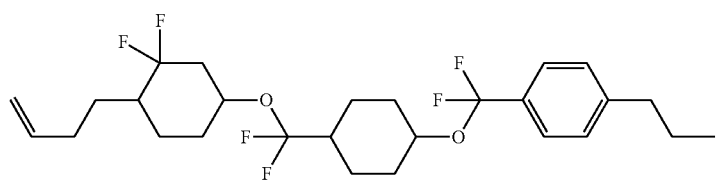 [SMILES: C=CCCC1CCC(OC(F)(F)C2CCC(OC(F)(F)c3ccc(CCC)cc3)CC2)CC1(F)F] |
| 98 | 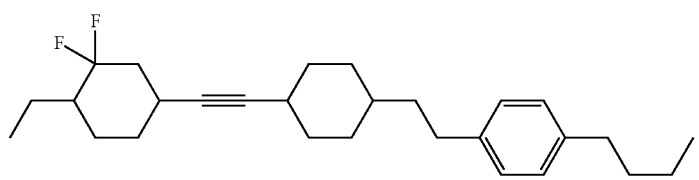 |
| 99 | 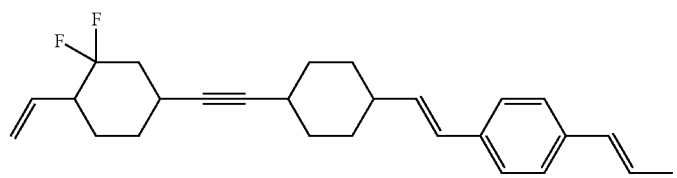 [SMILES: C=CC1CCC(C#CC2CCC(/C=C/c3ccc(/C=C/C)cc3)CC2)CC1(F)F] |

-continued
| No. | |
|---|---|
| 100 | 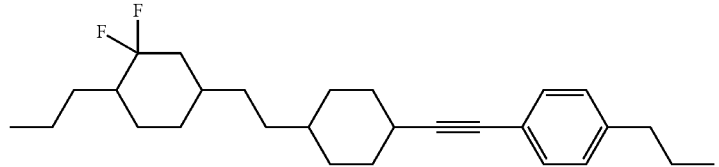 [SMILES: CCCc1ccc(C#CC2CCC(CCC3CCC(CCC)C(F)(F)C3)CC2)cc1] |
| 101 | 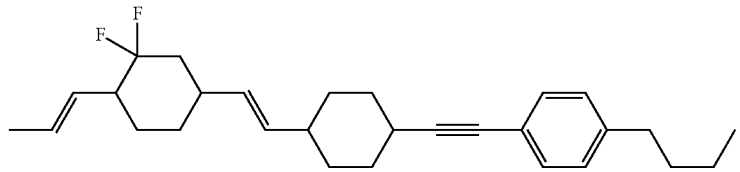 [SMILES: C/C=C/C1CCC(/C=C/C2CCC(C#Cc3ccc(CCCC)cc3)CC2)CC1(F)F] |
| 102 | 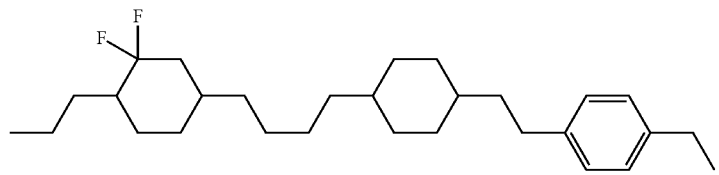 |
| 103 | 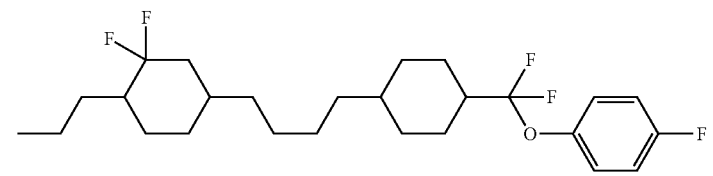 [SMILES: CCCC1CCC(CCCCC2CCC(C(F)(F)Oc3ccc(F)cc3)CC2)CC1(F)F] |
| 104 | 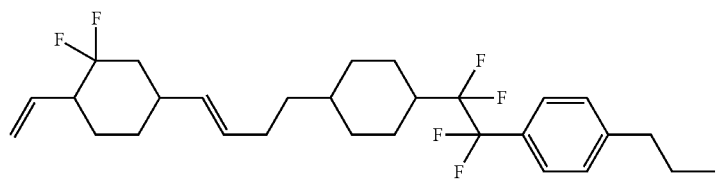 [SMILES: C=CC1CCC(/C=C/CCC2CCC(C(F)(F)C(F)(F)c3ccc(CCC)cc3)CC2)CC1(F)F] |
| 105 | 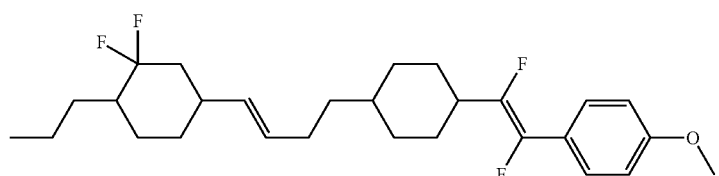 |
| 106 | 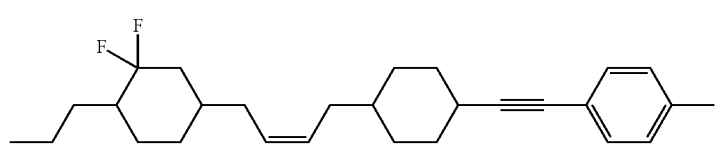 |
| 107 | 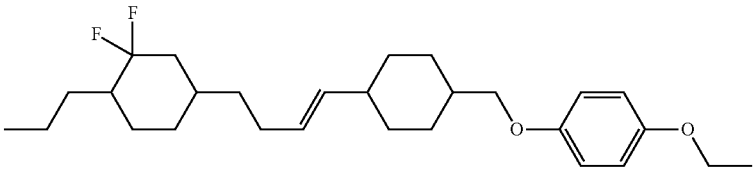 [SMILES: CCCC1CCC(CC/C=C/C2CCC(COc3ccc(OCC)cc3)CC2)CC1(F)F] |
| 108 | 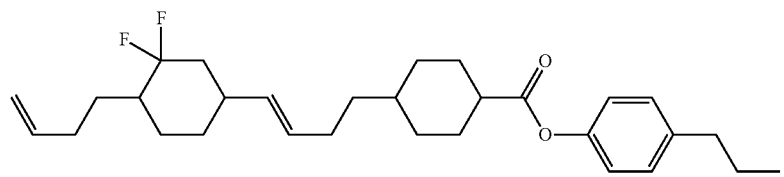 [SMILES: C=CCCC1CCC(/C=C/CCC2CCC(C(=O)Oc3ccc(CCC)cc3)CC2)CC1(F)F] |

-continued
| No. | |
|---|---|
| 109 | 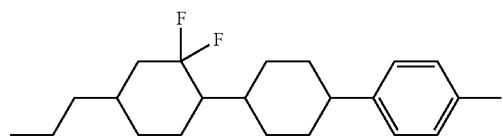  C 62.3 N 145.6 I  NI = 108.4° C., Δε = 3.4, Δn = 0.097, η = 38.9 mPA•m |
| 110 | 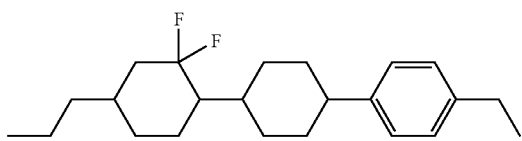 |
| 111 | 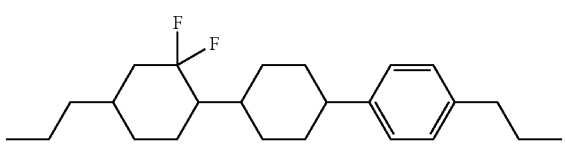 [SMILES: CCCc1ccc(C2CCC(C3CCC(CCC)CC3(F)F)CC2)cc1] |
| 112 | 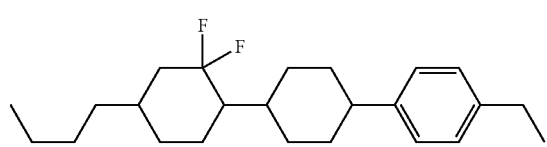 [SMILES: CCCCC1CCC(C2CCC(c3ccc(CC)cc3)CC2)C(F)(F)C1] |
| 113 | 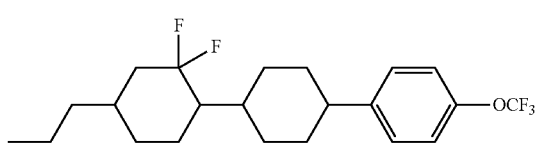 [SMILES: CCCC1CCC(C2CCC(c3ccc(OC(F)(F)F)cc3)CC2)C(F)(F)C1] |
| 114 | 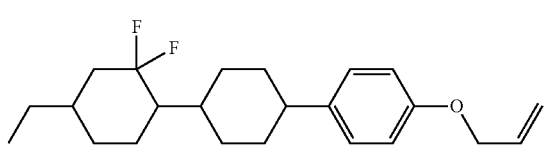 [SMILES: C=CCOc1ccc(C2CCC(C3CCC(CC)CC3(F)F)CC2)cc1] |
| 115 | 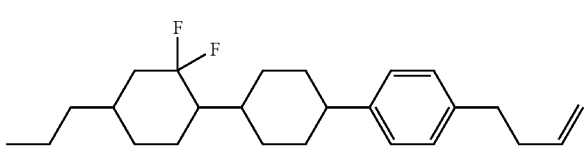 [SMILES: C=CCCc1ccc(C2CCC(C3CCC(CCC)CC3(F)F)CC2)cc1] |
| 116 | 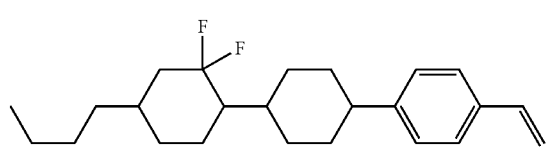 [SMILES: C=Cc1ccc(C2CCC(C3CCC(CCCC)CC3(F)F)CC2)cc1] |
| 117 | 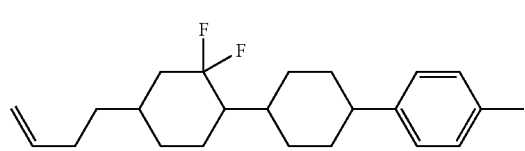 [SMILES: C=CCCC1CCC(C2CCC(c3ccc(C)cc3)CC2)C(F)(F)C1] |
| 118 | 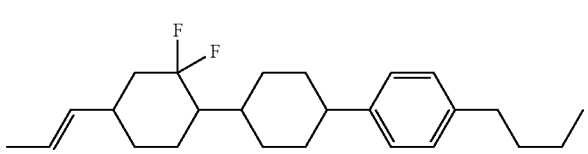 [SMILES: C/C=C/C1CCC(C2CCC(c3ccc(CCCC)cc3)CC2)C(F)(F)C1] |

-continued
| No. | |
|---|---|
| 119 | 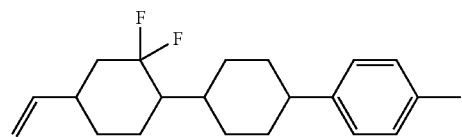 [SMILES: C=CC1CCC(C2CCC(c3ccc(C)cc3)CC2)C(F)(F)C1] |
| 120 | 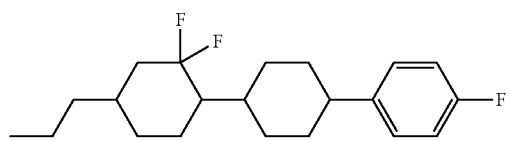 [SMILES: CCCC1CCC(C2CCC(c3ccc(F)cc3)CC2)C(F)(F)C1] |
| 121 | 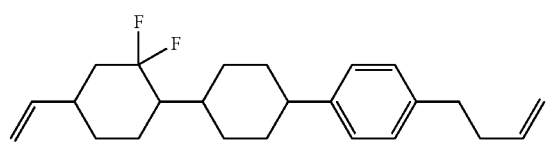 [SMILES: C=CCCc1ccc(C2CCC(C3CCC(C=C)CC3(F)F)CC2)cc1] |
| 122 | 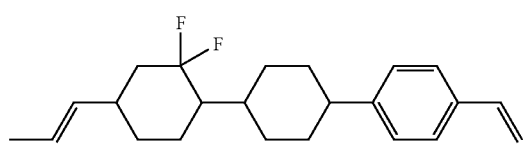 [SMILES: C=Cc1ccc(C2CCC(C3CCC(/C=C/C)CC3(F)F)CC2)cc1] |
| 123 | 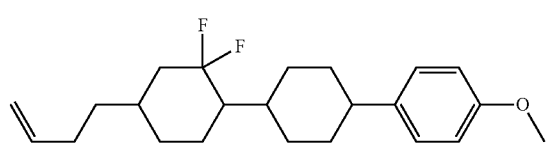 [SMILES: C=CCCC1CCC(C2CCC(c3ccc(OC)cc3)CC2)C(F)(F)C1] |
| 124 | 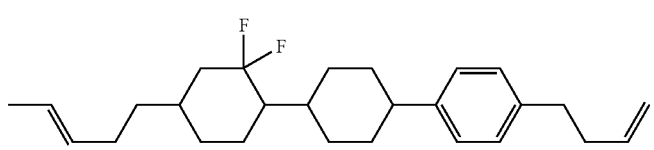 |
| 125 | 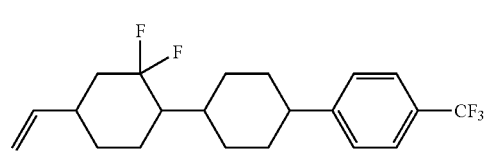 [SMILES: C=CC1CCC(C2CCC(c3ccc(C(F)(F)F)cc3)CC2)C(F)(F)C1] |
| 126 | 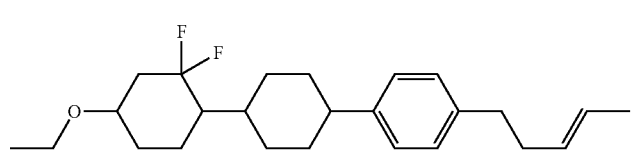 [SMILES: C/C=C/CCc1ccc(C2CCC(C3CCC(OCC)CC3(F)F)CC2)cc1] |
| 127 | 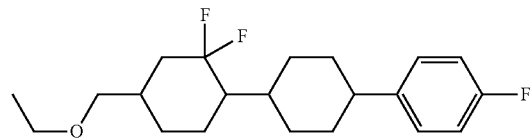 [SMILES: CCOCC1CCC(C2CCC(c3ccc(F)cc3)CC2)C(F)(F)C1] |
| 128 | 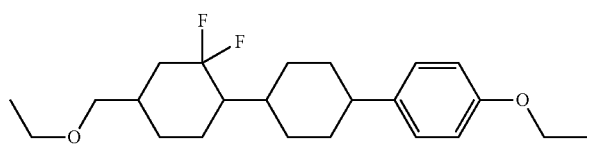 [SMILES: CCOCC1CCC(C2CCC(c3ccc(OCC)cc3)CC2)C(F)(F)C1] |

| No. | |
|---|---|
| 129 | 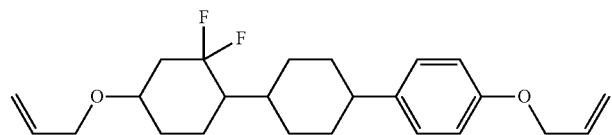 [SMILES: C=CCOc1ccc(C2CCC(C3CCC(OCC=C)CC3(F)F)CC2)cc1] |
| 130 | 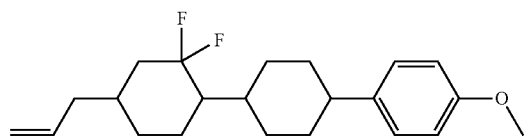 [SMILES: C=CCC1CCC(C2CCC(c3ccc(OC)cc3)CC2)C(F)(F)C1] |
| 131 | 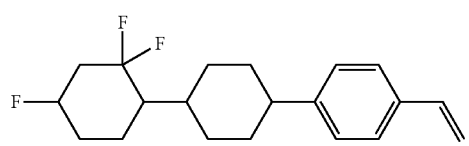 [SMILES: C=Cc1ccc(C2CCC(C3CCC(F)CC3(F)F)CC2)cc1] |
| 132 | 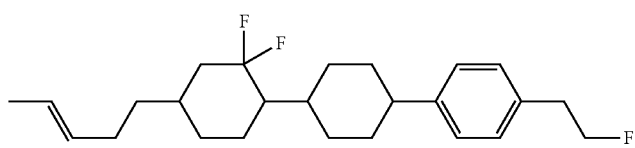 [SMILES: C/C=C/CCC1CCC(C2CCC(c3ccc(CCF)cc3)CC2)C(F)(F)C1] |
| 133 | 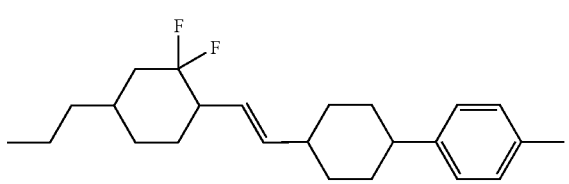 [SMILES: CCCC1CCC(/C=C/C2CCC(c3ccc(C)cc3)CC2)C(F)(F)C1] |
| 134 | 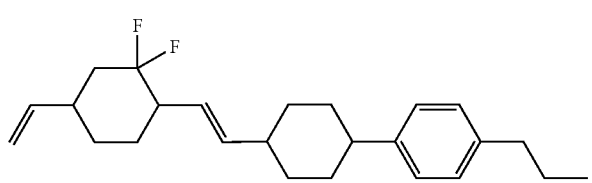 [SMILES: C=CC1CCC(/C=C/C2CCC(c3ccc(CCC)cc3)CC2)C(F)(F)C1] |
| 135 | 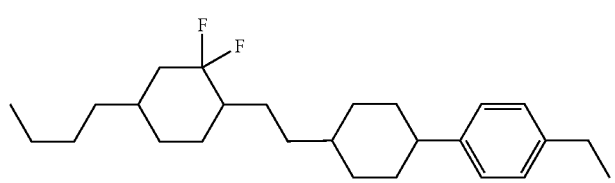 [SMILES: CCCCC1CCC(CCC2CCC(c3ccc(CC)cc3)CC2)C(F)(F)C1] |
| 136 | 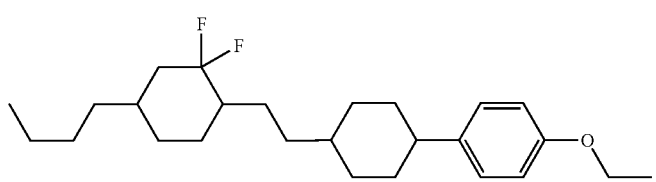 [SMILES: CCCCC1CCC(CCC2CCC(c3ccc(OCC)cc3)CC2)C(F)(F)C1] |
| 137 | 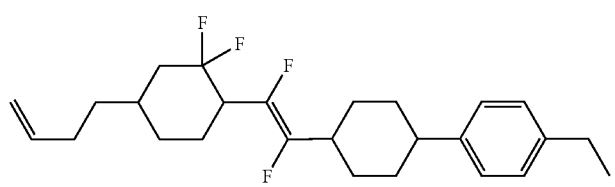 [SMILES: C=CCCC1CCC(/C(F)=C(\F)C2CCC(c3ccc(CC)cc3)CC2)C(F)(F)C1] |

| No. |
|---|
| 138 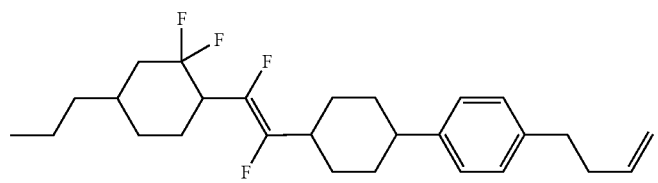 [SMILES: C=CCCc1ccc(C2CCC(/C(F)=C(\F)C3CCC(CCC)CC3(F)F)CC2)cc1] |
| 139 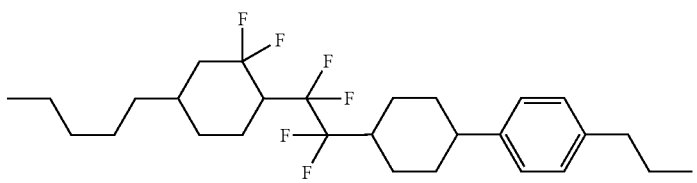 [SMILES: CCCCCC1CCC(C(F)(F)C(F)(F)C2CCC(c3ccc(CCC)cc3)CC2)C(F)(F)C1] |
| 140 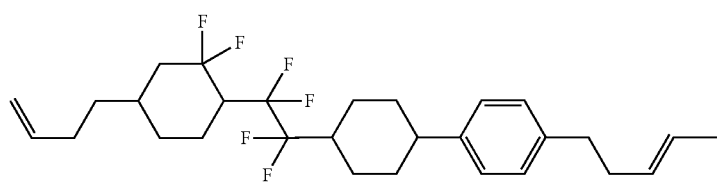 [SMILES: C=CCCC1CCC(C(F)(F)C(F)(F)C2CCC(c3ccc(CC/C=C/C)cc3)CC2)C(F)(F)C1] |
| 141 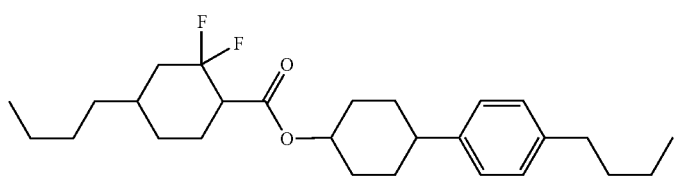 [SMILES: CCCCc1ccc(C2CCC(OC(=O)C3CCC(CCCC)CC3(F)F)CC2)cc1] |
| 142 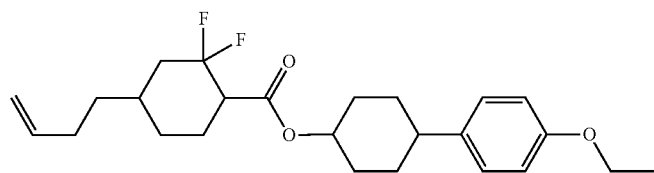 |
| 143 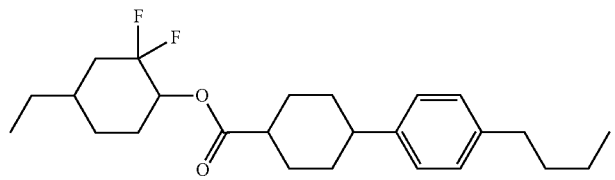 [SMILES: CCCCc1ccc(C2CCC(C(=O)OC3CCC(CC)CC3(F)F)CC2)cc1] |
| 144 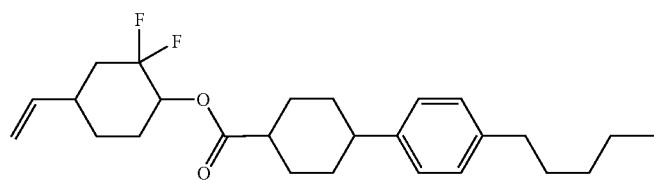 [SMILES: C=CC1CCC(OC(=O)C2CCC(c3ccc(CCCCC)cc3)CC2)C(F)(F)C1] |
| 145 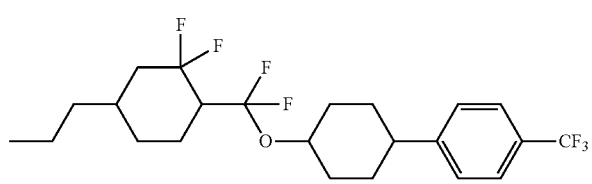 [SMILES: CCCC1CCC(C(F)(F)OC2CCC(c3ccc(C(F)(F)F)cc3)CC2)C(F)(F)C1] |

-continued
| No. | |
|---|---|
| 146 | 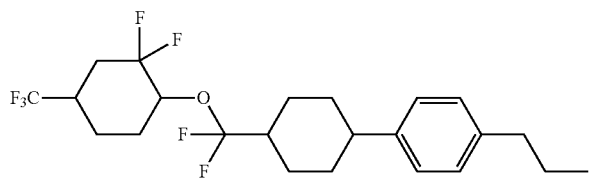 [SMILES: CCCc1ccc(C2CCC(C(F)(F)OC3CCC(C(F)(F)F)CC3(F)F)CC2)cc1] |
| 147 | 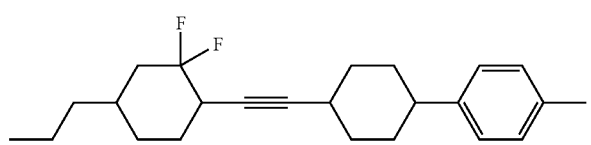 [SMILES: CCCC1CCC(C#CC2CCC(c3ccc(C)cc3)CC2)C(F)(F)C1] |
| 148 | 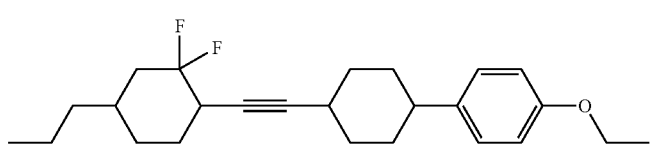 [SMILES: CCCC1CCC(C#CC2CCC(c3ccc(OCC)cc3)CC2)C(F)(F)C1] |
| 149 | 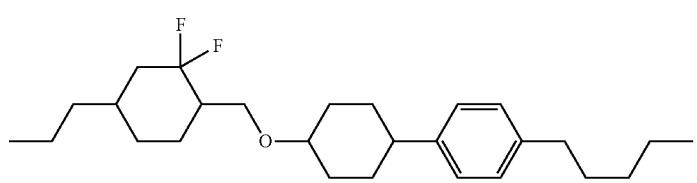 [SMILES: CCCCCc1ccc(C2CCC(OCC3CCC(CCC)CC3(F)F)CC2)cc1] |
| 150 | 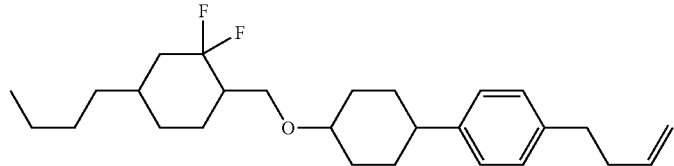 [SMILES: C=CCCc1ccc(C2CCC(OCC3CCC(CCCC)CC3(F)F)CC2)cc1] |
| 151 | 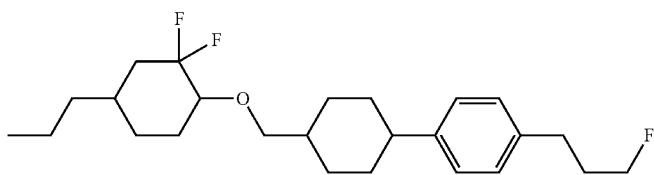 |
| 152 | 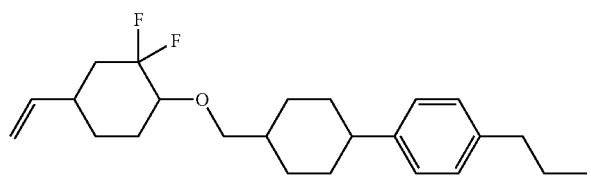 |
| 153 | 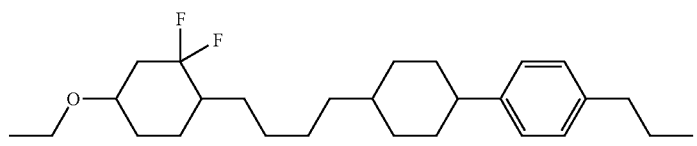 [SMILES: CCCc1ccc(C2CCC(CCCCC3CCC(OCC)CC3(F)F)CC2)cc1] |
| 154 | 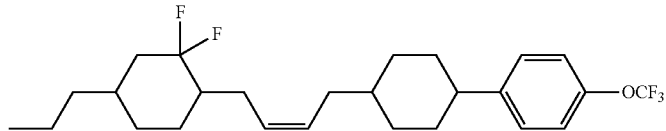 [SMILES: CCCC1CCC(C/C=C\CC2CCC(c3ccc(OC(F)(F)F)cc3)CC2)C(F)(F)C1] |

| No. |  |
|---|---|
| 155 | 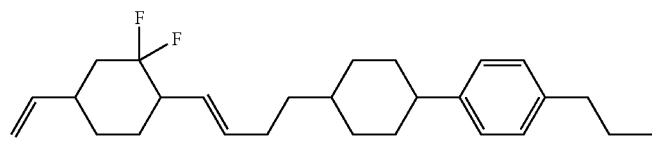 [SMILES: C=CC1CCC(/C=C/CCC2CCC(c3ccc(CCC)cc3)CC2)C(F)(F)C1] |
| 156 | 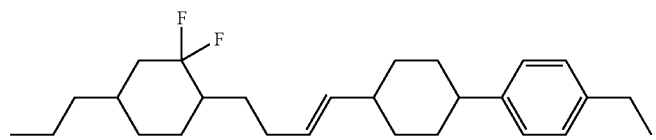 [SMILES: CCCC1CCC(CC/C=C/C2CCC(c3ccc(CC)cc3)CC2)C(F)(F)C1] |
| 157 | 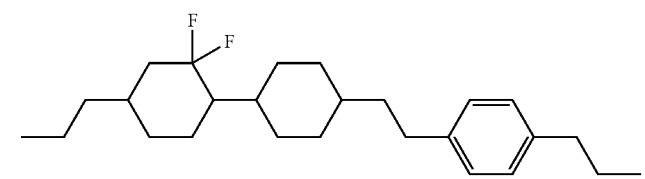 [SMILES: CCCc1ccc(CCC2CCC(C3CCC(CCC)CC3(F)F)CC2)cc1] |
| 158 | 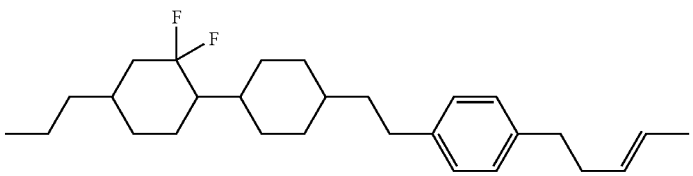 |
| 159 | 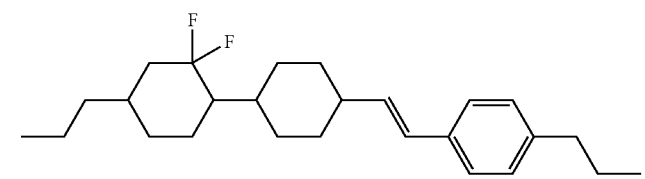 [SMILES: CCCc1ccc(/C=C/C2CCC(C3CCC(CCC)CC3(F)F)CC2)cc1] |
| 160 | 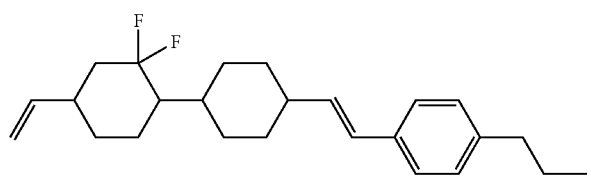 [SMILES: C=CC1CCC(C2CCC(/C=C/c3ccc(CCC)cc3)CC2)C(F)(F)C1] |
| 161 | 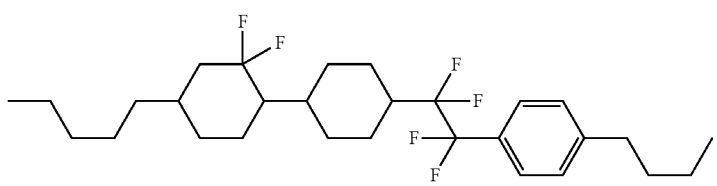 [SMILES: CCCCCC1CCC(C2CCC(C(F)(F)C(F)(F)c3ccc(CCCC)cc3)CC2)C(F)(F)C1] |
| 162 | 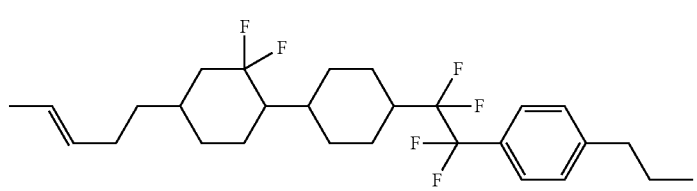 [SMILES: C/C=C/CCC1CCC(C2CCC(C(F)(F)C(F)(F)c3ccc(CCC)cc3)CC2)C(F)(F)C1] |
| 163 | 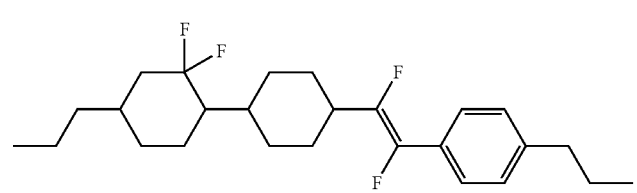 [SMILES: CCCc1ccc(/C(F)=C(\F)C2CCC(C3CCC(CCC)CC3(F)F)CC2)cc1] |

-continued
| No. | |
|---|---|
| 164 | 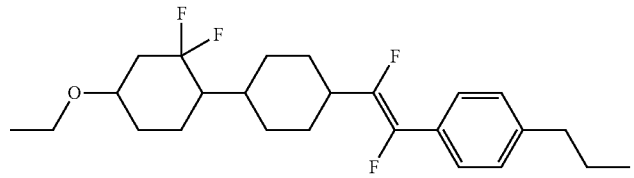 [SMILES: CCCc1ccc(/C(F)=C(\F)C2CCC(C3CCC(OCC)CC3(F)F)CC2)cc1] |
| 165 | 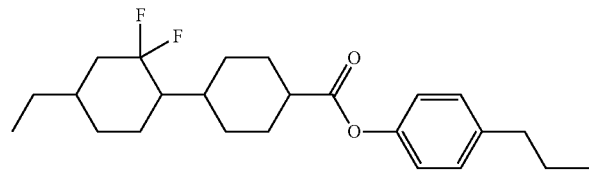 [SMILES: CCCc1ccc(OC(=O)C2CCC(C3CCC(CC)CC3(F)F)CC2)cc1] |
| 166 | 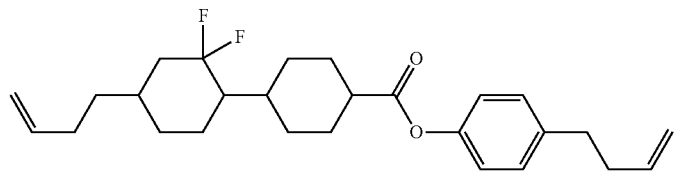 [SMILES: C=CCCc1ccc(OC(=O)C2CCC(C3CCC(CCC=C)CC3(F)F)CC2)cc1] |
| 167 | 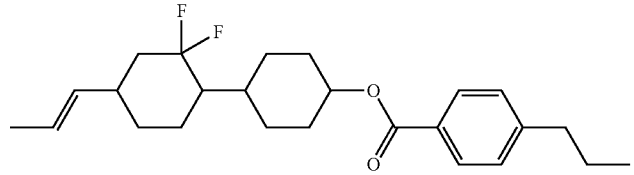 [SMILES: C/C=C/C1CCC(C2CCC(OC(=O)c3ccc(CCC)cc3)CC2)C(F)(F)C1] |
| 168 | 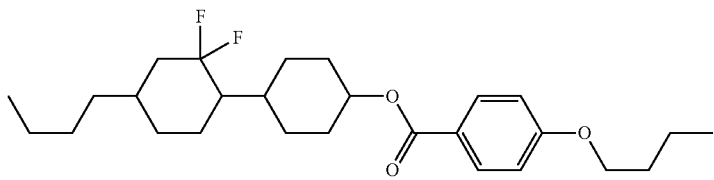 [SMILES: CCCCOc1ccc(C(=O)OC2CCC(C3CCC(CCCC)CC3(F)F)CC2)cc1] |
| 169 | 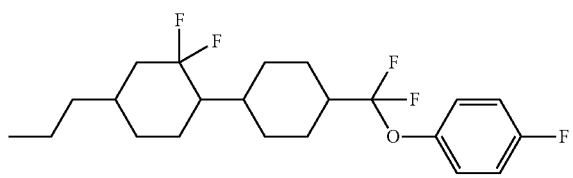 |
| 170 | 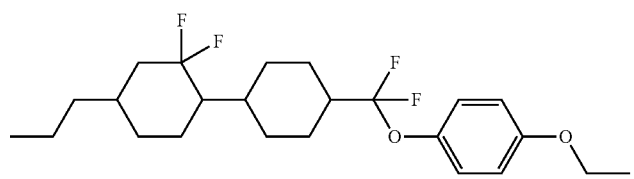 [SMILES: CCCC1CCC(C2CCC(C(F)(F)Oc3ccc(OCC)cc3)CC2)C(F)(F)C1] |
| 171 | 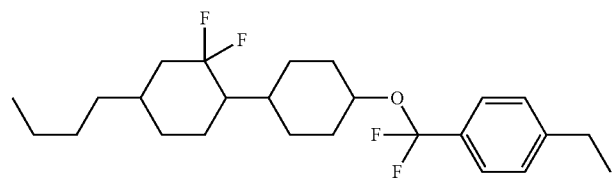 [SMILES: CCCCC1CCC(C2CCC(OC(F)(F)c3ccc(CC)cc3)CC2)C(F)(F)C1] |

| No. | |
|---|---|
| 172 | 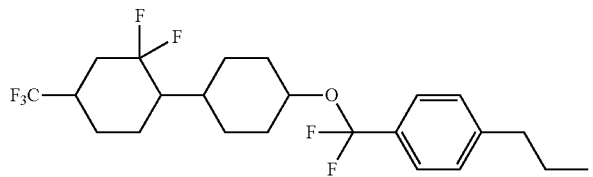 [SMILES: CCCc1ccc(C(F)(F)OC2CCC(C3CCC(C(F)(F)F)CC3(F)F)CC2)cc1] |
| 173 | 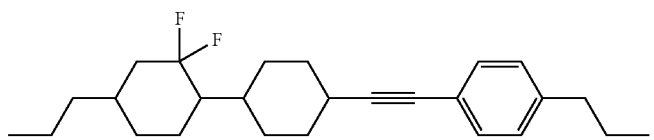 [SMILES: CCCc1ccc(C#CC2CCC(C3CCC(CCC)CC3(F)F)CC2)cc1] |
| 174 | 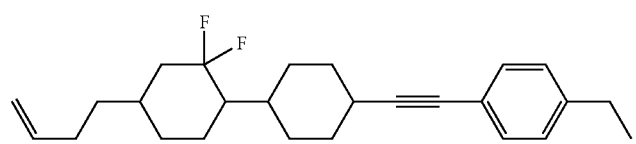 [SMILES: C=CCCC1CCC(C2CCC(C#Cc3ccc(CC)cc3)CC2)C(F)(F)C1] |
| 175 | 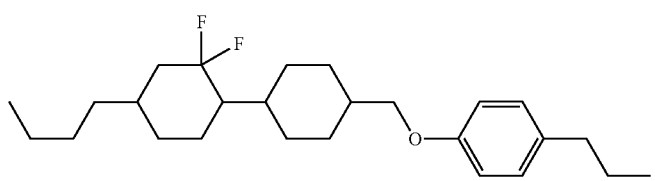 [SMILES: CCCCC1CCC(C2CCC(COc3ccc(CCC)cc3)CC2)C(F)(F)C1] |
| 176 | 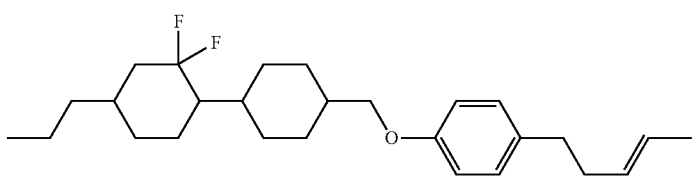 [SMILES: C/C=C/CCc1ccc(OCC2CCC(C3CCC(CCC)CC3(F)F)CC2)cc1] |
| 177 | 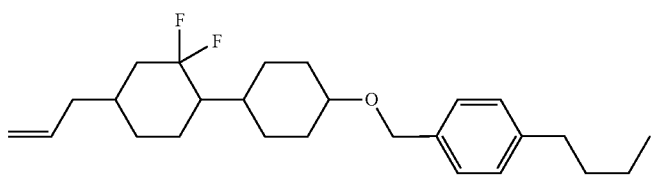 [SMILES: C=CCC1CCC(C2CCC(OCc3ccc(CCCC)cc3)CC2)C(F)(F)C1] |
| 178 | 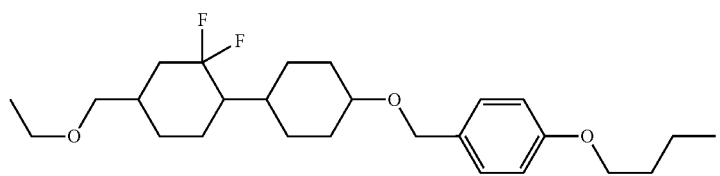 [SMILES: CCCCOc1ccc(COC2CCC(C3CCC(COCC)CC3(F)F)CC2)cc1] |
| 179 | 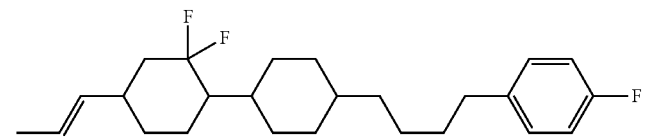 [SMILES: C/C=C/C1CCC(C2CCC(CCCCc3ccc(F)cc3)CC2)C(F)(F)C1] |
| 180 | 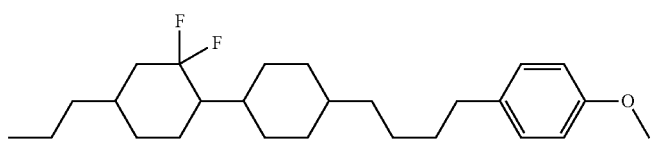 [SMILES: CCCC1CCC(C2CCC(CCCCc3ccc(OC)cc3)CC2)C(F)(F)C1] |

| No. | |
|---|---|
| 181 | 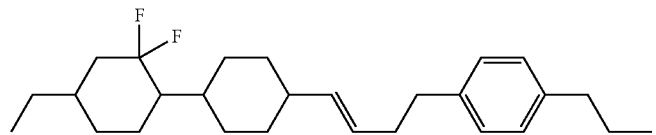 [SMILES: CCCc1ccc(CC/C=C/C2CCC(C3CCC(CC)CC3(F)F)CC2)cc1] |
| 182 | 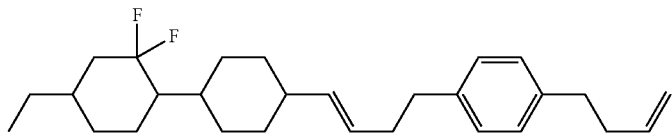 |
| 183 | 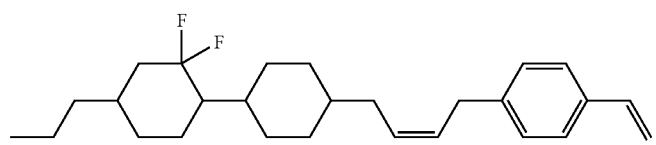 |
| 184 | 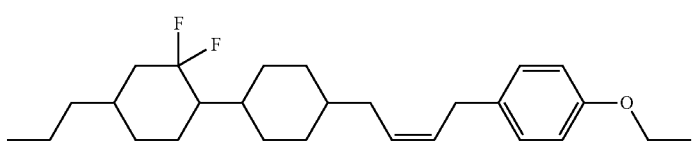 [SMILES: CCCC1CCC(C2CCC(C/C=C\Cc3ccc(OCC)cc3)CC2)C(F)(F)C1] |
| 185 | 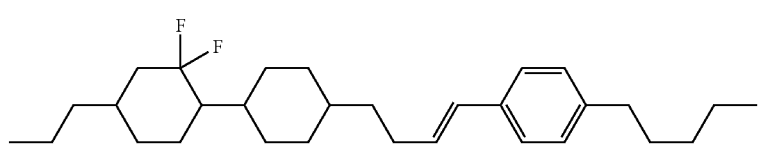 [SMILES: CCCCCc1ccc(/C=C/CCC2CCC(C3CCC(CCC)CC3(F)F)CC2)cc1] |
| 186 | 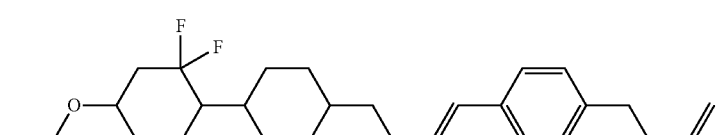 |
| 187 | 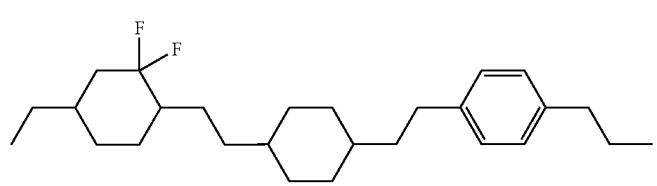 [SMILES: CCCc1ccc(CCC2CCC(CCC3CCC(CC)CC3(F)F)CC2)cc1] |
| 188 | 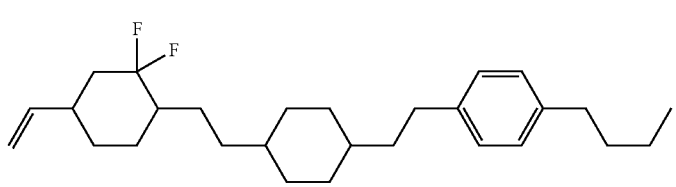 [SMILES: C=CC1CCC(CCC2CCC(CCc3ccc(CCCC)cc3)CC2)C(F)(F)C1] |
| 189 | 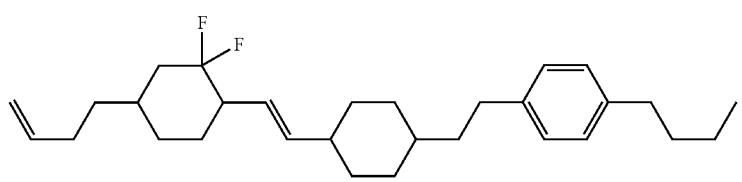 [SMILES: C=CCCC1CCC(/C=C/C2CCC(CCc3ccc(CCCC)cc3)CC2)C(F)(F)C1] |
| 190 | 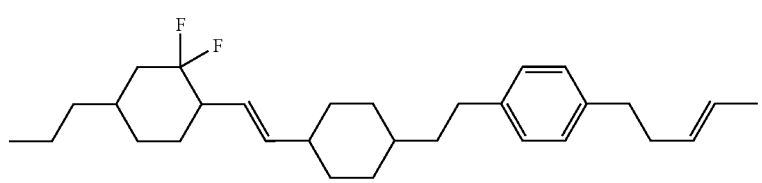 [SMILES: C/C=C/CCc1ccc(CCC2CCC(/C=C/C3CCC(CCC)CC3(F)F)CC2)cc1] |

-continued
| No. | |
|---|---|
| 191 | 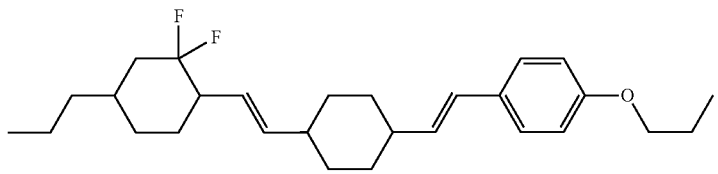 [SMILES: CCCOc1ccc(/C=C/C2CCC(/C=C/C3CCC(CCC)CC3(F)F)CC2)cc1] |
| 192 | 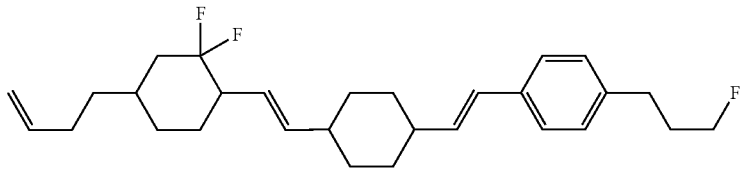 [SMILES: C=CCCC1CCC(/C=C/C2CCC(/C=C/c3ccc(CCCF)cc3)CC2)C(F)(F)C1] |
| 193 | 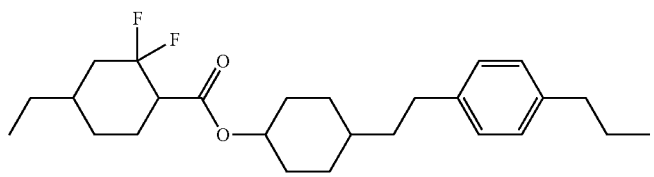 [SMILES: CCCc1ccc(CCC2CCC(OC(=O)C3CCC(CC)CC3(F)F)CC2)cc1] |
| 194 | 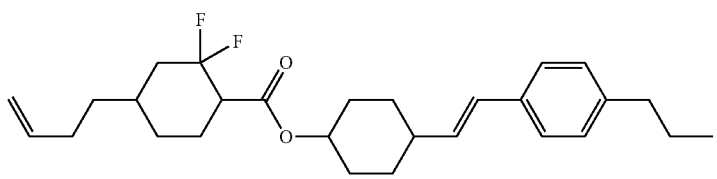 [SMILES: C=CCCC1CCC(C(=O)OC2CCC(/C=C/c3ccc(CCC)cc3)CC2)C(F)(F)C1] |
| 195 | 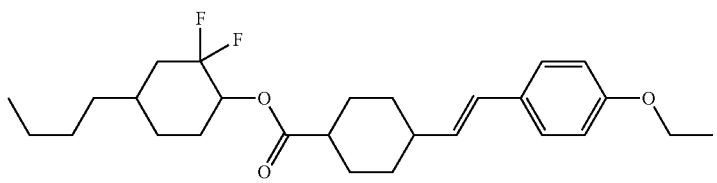 [SMILES: CCCCC1CCC(OC(=O)C2CCC(/C=C/c3ccc(OCC)cc3)CC2)C(F)(F)C1] |
| 196 | 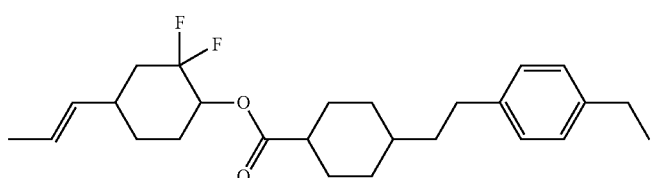 |
| 197 | 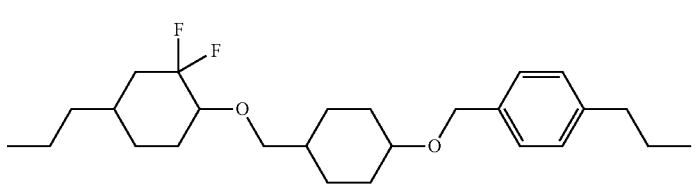 [SMILES: CCCc1ccc(COC2CCC(COC3CCC(CCC)CC3(F)F)CC2)cc1] |
| 198 | 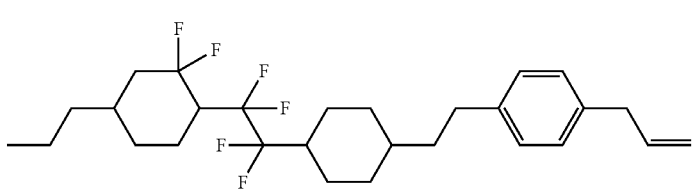 [SMILES: C=CCc1ccc(CCC2CCC(C(F)(F)C(F)(F)C3CCC(CCC)CC3(F)F)CC2)cc1] |

| No. | |
|---|---|
| 199 | 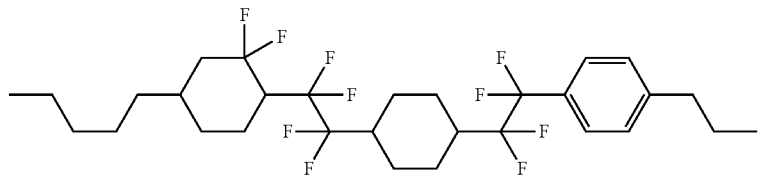 [SMILES: CCCCCC1CCC(C(F)(F)C(F)(F)C2CCC(C(F)(F)C(F)(F)c3ccc(CCC)cc3)CC2)C(F)(F)C1] |
| 200 | 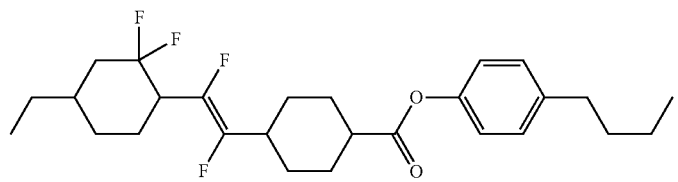 [SMILES: CCCCc1ccc(OC(=O)C2CCC(/C(F)=C(\F)C3CCC(CC)CC3(F)F)CC2)cc1] |
| 201 | 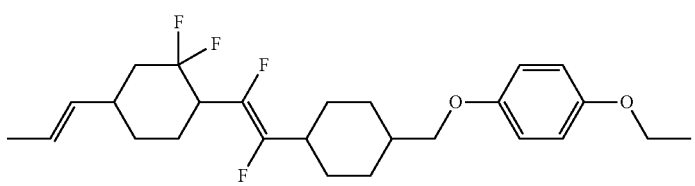 [SMILES: C/C=C/C1CCC(/C(F)=C(\F)C2CCC(COc3ccc(OCC)cc3)CC2)C(F)(F)C1] |
| 202 | 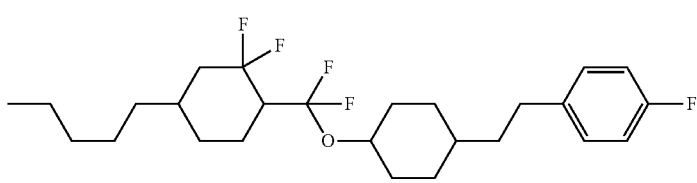 [SMILES: CCCCCC1CCC(C(F)(F)OC2CCC(CCc3ccc(F)cc3)CC2)C(F)(F)C1] |
| 203 | 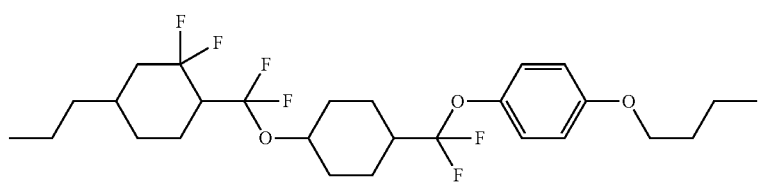 [SMILES: CCCCOc1ccc(OC(F)(F)C2CCC(OC(F)(F)C3CCC(CCC)CC3(F)F)CC2)cc1] |
| 204 | 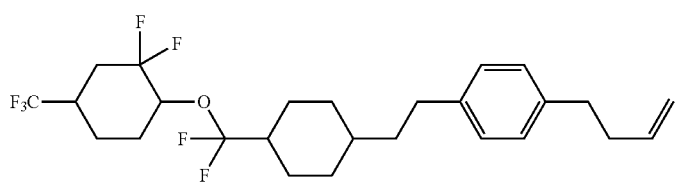 [SMILES: C=CCCc1ccc(CCC2CCC(C(F)(F)OC3CCC(C(F)(F)F)CC3(F)F)CC2)cc1] |
| 205 | 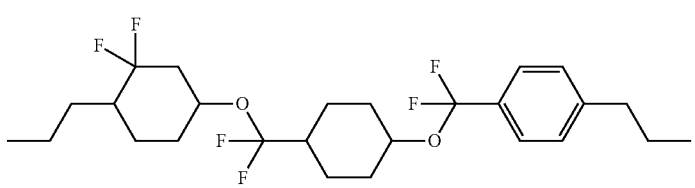 [SMILES: CCCc1ccc(C(F)(F)OC2CCC(C(F)(F)OC3CCC(CCC)C(F)(F)C3)CC2)cc1] |
| 206 | 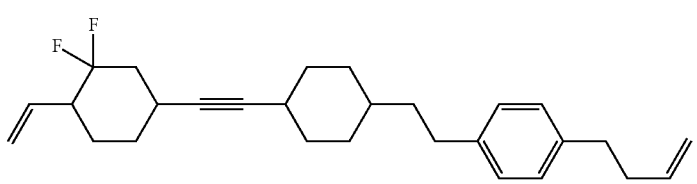 [SMILES: C=CCCc1ccc(CCC2CCC(C#CC3CCC(C=C)C(F)(F)C3)CC2)cc1] |

-continued
| No. |
|---|
| 207 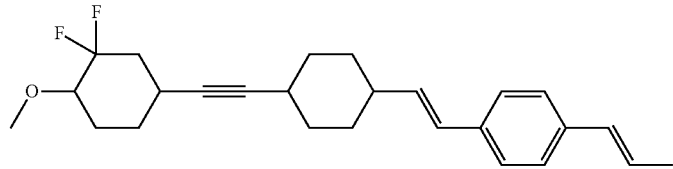 [SMILES: C/C=C/c1ccc(/C=C/C2CCC(C#CC3CCC(OC)C(F)(F)C3)CC2)cc1] |
| 208 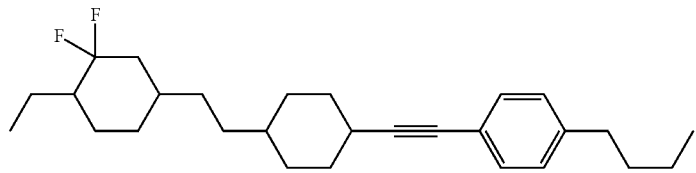 [SMILES: CCCCc1ccc(C#CC2CCC(CCC3CCC(CC)C(F)(F)C3)CC2)cc1] |
| 209 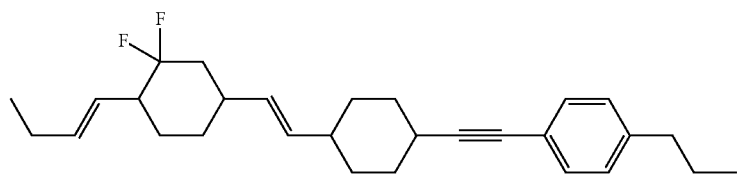 |
| 210 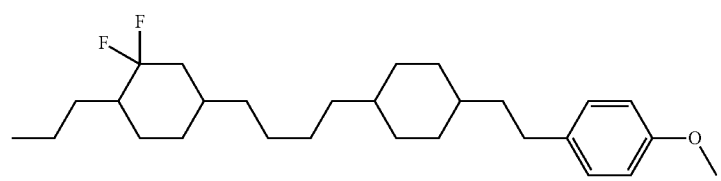 |
| 211 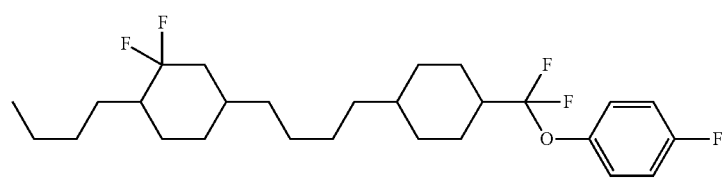 [SMILES: CCCCC1CCC(CCCCC2CCC(C(F)(F)Oc3ccc(F)cc3)CC2)CC1(F)F] |
| 212 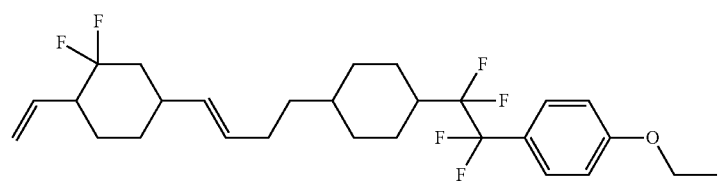 [SMILES: C=CC1CCC(/C=C/CCC2CCC(C(F)(F)C(F)(F)c3ccc(OCC)cc3)CC2)CC1(F)F] |
| 213 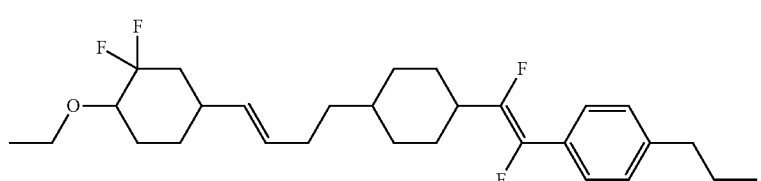 |
| 214 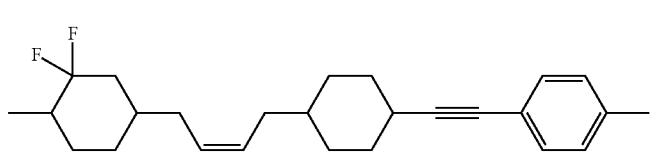 |
| 215 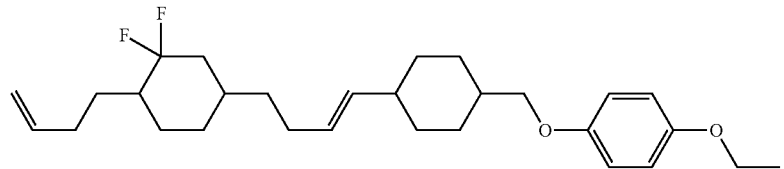 [SMILES: C=CCCC1CCC(CC/C=C/C2CCC(COc3ccc(OCC)cc3)CC2)CC1(F)F] |

-continued

| No. | |
|---|---|
| 216 | 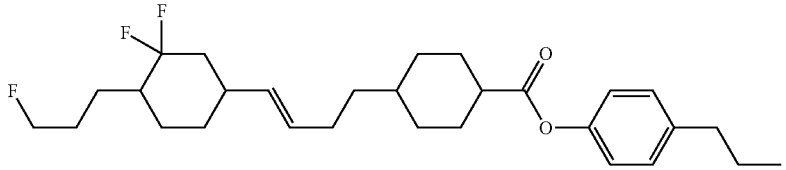 |

2. Examples of the Composition

The invention will be explained in more detail by way of examples. The invention includes a mixture of the composition in Use example 1 and the composition in Use example 2. The invention also includes a mixture prepared by mixing at least two of the compositions in Use examples. The compounds described in Use Examples were expressed in terms of symbols based on the definition in Table 5 described below. In Table 5, the configuration of 1,4-cyclohexylene is trans. A parenthesized number next to a symbolized compound in Use Example represents the chemical formula to which the compound belongs. The symbol "(-)" means a liquid crystal compound that is different from compounds (2) to (15). The ratio (percentage) of a liquid crystal compound means the percentages by weight (% by weight) based on the weight of the liquid crystal composition. Last, the physical property-values of the composition were summarized. Physical properties were measured according to the method described above, and the measured value was reported as it was (without extrapolation).

TABLE 5

Method of Description of Compounds using Symbols
R—(A$_1$)—Z$_1$—. . . —Z$_n$—(A$_n$)—R'

| 1) Left-terminal Group R— | Symbol |
|---|---|
| FC$_n$H$_{2n}$— | Fn- |
| C$_n$H$_{2n+1}$— | n- |
| C$_n$H$_{2n+1}$O— | nO— |
| C$_m$H$_{2m+1}$OC$_n$O$_{2n}$— | mOn- |
| CH$_2$=CH— | V— |
| C$_n$H$_{2n+1}$—CH=CH— | nV— |
| CH$_2$=CH—C$_n$H$_{2n}$— | Vn- |
| C$_m$H$_{2m+1}$—C=CH—C$_n$C$_{2n}$— | mVn- |
| CF$_2$=CH— | VFF— |
| CF$_2$=CH—C$_n$H$_{2n}$— | VFFn- |
| 2) Right-terminal Group —R' | Symbol |
| —C$_n$H$_{2n+1}$ | -n |
| —OC$_n$H$_{2n+1}$ | —On |
| —COOCH$_3$ | —EMe |
| —CH=CH$_2$ | —V |
| —CH=CH—C$_n$H$_{2n+1}$ | —Vn |
| —C$_n$H$_{2n}$—CH=CH$_2$ | -nV |
| —C$_m$H$_{2m}$—CH=CH—C$_n$H$_{2n+1}$ | -mVn |
| —CH=CF$_2$ | —VFF |
| —F | —F |
| —Cl | —CL |
| —OCF$_3$ | —OCF3 |
| —OCF$_2$H | —OCF2H |
| —CF$_3$ | —CF3 |
| —OCF$_2$—CF=CF—CF$_3$ | —OCF2FVFCF3 |
| —C≡N | —C |
| 3) Bonding Group —Z$_n$— | Symbol |
| —C$_n$H$_{2n}$— | n |
| —COO— | E |
| —CH=CH— | V |

TABLE 5-continued

Method of Description of Compounds using Symbols
R—(A$_1$)—Z$_1$—. . . —Z$_n$—(A$_n$)—R'

| | |
|---|---|
| —CH$_2$O— | 1O |
| —OCH$_2$— | O1 |
| —CF$_2$O— | X |
| —C≡C— | T |
| 4) Ring Structure —A$_n$— | Symbol |
| cyclohexane | H |
| benzene | B |
| fluorobenzene | B(F) |
| 2-fluorobenzene | B(2F) |
| difluorobenzene | B(F,F) |
| 2,5-difluorobenzene | B(2F,5F) |
| 2,3-difluorobenzene | B(2F,3F) |
| dioxane | G |

TABLE 5-continued

Method of Description of Compounds using Symbols
R—(A₁)—Z₁—...—Zₙ—(Aₙ)—R'

 dh

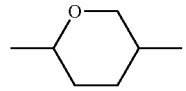 Dh

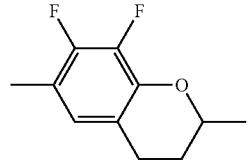 Cro(7F,8F)

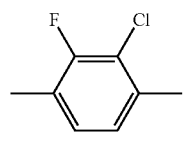 B(2F,3CL)

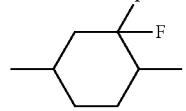 H(3F2)

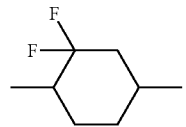 H(2F2)

5) Examples of Description

Example 1. 3-H(3F2)HB-1

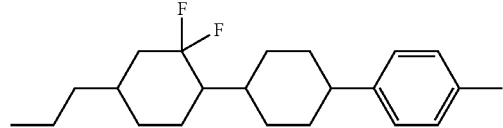

Example 2. 3-HBB(F,F)-F

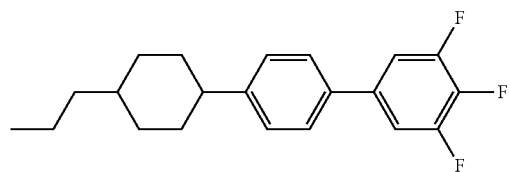

Use Example 1

| | | |
|---|---|---|
| 3-H(3F2)HB-1 | (No. 109) | 5% |
| 2-HB-C | (5-1) | 5% |
| 3-HB-C | (5-1) | 12% |
| 3-HB-O2 | (13-5) | 15% |
| 2-BTB-1 | (13-10) | 3% |
| 3-HHB-F | (3-1) | 4% |
| 3-HHB-1 | (14-1) | 8% |
| 3-HHB-O1 | (14-1) | 5% |
| 3-HHB-3 | (14-1) | 14% |
| 3-HHEB-F | (3-10) | 2% |
| 5-HHEB-F | (3-10) | 2% |
| 2-HHB(F)-F | (3-2) | 7% |
| 3-HHB(F)-F | (3-2) | 6% |
| 5-HHB(F)-F | (3-2) | 7% |
| 3-HHB(F,F)-F | (3-3) | 5% |

NI = 95.3° C.; η = 16.3 mPa · s: Δn = 0.098; Δε = 4.5.

Use Example 2

| | | |
|---|---|---|
| V-H(3F2)HB-1 | (No. 119) | 4% |
| 3-HB-CL | (2-2) | 13% |
| 3-HH-4 | (13-1) | 10% |
| 3-HB-O2 | (13-5) | 7% |
| 3-HHB(F,F)-F | (3-3) | 3% |
| 3-HBB(F,F)-F | (3-3) | 29% |
| 5-HBB(F,F)-F | (3-3) | 24% |
| 5-HBB(F)B-2 | (15-5) | 5% |
| 5-HBB(F)B-3 | (15-5) | 5% |

Use Example 3

| | | |
|---|---|---|
| 3-H(3F2)HB-2V | (No. 115) | 5% |
| 7-HB(F,F)-F | (2-4) | 3% |
| 3-HB-O2 | (13-5) | 7% |
| 2-HHB(F)-F | (3-2) | 10% |
| 3-HHB(F)-F | (3-2) | 10% |
| 5-HHB(F)-F | (3-2) | 10% |
| 2-HBB(F)-F | (3-23) | 9% |
| 3-HBB(F)-F | (3-23) | 10% |
| 5-HBB(F)-F | (3-23) | 10% |
| 2-HBB-F | (3-22) | 4% |
| 3-HBB-F | (3-22) | 4% |
| 5-HBB-F | (3-22) | 3% |
| 3-HBB(F,F)-F | (3-24) | 5% |
| 5-HBB(F,F)-F | (3-24) | 10% |

Use Example 4

| | | |
|---|---|---|
| 3-H(3F2)HB-1 | (No. 109) | 4% |
| 5-HB-CL | (2-2) | 16% |
| 3-HH-4 | (13-1) | 11% |
| 3-HH-5 | (13-1) | 4% |
| 3-HHB-F | (3-1) | 4% |
| 3-HHB-CL | (3-1) | 3% |
| 4-HHB-CL | (3-1) | 4% |
| 3-HHB(F)-F | (3-2) | 10% |
| 4-HHB(F)-F | (3-2) | 9% |
| 5-HHB(F)-F | (3-2) | 9% |
| 7-HHB(F)-F | (3-2) | 8% |
| 5-HBB(F)-F | (3-23) | 4% |
| 3-HHBB(F,F)-F | (4-6) | 2% |
| 4-HHBB(F,F)-F | (4-6) | 3% |
| 5-HHBB(F,F)-F | (4-6) | 3% |
| 3-HH2BB(F,F)-F | (4-15) | 3% |
| 4-HH2BB(F,F)-F | (4-15) | 3% |

NI = 111.0° C.; η = 19.2 mPa · s: Δn = 0.089; Δε = 3.9.

Use Example 5

| | | |
|---|---|---|
| V-H(3F2)HB-1 | (No. 119) | 5% |
| 3-HHB(F,F)-F | (3-3) | 9% |
| 3-H2HB(F,F)-F | (3-15) | 7% |
| 4-H2HB(F,F)-F | (3-15) | 8% |
| 5-H2HB(F,F)-F | (3-15) | 7% |
| 3-HBB(F,F)-F | (3-24) | 21% |
| 5-HBB(F,F)-F | (3-24) | 20% |
| 3-H2BB(F,F)-F | (3-27) | 8% |
| 5-HHBB(F,F)-F | (4-6) | 3% |
| 5-HHEBB-F | (4-17) | 2% |
| 3-HH2BB(F,F)-F | (4-15) | 3% |
| 1O1-HBBH-4 | (15-1) | 3% |
| 1O1-HBBH-5 | (15-1) | 4% |

Use Example 6

| | | |
|---|---|---|
| 3-H(3F2)HB-2V | (No. 115) | 5% |
| 5-HB-F | (2-2) | 12% |
| 6-HB-F | (2-2) | 9% |
| 7-HB-F | (2-2) | 7% |
| 2-HHB-OCF3 | (3-1) | 5% |
| 3-HHB-OCF3 | (3-1) | 6% |
| 4-HHB-OCF3 | (3-1) | 7% |
| 5-HHB-OCF3 | (3-1) | 5% |
| 3-HH2B-OCF3 | (3-4) | 3% |
| 5-HH2B-OCF3 | (3-4) | 4% |
| 3-HHB(F,F)-OCF2H | (3-3) | 4% |
| 3-HHB(F,F)-OCF3 | (3-3) | 4% |
| 3-HH2B(F)-F | (3-5) | 3% |
| 3-HBB(F)-F | (3-2) | 10% |
| 5-HBB(F)-F | (3-2) | 10% |
| 5-HBBH-3 | (15-1) | 3% |
| 3-HB(F)BH-3 | (15-2) | 3% |

Use Example 7

| | | |
|---|---|---|
| 3-H(3F2)HB-1 | (No. 109) | 4% |
| 5-HB-CL | (2-2) | 11% |
| 3-HH-4 | (13-1) | 8% |
| 3-HHB-1 | (14-1) | 5% |
| 3-HHB(F,F)-F | (3-3) | 8% |
| 3-HBB(F,F)-F | (3-24) | 19% |
| 5-HBB(F,F)-F | (3-24) | 14% |
| 3-HHEB(F,F)-F | (3-12) | 8% |
| 4-HHEB(F,F)-F | (3-12) | 4% |
| 5-HHEB(F,F)-F | (3-12) | 3% |
| 2-HBEB(F,F)-F | (3-39) | 3% |
| 3-HBEB(F,F)-F | (3-39) | 5% |
| 5-HBEB(F,F)-F | (3-39) | 3% |
| 3-HHBB(F,F)-F | (4-6) | 5% |

NI = 80.6° C.; η = 22.0 mPa · s: Δn = 0.102; Δε = 8.4.

Use Example 8

| | | |
|---|---|---|
| V-H(3F2)HB-1 | (No. 119) | 5% |
| 3-HB-CL | (2-2) | 6% |
| 5-HB-CL | (2-2) | 4% |
| 3-HHB-OCF3 | (3-1) | 5% |
| 3-H2HB-OCF3 | (3-13) | 5% |
| 5-H4HB-OCF3 | (3-19) | 15% |
| V-HHB(F)-F | (3-2) | 3% |
| 3-HHB(F)-F | (3-2) | 4% |
| 5-HHB(F)-F | (3-2) | 5% |
| 3-H4HB(F,F)-CF3 | (3-21) | 8% |
| 5-H4HB(F,F)-CF3 | (3-21) | 10% |
| 5-H2HB(F,F)-F | (3-15) | 5% |
| 5-H4HB(F,F)-F | (3-21) | 7% |
| 2-H2BB(F)-F | (3-26) | 5% |
| 3-H2BB(F)-F | (3-26) | 8% |
| 3-HBEB(F,F)-F | (3-39) | 5% |

Use Example 9

| | | |
|---|---|---|
| 3-H(3F2)HB-2V | (No. 115) | 3% |
| 5-HB-CL | (2-2) | 16% |
| 7-HB(F,F)-F | (2-4) | 5% |
| 3-HH-4 | (13-1) | 9% |
| 3-HH-5 | (13-1) | 5% |
| 3-HB-O2 | (13-5) | 14% |
| 3-HHB-1 | (14-1) | 8% |
| 3-HHB-O1 | (14-1) | 4% |
| 2-HHB(F)-F | (3-2) | 6% |
| 3-HHB(F)-F | (3-2) | 7% |
| 5-HHB(F)-F | (3-2) | 6% |
| 3-HHB(F,F)-F | (3-3) | 6% |
| 3-H2HB(F,F)-F | (3-15) | 6% |
| 4-H2HB(F,F)-F | (3-15) | 5% |

Use Example 10

| | | |
|---|---|---|
| 3-H(3F2)HB-1 | (No. 109) | 5% |
| 5-HB-CL | (2-2) | 3% |
| 7-HB(F)-F | (2-3) | 7% |
| 3-HH-4 | (13-1) | 9% |
| 3-HH-5 | (13-1) | 10% |
| 3-HB-O2 | (13-5) | 13% |
| 3-HHEB-F | (3-10) | 8% |
| 5-HHEB-F | (3-10) | 8% |
| 3-HHEB(F,F)-F | (3-12) | 8% |
| 4-HHEB(F,F)-F | (3-12) | 3% |
| 3-GHB(F,F)-F | (3-109) | 5% |
| 4-GHB(F,F)-F | (3-109) | 6% |
| 5-GHB(F,F)-F | (3-109) | 5% |
| 2-HHB(F,F)-F | (3-3) | 5% |
| 3-HHB(F,F)-F | (3-3) | 5% |

NI = 72.2° C.; η = 18.0 mPa · s: Δn = 0.068; Δε = 5.3.

Use Example 11

| | | |
|---|---|---|
| V-H(3F2)HB-1 | (No. 119) | 3% |
| 3-HB-O1 | (13-5) | 12% |
| 3-HH-4 | (13-1) | 5% |
| 3-HB-O2 | (13-5) | 4% |
| 3-HB(2F,3F)-O2 | (6-1) | 12% |
| 5-HB(2F,3F)-O2 | (6-1) | 12% |
| 2-HHB(2F,3F)-1 | (7-1) | 12% |
| 3-HHB(2F,3F)-1 | (7-1) | 10% |
| 3-HHB(2F,3F)-O2 | (7-1) | 11% |
| 5-HHB(2F,3F)-O2 | (7-1) | 12% |
| 3-HHB-1 | (14-1) | 7% |

Use Example 12

| | | |
|---|---|---|
| 3-H(3F2)HB-2V | (No. 115) | 7% |
| 2-HH-5 | (13-1) | 3% |
| 3-HH-4 | (13-1) | 15% |

| | | |
|---|---|---|
| 3-HH-5 | (13-1) | 3% |
| 3-HB-O2 | (13-5) | 12% |
| 3-H2B(2F,3F)-O2 | (6-4) | 13% |
| 5-H2B(2F,3F)-O2 | (6-4) | 14% |
| 3-HHB(2F,3CL)-O2 | (7-1) | 5% |
| 2-HBB(2F,3F)-O2 | (7-7) | 3% |
| 3-HBB(2F,3F)-O2 | (7-7) | 8% |
| 5-HBB(2F,3F)-O2 | (7-7) | 8% |
| 3-HHB-1 | (14-1) | 3% |
| 3-HHB-3 | (14-1) | 3% |
| 3-HHB-O1 | (14-1) | 3% |

Use Example 13

| | | |
|---|---|---|
| 3-H(3F2)HB-1 | (No. 109) | 6% |
| 2-HH-3 | (13-1) | 19% |
| 3-HH-4 | (13-1) | 9% |
| 1-BB-3 | (13-8) | 8% |
| 3-HB-O2 | (13-5) | 2% |
| 3-BB(2F,3F)-O2 | (6-3) | 8% |
| 5-BB(2F,3F)-O2 | (6-3) | 6% |
| 2-HH1OB(2F,3F)-O2 | (7-5) | 13% |
| 3-HH1OB(2F,3F)-O2 | (7-5) | 19% |
| 3-HHB-1 | (14-1) | 5% |
| 3-HHB-O1 | (14-1) | 3% |
| 2-BBB(2F)-5 | (14-8) | 2% |

NI = 77.6° C.; η = 16.6 mPa · s: Δn = 0.097; Δε = −3.0.

Use Example 14

| | | |
|---|---|---|
| V-H(3F2)HB-1 | (No. 119) | 5% |
| 2-HH-3 | (13-1) | 16% |
| 3-HH-4 | (13-1) | 5% |
| 7-HB-1 | (13-5) | 5% |
| 5-HB-O2 | (13-5) | 8% |
| 3-HB(2F,3F)-O2 | (6-1) | 17% |
| 5-HB(2F,3F)-O2 | (6-1) | 16% |
| 4-HHB(2F,3CL)-O2 | (7-1) | 3% |
| 3-HH1OCro(7F,8F)-5 | (10-6) | 5% |
| 5-HBB(F)B-2 | (15-5) | 10% |
| 5-HBB(F)B-3 | (15-5) | 10% |

Use Example 15

| | | |
|---|---|---|
| 3-H(3F2)HB-2V | (No. 115) | 4% |
| 1-BB-3 | (13-8) | 10% |
| 3-HH-V | (13-1) | 29% |
| 3-BB(2F,3F)-O2 | (6-3) | 9% |
| 2-HH1OB(2F,3F)-O2 | (7-5) | 20% |
| 3-HH1OB(2F,3F)-O2 | (7-5) | 14% |
| 3-HHB-1 | (14-1) | 8% |
| 2-BBB(2F)-5 | (14-8) | 6% |

Use Example 16

| | | |
|---|---|---|
| 3-H(3F2)HB-1 | (No. 109) | 7% |
| 2-HH-3 | (13-1) | 6% |
| 3-HH-V1 | (13-1) | 10% |
| 1V2-HH-1 | (13-1) | 8% |
| 1V2-HH-3 | (13-1) | 7% |
| 3-BB(2F,3F)-O2 | (6-3) | 8% |
| 5-BB(2F,3F)-O2 | (6-3) | 4% |
| 2-HH1OB(2F,3F)-O2 | (7-5) | 8% |
| 3-HH1OB(2F,3F)-O2 | (7-5) | 19% |
| 3-HDhB(2F,3F)-O2 | (7-3) | 7% |
| 3-HHB-1 | (14-1) | 3% |
| 3-HHB-3 | (14-1) | 2% |
| 2-BB(2F,3F)B-3 | (8-1) | 11% |

NI = 92.0° C.; η = 22.0 mPa · s: Δn = 0.109; Δε = −3.8.

Use Example 17

| | | |
|---|---|---|
| V-H(3F2)HB-1 | (No. 119) | 5% |
| 1V2-BEB(F,F)-C | (5-15) | 6% |
| 3-HB-C | (5-1) | 16% |
| 2-BTB-1 | (13-10) | 10% |
| 5-HH-VFF | (13-1) | 28% |
| 3-HHB-1 | (14-1) | 4% |
| VFF-HHB-1 | (14-1) | 8% |
| VFF2-HHB-1 | (14-1) | 10% |
| 3-H2BTB-2 | (14-17) | 5% |
| 3-H2BTB-3 | (14-17) | 4% |
| 3-H2BTB-4 | (14-17) | 4% |

Use Example 18

| | | |
|---|---|---|
| 3-H(3F2)HB-2V | (No. 115) | 3% |
| 5-HB(F)B(F,F)XB(F,F)-F | (4-40) | 5% |
| 3-BB(F)B(F,F)XB(F,F)-F | (4-47) | 3% |
| 4-BB(F)B(F,F)XB(F,F)-F | (4-47) | 6% |
| 5-BB(F)B(F,F)XB(F,F)-F | (4-47) | 3% |
| 3-HH-V | (13-1) | 40% |
| 3-HH-V1 | (13-1) | 7% |
| 3-HHEH-5 | (14-13) | 3% |
| 3-HHB-1 | (14-1) | 3% |
| V-HHB-1 | (14-1) | 5% |
| V2-BB(F)B-1 | (14-6) | 5% |
| 1V2-BB-F | (2-1) | 3% |
| 3-BB(F,F)XB(F,F)-F | (3-97) | 11% |
| 3-HHBB(F,F)-F | (4-6) | 3% |

Use Example 19

| | | |
|---|---|---|
| 3-H(3F2)HB-1 | (No. 109) | 5% |
| 3-GB(F)B(F,F)XB(F,F)-F | (4-57) | 4% |
| 3-BB(F)B(F,F)XB(F,F)-F | (4-47) | 5% |
| 4-BB(F)B(F,F)XB(F,F)-F | (4-47) | 7% |
| 5-BB(F)B(F,F)XB(F,F)-F | (4-47) | 3% |
| 3-HH-V | (13-1) | 41% |
| 3-HH-V1 | (13-1) | 6% |
| 3-HHEH-5 | (14-13) | 3% |
| 3-HHB-1 | (14-1) | 3% |
| V-HHB-1 | (14-1) | 3% |
| V2-BB(F)B-1 | (14-6) | 5% |
| 1V2-BB-F | (2-1) | 3% |
| 3-BB(F,F)XB(F,F)-F | (3-97) | 5% |
| 3-GB(F,F)XB(F,F)-F | (3-113) | 4% |
| 3-HHBB(F,F)-F | (4-6) | 3% |

NI = 82.5° C.; η = 14.1 mPa · s: Δn = 0.105; Δε = 7.1.

INDUSTRIAL APPLICABILITY

The liquid crystal compound of the invention has good physical properties. A liquid crystal composition including this compound can be utilized for a liquid crystal display device in personal computers, television sets and so forth.

What is claimed is:

1. A compound represented by formula (1):

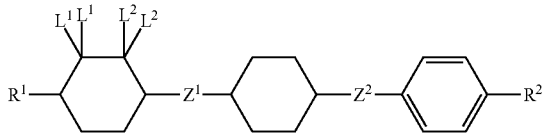

(1)

in formula (1), $R^1$ and $R^2$ is hydrogen, fluorine, chlorine or alkyl having 1 to 20 carbons, and in the alkyl at least one —CH$_2$— may be replaced by —O—, at least one —CH$_2$CH$_2$— may be replaced by —CH=CH—, and in these groups at least one hydrogen may be replaced by fluorine;

wherein $L^1$ is either fluorine or hydrogen, wherein $L^2$ is either fluorine or hydrogen, and wherein $L^1$ is fluorine, both $L^1$s are fluorine and wherein when $L^2$ is fluorine, both $L^2$s are fluorine and wherein when both $L^1$s are fluorine, both $L^2$s are hydrogen and wherein when both $L^2$s are fluorine both $L^1$s are hydrogen; and $Z^1$ and $Z^2$ are independently a single bond, —COO—, —OCO—, —OCH$_2$—, —CH$_2$O—, —CF$_2$O—, —OCF$_2$—, —CH$_2$CH$_2$—, —CH=CH—, —C≡C—, —CF$_2$CF$_2$—, —CF=CF—, —CH$_2$CH$_2$CH$_2$CH$_2$—, —CH=CHCH$_2$CH$_2$— or —CH$_2$CH=CHCH$_2$—;

where at least one of $Z^1$ and $Z^2$ is —COO—, —OCO—, —OCH$_2$—, —CH$_2$O—, —CF$_2$O—, —OCF$_2$—, —CH$_2$CH$_2$—, —CH=CH—, —C≡C—, —CF$_2$CF$_2$—, —CF=CF—, —CH$_2$CH$_2$CH$_2$CH$_2$—, —CH=CHCH$_2$CH$_2$— or —CH$_2$CH=CHCH$_2$—, when both $R^1$ and $R^2$ is alkyl having 1 to 20 carbons and $L^1$ is fluorine;

where at least one of $Z^1$ and $Z^2$ is —COO—, —OCO—, —OCH$_2$—, —CH$_2$O—, —CF$_2$O—, —OCF$_2$—, —CH$_2$CH$_2$—, —CH=CH—, —C≡C—, —CF$_2$CF$_2$—, —CF=CF—, —CH$_2$CH$_2$CH$_2$CH$_2$—, —CH=CHCH$_2$CH$_2$— or —CH$_2$CH=CHCH$_2$—, when $R^1$ is alkyl having 1 to 20 carbons, $R^2$ is alkoxy having 1 to 19 carbons, and $L^2$ is fluorine.

2. The compound according to claim 1, wherein the compound is represented by formula (1-1), formula (1-2) or formula (1-3):

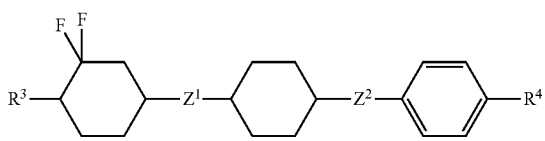

(1-1)

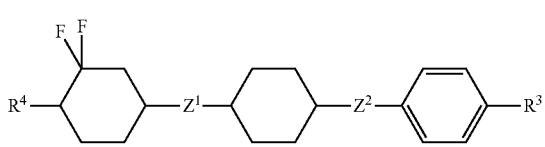

(1-2)

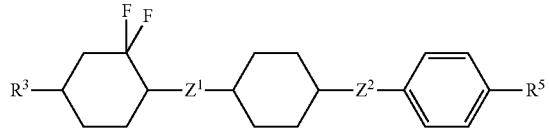

(1-3)

in formula (1-1), formula (1-2) and formula (1-3), $R^3$ is alkyl having 1 to 10 carbons, alkoxy having 1 to 9 carbons, alkoxyalkyl having 2 to 9 carbons, alkenyl having 2 to 10 carbons or alkenyloxy having 2 to 9 carbons, $R^4$ is alkoxy having 1 to 9 carbons, alkoxyalkyl having 2 to 9 carbons, alkenyl having 2 to 10 carbons or alkenyloxy having 2 to 9 carbons, $R^5$ is alkyl having 1 to 10 carbons or alkenyl having 2 to 10 carbons; and $Z^1$ and $Z^2$ are a single bond, —COO—, —CF$_2$O—, —CH$_2$CH$_2$—, —CH=CH—, —C≡C—, —CF$_2$CF$_2$—, —CF=CF—, —CH$_2$CH$_2$CH$_2$CH$_2$—, —CH=CHCH$_2$CH$_2$— or —CH$_2$CH=CHCH$_2$—.

3. The compound according to claim 1, wherein the compound is represented by formula (1-1-1), formula (1-2-1) or formula (1-3-1):

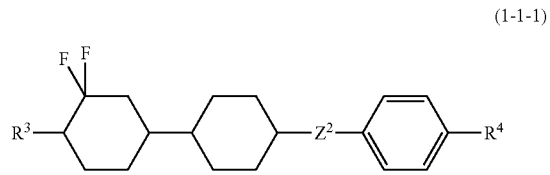

(1-1-1)

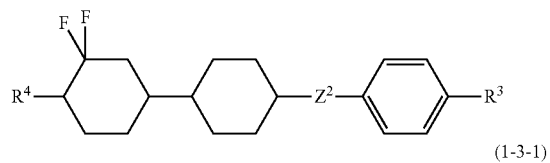

(1-2-1)

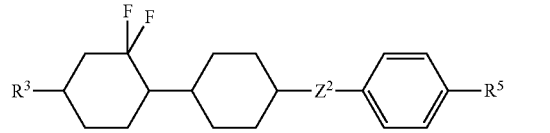

(1-3-1)

in formula (1-1-1), formula (1-2-1) and formula (1-3-1), $R^3$ is alkyl having 1 to 10 carbons, alkoxy having 1 to 9 carbons, alkoxyalkyl having 2 to 9 carbons, alkenyl having 2 to 10 carbons or alkenyloxy having 2 to 9 carbons; $R^4$ is alkoxy having 1 to 9 carbons, alkoxyalkyl having 2 to 9 carbons, alkenyl having 2 to 10 carbons or alkenyloxy having 2 to 9 carbons; $R^5$ is alkyl having 1 to 10 carbons or alkenyl having 2 to 10 carbons; and $Z^2$ is a single bond, —COO—, —OCH$_2$—CF$_2$O—, —CH$_2$CH$_2$—, —CF$_2$CF$_2$—, —CH$_2$CH$_2$CH$_2$CH$_2$—, —CH=CHCH$_2$CH$_2$— or —CH$_2$CH=CHCH$_2$—.

4. The compound according to claim 3, wherein in formula (1-1-1), formula (1-2-1) and formula (1-3-1), $Z^2$ is a single bond, —COO—, —OCH$_2$—CF$_2$O— or —CH$_2$CH$_2$—.

5. The compound according to claim 3, wherein in formula (1-1-1), formula (1-2-1) and formula (1-3-1), $Z^2$ is a single bond, —COO— or —CH$_2$CH$_2$—.

6. The compound according to claim 1, wherein the compound is represented by formula (1-1-1-1), formula (1-2-1-1) or formula (1-3-1-1):

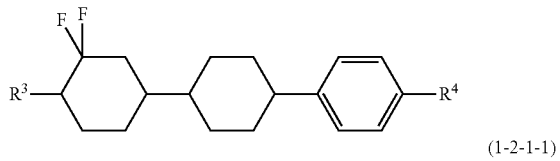
(1-1-1-1)

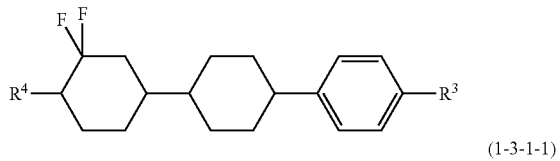
(1-2-1-1)

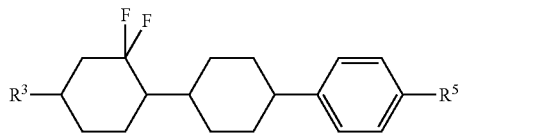
(1-3-1-1)

in formula (1-1-1-1), formula (1-2-1-1) and formula (1-3-1-1),
$R^3$ is alkyl having 1 to 5 carbons, alkoxy having 1 to 4 carbons or alkenyl having 2 to 5 carbons; $R^4$ is alkoxy having 1 to 4 carbons or alkenyl having 2 to 5 carbons; and $R^5$ is alkyl having 1 to 5 carbons or alkenyl having 2 to 5 carbons.

7. The compound according to claim 6, wherein in formula (1-1-1-1), formula (1-2-1-1) and formula (1-3-1-1), $R^1$ is alkyl having 1 to 5 carbons; $R^2$ is alkenyl having 2 to 5 carbons; and $R^3$ is alkyl having 1 to 5 carbons.

8. A liquid crystal composition including a compound according to claim 1.

9. The liquid crystal composition according to claim 8, further including at least one compound selected from the group of compounds represented by formulas (2) to (4):

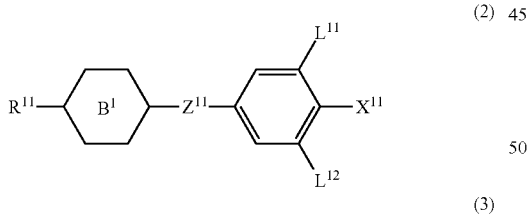
(2)

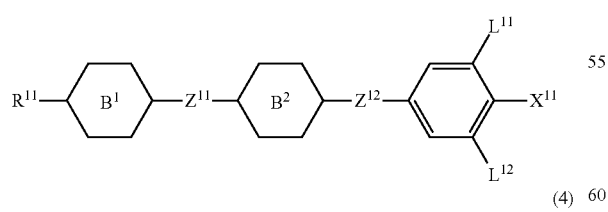
(3)

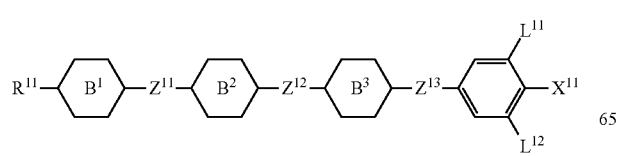
(4)

in formulas (2) to (4),
$R^{11}$ is alkyl having 1 to 10 carbons or alkenyl having 2 to 10 carbons, and in the alkyl and alkenyl at least one —$CH_2$— may be replaced by —O—, and in these groups at least one hydrogen may be replaced by fluorine;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $B^1$, ring $B^2$ and ring $B^3$ are independently 1,4-cyclohexylene, 1,4-phenylene, 1,4-phenylene in which at least one hydrogen has been replaced by fluorine, tetrahydropyran-2,5-diyl, 1,3-dioxane-2,5-diyl or pyrimidine-2,5-diyl;

$Z^{11}$, $Z^{12}$ and $Z^{13}$ are independently —COO—, —OCO—, —$CH_2O$—, —$OCH_2$—, —$CF_2O$—, —$OCF_2$—, —$CH_2CH_2$—, —CH=CH—, —C≡C— or —$(CH_2)_4$—; and $L^{11}$ and $L^{12}$ are independently hydrogen or fluorine.

10. The liquid crystal composition according to claim 8, further including at least one compound selected from the group of compounds represented by formula (5):

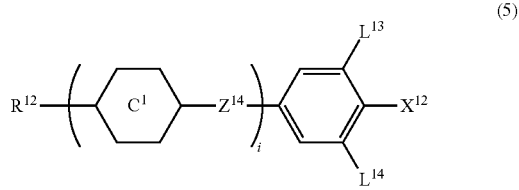
(5)

in formula (5),
$R^{12}$ is alkyl having 1 to 10 carbons or alkenyl having 2 to 10 carbons, and in the alkyl and alkenyl at least one —$CH_2$— may be replaced by —O—, and in these groups at least one hydrogen may be replaced by fluorine;

$X^{12}$ is —C≡N— or —C≡C—C≡N;

ring $C^1$ is 1,4-cyclohexylene, 1,4-phenylene, 1,4-phenylene in which at least one hydrogen has been replaced by fluorine, tetrahydropyran-2,5-diyl, 1,3-dioxane-2,5-diyl or pyrimidine-2,5-diyl;

$Z^{14}$ is a single bond, —COO—, —OCO—, —$CH_2O$—, —$OCH_2$—, —$CF_2O$—, —$OCF_2$—, —$CH_2CH_2$— or —C≡C—;

$L^{13}$ and $L^{14}$ are independently hydrogen or fluorine; and i is 1, 2, 3 or 4.

11. The liquid crystal composition according to claim 8, further including at least one compound selected from the group of compounds represented by formulas (6) to (12):

(6)
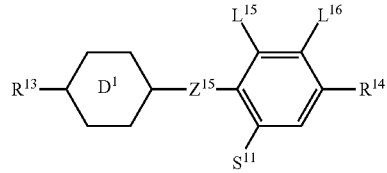

(7)
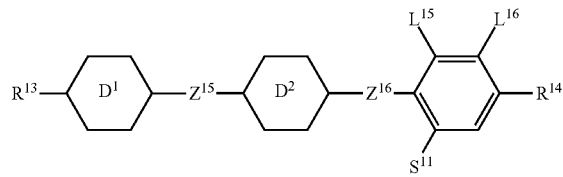

(8)
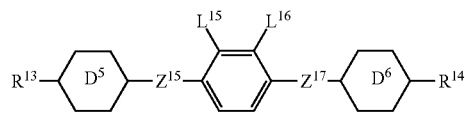

(9)
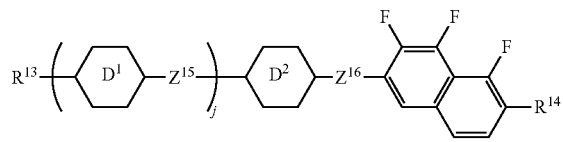

(10)
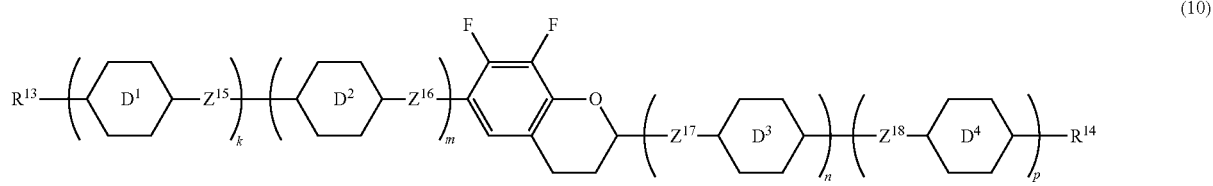

(11)
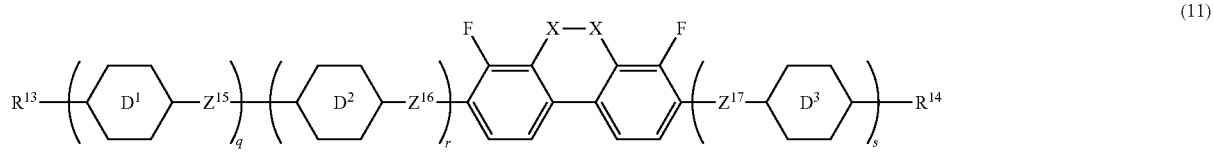

(12)

in formulas (6) to (12),
- $R^{13}$, $R^{14}$ and $R^{15}$ are independently alkyl having 1 to 10 carbons or alkenyl having 2 to 10 carbons, and in the alkyl and alkenyl at least one —$CH_2$— may be replaced by —O—, and in these groups at least one hydrogen may be replaced by fluorine, and $R^{15}$ may be hydrogen or fluorine;
- ring $D^1$, ring $D^2$, ring $D^3$ and ring $D^4$ are independently 1,4-cyclohexylene, 1,4-cyclohexenylene, 1,4-phenylene, 1,4-phenylene in which at least one hydrogen has been replaced by fluorine, tetrahydropyran-2,5-diyl or decahydronaphthalene-2,6-diyl;
- ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;
- $Z^{15}$, $Z^{16}$, $Z^{17}$ and $Z^{18}$ are independently a single bond, —COO—, —OCO—, —$CH_2O$—, —$OCH_2$—, —$CF_2O$—, —$OCF_2$—, —$CH_2CH_2$—, —$CF_2OCH_2CH_2$— or —$OCF_2CH_2CH_2$—;
- $L^{15}$ and $L^{16}$ are independently fluorine or chlorine;
- $S^{11}$ is hydrogen or methyl;
- X is —CHF— or —$CF_2$—; and
- j, k, m, n, p, q, r and s are independently 0 or 1, the sum of k, m, n and p is 1 or 2, the sum of q, r and s is 0, 1, 2 or 3, and t is 1, 2 or 3.

12. The liquid crystal composition according to claim 8, further including at least one compound selected from the group of compounds represented by formulas (13) to (15):

(13)
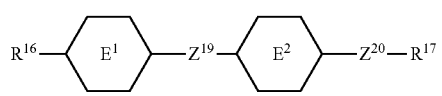

(14)
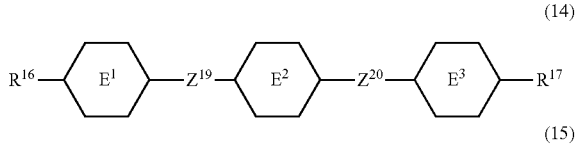

(15)
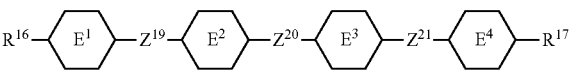

in formulas (13) to (15),
- $R^{16}$ and $R^{17}$ are independently alkyl having 1 to 10 carbons or alkenyl having 2 to 10 carbons, and in the alkyl and alkenyl at least one —$CH_2$— may be replaced by —O—, and in these groups at least one hydrogen may be replaced by fluorine;
- ring $E^1$, ring $E^2$, ring $E^3$ and ring $E^4$ are independently 1,4-cyclohexylene, 1,4-phenylene, 2-fluoro-1,4-phenylene, 2,5-difluoro-1,4-phenylene or pyrimidine-2,5-diyl; and
- $Z^{19}$, $Z^{20}$ and $Z^{21}$ are independently a single bond, —COO—, —$CH_2CH_2$—, —CH=CH— or —C≡C—, where in formulas (14) and (15), when one of $R^{16}$ and $R^{17}$ is alkenyl having 2 to 10 carbons in which at least one hydrogen may be replaced by fluorine, the other is alkyl having 1 to 10 carbons in which at least one hydrogen may be replaced by fluorine.

13. A liquid crystal display device containing the liquid crystal composition according to claim 8.

* * * * *